US007709191B2

(12) United States Patent
Philpott et al.

(10) Patent No.: US 7,709,191 B2
(45) Date of Patent: *May 4, 2010

(54) HETERODUPLEX TRACKING ASSAY

(75) Inventors: Sean Philpott, Defreestville, NY (US); Barbara Weiser, East Greenbush, NY (US); Harold Burger, East Greenbush, NY (US); Christina Kitchen, Sherman Oaks, CA (US)

(73) Assignee: Health Research, Inc., Rensselaer, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/174,141

(22) Filed: Jul. 16, 2008

(65) Prior Publication Data
US 2009/0047662 A1 Feb. 19, 2009

Related U.S. Application Data

(60) Division of application No. 11/654,897, filed on Jan. 17, 2007, and a continuation-in-part of application No. 11/333,073, filed on Jan. 17, 2006, now Pat. No. 7,344,830, which is a continuation-in-part of application No. 10/695,846, filed on Oct. 29, 2003, now Pat. No. 7,294,458, which is a division of application No. 09/963,064, filed on Sep. 25, 2001, now Pat. No. 6,727,060.

(60) Provisional application No. 60/838,009, filed on Aug. 16, 2006, provisional application No. 60/282,354, filed on Apr. 6, 2001, provisional application No. 60/235,671, filed on Sep. 26, 2000.

(51) Int. Cl.
*G01N 33/569* (2006.01)
*C12Q 1/70* (2006.01)

(52) U.S. Cl. ............... 435/5; 435/41; 435/235.1; 435/325; 435/372; 435/372.3

(58) Field of Classification Search .......... None
See application file for complete search history.

(56) References Cited

U.S. PATENT DOCUMENTS

| | | | |
|---|---|---|---|
| 5,837,464 | A | 11/1998 | Capon et al. |
| 5,851,759 | A | 12/1998 | Weiner |
| 5,994,515 | A | 11/1999 | Hoxie |
| 6,107,019 | A | 8/2000 | Allaway et al. |
| 6,727,060 | B2 | 4/2004 | Philpott et al. |
| 7,097,970 | B2 | 8/2006 | Petropoulos et al. |
| 7,169,551 | B2 | 1/2007 | Petropoulos et al. |
| 2003/0180717 | A1 | 9/2003 | Esteban et al. |
| 2005/0214743 | A1 | 9/2005 | Richman et al. |
| 2006/0183110 | A1 | 8/2006 | Petropoulos et al. |
| 2006/0194227 | A1 | 8/2006 | Philpott et al. |
| 2006/0223107 | A1 | 10/2006 | Chenna et al. |

FOREIGN PATENT DOCUMENTS

| WO | WO 99 14378 A | 3/1999 |
|---|---|---|
| WO | 99/67429 | 12/1999 |
| WO | WO 00/65356 | 11/2000 |
| WO | WO 2006/110855 | 10/2006 |

OTHER PUBLICATIONS

Nelson, et al., "Evolutionary Variants of the Human Immunodeficiency Virus Type 1 V3 Region Characterized by Using a Heteroduplex Tracking Assay", Journal of Virology, Nov. 1997, vol. 71, No. 11, pp. 8750-8758.
L. Q. Zhang, et al., "Selection of Specific Sequences in the External Envelope Protein of Human Immunodeficiency Virus Type 1 upon Primary Infection", Journal of Virology, Jun. 1993, vol. 67, No. 6 pp. 3345-3356.
Shang Cao, et al., "Study on transient infection of T cell lines by M tropic HIV-1 strains", Chinese Journal of Experimental and Clinical Virology, vol. 13, No. 2, Jun. 1999, pp. 163-169.
Shan Li, et al., "Persistent CCR5 Utilization and Enhanced Macrophage Tropism by Primary Blood Human Immunodeficiency Virus Type 1 Isolates from Advanced Stages of Disease and Comparison to Tissue-Derived Isolates", Journal of Virology, Dec. 1999, vol. 73, No. 12, pates 9741-9755.
Julie A. E. Nelson, et al., "Patterns of Changes in Human Immunodeficiency Virus Type 1 V3 Sequence Populations Late in Infection", Journal of Virology, Sep. 2000, vol. 74, No. 18, pp. 8494-8501.
Timothy J. Wilkin, et al., "HIV Type 1 Chemokine Coreceptor Use among Antiretroviral-Experienced Patients Screened for a Clinical Trial of a CCR5 Inhibitor: AIDS Clinical Trial Group A5211", Clinical Infectious Diseases, Feb. 15, 2007, vol. 44, No. 4, pp. 591-595.
Charlotte Tscherning-Casper, et al., "Coreceptor Usage of HIV-1 Isolates Representing Different Genetic Subtypes Obtained From Pregnant Cameroonian Women", Journal of Acquired Immune Deficiency Syndromes, vol. 24, No. 1, May 1, 2000, pp. 1-9.

(Continued)

*Primary Examiner*—Mary E Mosher
*Assistant Examiner*—Stuart W Snyder
(74) *Attorney, Agent, or Firm*—Frommer Lawrence & Haug LLP; Thomas J. Kowalski; Heather J. DiPietrantonio

(57) ABSTRACT

A change in viral tropism occurs in many HIV positive individuals over time and may be indicated by a shift in coreceptor use from CCR5 to CXCR4. The shift in coreceptor use to CXCR4 has been shown to correlate with increased disease progression. In patients undergoing HAART, the predominant populations of virus may be shifted back to CCR5-mediated entry soon after the CXCR4-specific strains have emerged. The present invention relates to a diagnostic method to monitor coreceptor use in the treatment and clinical management of human immunodeficiency virus (HIV) infection. The present invention further relates to a diagnostic method applied to HIV-positive individuals undergoing HAART to monitor the suppression of CCR5- or CXCR4-specific strains. The diagnostic methods may be used to assist in selecting antiretroviral therapy and to improve predictions of disease prognosis over time. The methods of the invention include cell-based methods, including cell fusion assays, and molecular-based methods, including heteroduplex tracking assay, to both quantitatively and qualitatively analyze patient-derived HIV for coreceptor usage.

16 Claims, 8 Drawing Sheets

OTHER PUBLICATIONS

Dalma Vodros et al., "Quantitative Evaluation of HIV-1 Coreceptor Usin in the Ghost (3) Cell Assay", Virology, vol. 291, No. 1, Dec. 5, 2001, pp. 1-11.

Paul R. Gorry et al., "Macrophage Tropism of Human Immunodeficiency Virus Type 1 Isolates from Brain and Lymphoid Tissues Predicts Neurotropism Independent of Coreceptor Specificity", Journal of Virology, Nov. 2001, vol. 75, No. 21, pp. 10073-10089.

Philpott S. et al. "Preferential suppression of CXCR4-specific strains of HIV-1 by antiviral therapy." J. Clin. Invest., vol. 107(4), Feb. 2001, p. 431-438.

Moore JP, et al. "Co-receptors for HIV-1 entry." Cur. Opin. Immunol., vol. 9, 1997, pp. 551-562.

Callaway DS, et al. "Virus phenotype switching and disease progression in HIV-1 infection." Proc. R. Soc. Lond., vol. 266, 1999 pp. 2523-2530.

Wodarz D, et al. "Defining CTL-induced pathology: implications for HIV." Virology, vol. 274, Aug. 2000, pp. 94-104.

Clerici, et al. (2000) "Different immunologic profiles characterize HIV infection in highly active antiretroviral therapy-treated and antiretroviral-naïve patients with undetectable viraemia. The Master Group". AIDS 14(2): 109-116.

Conner, et al. "Change in coreceptor use correlates with disease progression in HIV-1 infected individuals" J. Exp. Med. vol. 185(4). Feb. 17, 1997, pp. 621-628.

Bjomdal, et al. "Coreceptor usage of primary human immunodeficiency virus type 1 isolates varies according to biological phenotype" Journal of Virology, Oct. 1997, pp. 7478-7487.

Burger and Weiser, (1997) "Biology of HIV-1 in women and men" Obstetrics and Gynecology Clinics of North America, vol. 24, No. 4, pp. 731-742.

Pierson, et al. (2000) "Characterization of chemokine receptor utilization of viruses in the latent reservoir for human immunodeficiency virus type 1". J. Virol. 74(17): 7824-33.

Mosier (2000) "Virus and target cell evolution in human immunodeficiency virus type 1 infection", Immunologic Research, vol. 21, No. 2-3, pp. 253-258.

Verrier, et al. (1999) "Role of the HIV type 1 glycoprotein 120 V3 loop in determining coreceptor usage" AIDS Research and Human Retroviruses, vol. 15, No. 9, 1999, pp. 731-743.

Chan, et al. (1999) "V3 recombinants indicate a central role for CCR5 as a coreceptor in tissue infection by human immunodeficiency virus type 1" Journal of Virology, Mar. 1999, pp. 2350-2358.

Anderson, et al. (1998) "Early reduction of immune activation in lymphoid tissue following highly active HIV therapy" AIDS 12:F123-9.

Berger, et al. (1999) "Chemokine receptors as HIV-1-coreceptors: roles in viral entry, tropism and disease." Annu. Rev. Immunol 17:657-700.

Berkowitz, et al. (2000) "Casual relationships between HIV-1 coreceptor utilization, tropism, and pathologenesis in human thymus." J. AIDS Hum. Retro. 16(11):1039-45.

Cammack N. (1999) "Human Immunodeficiency virus type 1 entry and chemokine receptors: a new therapeutic target." Antivir. Chem. Chemother. 10(2):53-62.

Cecilia, et al. (2000) "Absence of coreceptor switch with disease progression in human immunodeficiency virus infections in India" Virology 271(2):253-8.

Dreyer, et al. (1999) "Primary isolate neutralization by HIV type 1-infected patient sera in the era of highly active antiretroviral therapy." AIDS Res. Hum. Retrovir 15(17):1563-1571.

Equils, et al. (2000) "Recovery of replication-competent virus from CD4 T cell reservoirs and change in coreceptor use in human immunodeficiency virus type 1-infected children responding to highly active antiretroviral therapy." J. Inf. Dis. 182:751-757.

Este, et al. (1999) "Shift of clinical human immundeficiency virus type 1 isolates from X4 to R5 and prevention of emergence of the syncytium-inducing phenotype by blockade of CXCR4". J. Virol. 73:5577-85.

Fang, et al. (1996) "Molecular cloning of full-length HIV-1 genomes directly from plasma viral RNA". J. Acquir. Immune Defic. Syndr. Hum. Retrovirol. 12(4):352-7.

Giovannetti, et al. (1999) "CCR5 and CXCR4 chemokine receptor expression and beta-chemokine production during early T cell repopulation induced by highly active anti-retroviral therapy". Clin. Exp. Immunol. 118(1):87-94.

Glushakova, et al. (2000) "Preferential coreceptor utilization and cytopathicity by dual-topic HIV-1 in human lymphoid tissue ex vivo". J. Clin. Invest. 104:R7-R11.

Hotkamp, et al. (2000) "Unexpected coreceptor usage of primary human immunodeficiency virus type 1 isolates from viremic patients under highly active antiretroviral therapy." J. Inf. Dis. 181(2):513-21.

Kokkotou, et al. (2000) "In vitro correlates of HIV-2-mediated HIV-1 protection." Proc. Natl. Acad. Sci. USA 97(12):6797-8002.

Kusunoki, et al. (1999) "Antisense oligodeoxynulceotide complementary to CXCR4 mRNA block replication of HIV-1 in COS cells." Nucleosides Nucleotides 18(6-7): 1705-8.

Lee, et al. (1999) "Quantification of CD4, CCR5, and CXCR4 levels on lymphocyte subsets, dendritic cells, and differentially conditioned monocyte-derived macrophages" Proc. Natl. Acad. Sci. USA 96(9):5215-20.

Lew, et al. (1998) "Determinations of levels of human immunodeficiency virus type 1 RNA in plasma: reassessment of parameters affecting assay outcome. TUBE Meeting Workshop Attendees. Technology Utilization for HIV-1 Blood Evaluation and Standardization in Pediatrics." J. Clin. Microbiology (36)6:1471-9.

Martinon, et al. (1999) "Persistent alterations in T-cell repertoire, cytokine and chemokine receptor gene expression after 1 year of highly active antiretroviral therapy." AIDS. 13(2):185-94.

Michael, et al. (1999) "Viral phenotype and CCR5 genotype", Nat. Med. 5(12):1330.

Philpott, et al. (1999) "Antiviral therapy may preferentially eliminate CXCR4-specific strains of HIV-1" Interscience Conference on Antimicrobial Agents and Chemotherapy (ICAAC) Moscone Center San Francisco, CA, USA, Sep. 26-29, 1999 Abstract 1836 p. 513.

Samson, et al. (1996) "Resistance to HIV-1 infection in Caucasian individuals bearing mutant alleles of the CCR-5 chemokine receptor gene", Nature 382:722-5.

Schramm, et al. (2000) "Viral entry through CXCR4 is a pathogenic factor and therapeutic target in human immunodeficiency virus type 1 disease", J. Virol. 74(1):184-92.

Shankarappa, et al. (1999) "Consistent viral evolutionary changes associated with the progression of human immunodeficiency virus type 1 infection", J. Virol. 73(12):10489-502.

Trkola, et al. (1999) "A cell line-based neutralization assay for primary human immunodeficiency virus type 1 isolates that use either the CCR5 or the CXCR4 coreceptor", J. Virol. 73(11):8966-8974.

Vicenzi, et al. (1999) "Envelope-dependent restriction of human immunodeficiency virus type 1 spreading in CD$(+) T lymphocytes: R5 but not X4 viruses replicate in the absence of T-cell receptor restimulation", J. Virol. 73(9):7515-23.

Wang, et al. (2000) "Molecular and biological interactions between two HIV-1 strains from a coinfected patient reveal the first evidence in favor of viral synergism" Virology 274(1):105-119.

Zhang, et al. (1999) "Will multiple coreceptors need to be targeted by inhibitors of human immunodeficiency virus type 1 entry", J. Virol. 73(4):3443-8.

Penn, et al., "CXCR4 utilization is sufficient to trigger CD4+ T cell depletion in HIV-1-infected human lymphoid tissue", Proceedings of the National Academy of Sciences of the United States of America, vol. 96, No. 2(Jan. 19, 1999), pp. 663-668.

Overbaugh, et al., "Distinct but related human immunodeficiency virus type 1 variant populations in genital secretions and blood", AIDS Research and Human Retroviruses, vol. 12, No. 2(Jan. 20, 1996), pp. 107-115. Abstract Only.

Bazan, et al., Patterns of CCR5, CXCR4, and CCR3 Usage by Envelope Glycoproteins from Human Immunodeficiency Virus Type 1 Primary Isolates. Journal of Virology, May 1998, vol. 72, No. 5, p. 4485-4491.

Nicholson, J, et al. "CCR5 and CXCR4 on memory and neive T cells in HIV infection and response to highly active antire tro viral therapy", JAIDS Journal of Acquired Immune Deficiency Syndrome (2001) vol. 27, No. pp. 101-115.

Marcel, J, et al. "CXCR4 and CCR5 regulation and expression pattern on T- and monocyte-macrophage cell lineage: Implication for succeptability to infection by HIV-1" Mathematical Biosciences (2005) Vo. 195, pp. 92-126.

Ansari, et al., "Implications of X4 tropic virus detection before HAART and disease progression", AIDS (2008) vol. 22, pp. 533-534.

Burger and Hoover, HIV-1 Tropism, Disease Progression, and Clinical Management, JID (2008) vol. 198, pp. 1095-1097.

Cardozo, et al., Structural Basis for Coreceptor Selectivity by the HIV Type 1 V3 Loop, Aids Research and Human Retrovirus (2007) vol. 23, pp. 415-426.

Daar, et al. "Baseline HIV Type 1 Coreceptor Tropism Predicts Disease Progression", Clinical Infectious Diseases (2007) vol. 45, pp. 643-649.

De Mendoza, et al., "Prevalence of X4 Tropic Viruses in Patients Recently Infected with HIV-1 and Lack of Association with Transmission of Drug Resistance", Journal of Antimicrobial Chemotherapy (2007) vol. 59, pp. 698-704.

Goetz, et al., "Relationship between HIV coreceptor tropism and disease progression in persons with untreated chronic HIV infection", J Acquir Immune Defic Syndr (2009) vol. 50, No. 3, pp. 259-266.

McCarthy, et al., "Comparison of Phenotypic (Trofile*) and Genotypic SensiTrop II) Assays to Determine HIV Tropism in Treatment-Naïve Subjects" Presented at the 16$^{th}$ Conference on Retroviruss and Opportunistic Infections, Montreal, Canada, Feb. 8-11, 2009.

Pastore, et al., "Instrinsic Obstacles to Human Immunodeficiency Virus Type 1 Coreceptor Switching" Journal of Virology (2004) vol. 78, No. 14, pp. 7565-7574.

Shepard, et al., "Emergence and Persistence of CXCR4-Tropic HIV-1 in a Population of Men from the Multicenter AIDS Cohort Study" JID (2008) vol. 198, pp. 1104-1112.

Weiser, et al., "HIV-1 coreceptor usage and CXCR4-specific viral load predict clinical disease progression during combination antiretroviral therapy" AIDS (2008) vol. 22, pp. 469-479.

Thomas, et al., "Capillary Electrophoresis-based Heteroduplex Analysis with a Universal Heteroduplex Generator for Detection of a Point Mutations Associated with Rifampin Resistance in Tuberculosis", Clinical Chemistry (2001) 47:7, pp. 1195-1203.

Resch, et al., "A Multiple-site-specific heteroduplex tracking assay as a tool for the study of viral population dynamics", PNAS (2001) 98:1, pp. 176-181.

Rossi, et al., "An heteroduplex mobility analysis assay based on capillary electrophoresis for the study of HCV quasispecies", Journal of Virological Methods (2003) vol. 110, pp. 37-49.

Nelson, et al., "Patterns of changes in human immunodeficiency virus type 1 V3 sequence populations late in infection", Journal of Virology, The American Society for Microbiology, vol. 74, No. 18 (2000) pp. 8494-8501.

Schroeder, et al., "Characterization of intersubtype recombinant HIV type 1 genomes using a nonradioactive heteroduplex tracking assay", AIDS Research and Human Retroviruses APR, vol. 21, No. 4, (2005) pp. 314-318.

Freel, et al., "Characterization of human immunodeficiency virus type 1 in saliva and blood plasma by V3-specifice heteroduplex tracking assay and genotype analyses", Journal of Virology, vol. 75, No. 10 (2001) pp. 4936-4940.

Philpott, "HIV-1 coreceptor usage, transmission, and disease progression", Current HIV Research, Bentham Science Publishers, vol. 1, No. 2 (2003) pp. 217-227.

Wolinsky, et al., "Effect of a CCR5 inhibitor on viral loads in macaques dual-infected with R5 and X4 primate immunodeficiency viruses", Virology, vol. 328, No. 1 (2004) pp. 19-29.

SEQUENCE LISTING

<160> NUMBER OF SEQ ID NOS: 40

<210> SEQ ID NO 1
<211> LENGTH: 35
<212> TYPE: PRT
<213> ORGANISM: Human immunodeficiency virus

<400> SEQUENCE: 1

Cys Ile Arg Pro Asn Asn Asn Thr Arg Thr Ser Ile Arg Ile Gly Pro
1               5                   10                  15

Gly Gln Ala Phe Tyr Ala Thr Gly Asn Ile Ile Gly Asp Ile Arg Gln
            20                  25                  30

Ala Tyr Cys
        35

<210> SEQ ID NO 2
<211> LENGTH: 35
<212> TYPE: PRT
<213> ORGANISM: Human immunodeficiency virus

<400> SEQUENCE: 2

Cys Ile Arg Pro Asn Asn Asn Thr Arg Thr Ser Ile Arg Ile Gly Pro
1               5                   10                  15

Arg Gln Ala Phe Tyr Ala Thr Gly Asn Ile Ile Gly Asp Ile Arg Gln
            20                  25                  30

Ala Tyr Cys
        35

<210> SEQ ID NO 3
<211> LENGTH: 35
<212> TYPE: PRT
<213> ORGANISM: Human immunodeficiency virus

<400> SEQUENCE: 3

Cys Ile Arg Pro Asn Asn Asn Thr Arg Thr Ser Ile Arg Ile Gly Pro
1               5                   10                  15

Gly Gln Ala Phe Tyr Ala Thr Gly Asn Ile Val Gly Asp Ile Arg Gln
            20                  25                  30

Ala Tyr Cys
        35

<210> SEQ ID NO 4
<211> LENGTH: 27
<212> TYPE: PRT
<213> ORGANISM: Human immunodeficiency virus

<400> SEQUENCE: 4

Arg Lys Ser Val His Ile Gly Pro Gly Gln Ala Phe Tyr Ala Thr Gly
1               5                   10                  15

Asp Ile Ile Gly Asn Ile Arg Lys Ala His Cys
            20                  25

<210> SEQ ID NO 5
<211> LENGTH: 35
<212> TYPE: PRT
<213> ORGANISM: Human immunodeficiency virus

<400> SEQUENCE: 5

Cys Thr Arg Pro Asn Asn Asn Thr Arg Lys Ser Val His Ile Gly Pro
1               5                   10                  15

-continued

```
Gly Gln Ala Phe Tyr Ala Thr Gly Asp Ile Ile Gly Asn Ile Arg Lys
            20                  25                  30

Ala His Cys
        35

<210> SEQ ID NO 6
<211> LENGTH: 35
<212> TYPE: PRT
<213> ORGANISM: Human immunodeficiency virus

<400> SEQUENCE: 6

Cys Thr Arg Pro Asn Asn Asn Thr Arg Lys Ser Val His Ile Gly Pro
  1               5                  10                  15

Gly Gln Ala Phe Tyr Ala Thr Gly Asp Ile Ile Gly Asn Ile Arg Gln
            20                  25                  30

Ala His Cys
        35

<210> SEQ ID NO 7
<211> LENGTH: 35
<212> TYPE: PRT
<213> ORGANISM: Human immunodeficiency virus

<400> SEQUENCE: 7

Cys Thr Arg Pro Asn Asn Asn Thr Arg Lys Ser Val His Ile Gly Pro
  1               5                  10                  15

Gly Gln Ala Phe Tyr Ala Thr Gly Asp Ile Ile Gly Asn Met Arg Lys
            20                  25                  30

Ala His Cys
        35

<210> SEQ ID NO 8
<211> LENGTH: 35
<212> TYPE: PRT
<213> ORGANISM: Human immunodeficiency virus

<400> SEQUENCE: 8

Cys Thr Arg Pro Ile Asn Asn Arg Arg Lys Ser Ile His Met Gly Pro
  1               5                  10                  15

Gly Gln Ala Phe Tyr Gly Thr Asp Asp Ile Ile Gly Asp Ile Arg Lys
            20                  25                  30

Ala Arg Cys
        35

<210> SEQ ID NO 9
<211> LENGTH: 36
<212> TYPE: PRT
<213> ORGANISM: Human immunodeficiency virus

<400> SEQUENCE: 9

Cys Thr Arg Pro Ser Asn Asn Arg Arg Lys Ser Ile His Lys Gly Asp
  1               5                  10                  15

Gln Asp Lys His Ser Met Glu His Asp Asp Val Ile Gly Asp Ile Arg
            20                  25                  30

Lys Ala Arg Cys
        35

<210> SEQ ID NO 10
<211> LENGTH: 35
<212> TYPE: PRT
```

-continued

```
<213> ORGANISM: Human immunodeficiency virus

<400> SEQUENCE: 10

Cys Thr Arg Pro Ile Asn Asn Arg Arg Lys Ser Ile His Ile Gly Pro
1               5                   10                  15

Gly Gln Ala Phe Tyr Gly Thr Asp Ile Ile Gly Asp Ile Arg Gln
            20                  25                  30

Ala His Cys
        35

<210> SEQ ID NO 11
<211> LENGTH: 34
<212> TYPE: PRT
<213> ORGANISM: Human immunodeficiency virus

<400> SEQUENCE: 11

Cys Ile Arg Pro Asn Asn Asn Thr Arg Gln Ser Val His Ile Gly Pro
1               5                   10                  15

Gly Gln Ala Leu Tyr Thr Thr Glu Ile Ile Gly Asp Ile Arg Lys Ala
            20                  25                  30

His Cys

<210> SEQ ID NO 12
<211> LENGTH: 35
<212> TYPE: PRT
<213> ORGANISM: Human immunodeficiency virus

<400> SEQUENCE: 12

Cys Thr Arg Pro Asn Asn Asn Thr Ile Thr Ser Ile Arg Ile Gly Pro
1               5                   10                  15

Gly Gln Ala Phe Tyr Ala Thr Gly Ser Ile Ile Gly Asn Ile Arg Gln
            20                  25                  30

Ala His Cys
        35

<210> SEQ ID NO 13
<211> LENGTH: 35
<212> TYPE: PRT
<213> ORGANISM: Human immunodeficiency virus

<400> SEQUENCE: 13

Cys Thr Arg Pro Asn Asn Asn Thr Ile Thr Ser Ile Arg Ile Gly Pro
1               5                   10                  15

Gly Gln Ala Phe Tyr Ala Thr Gly Ser Ile Ile Gly Asn Thr Arg Gln
            20                  25                  30

Ala His Cys
        35

<210> SEQ ID NO 14
<211> LENGTH: 35
<212> TYPE: PRT
<213> ORGANISM: Human immunodeficiency virus

<400> SEQUENCE: 14

Cys Thr Arg Pro Asn Asp Asn Ile Arg Lys Ser Val His Ile Gly Pro
1               5                   10                  15

Gly Gln Ala Phe Tyr Ala Thr Gly Asp Ile Ile Gly Asp Ile Arg Arg
            20                  25                  30

Ala His Cys
        35
```

```
<210> SEQ ID NO 15
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ggcttaggca tctcctatgg caggaagaa                                    29

<210> SEQ ID NO 16
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ggcttaggca tctcctatgg caggaagaa                                    29

<210> SEQ ID NO 17
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
agaaagagca gaagacagtg gcaatga                                      27

<210> SEQ ID NO 18
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
agcccttcca gtcccccctt ttctttta                                     28

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gcacagtaca atgtacacat g                                            21

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
acaagaccca acaacaatac a                                            21
```

```
<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tgtattgttg ttgggtcttg t                                              21

<210> SEQ ID NO 22
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)
<223> OTHER INFORMATION: Gly or Ser
<220> FEATURE:
<221> NAME/KEY: MOD_RES
<222> LOCATION: (8)
<223> OTHER INFORMATION: variable amino acid
<220> FEATURE:
<221> NAME/KEY: MOD_RES
<222> LOCATION: (13)
<223> OTHER INFORMATION: variable amino acid
<220> FEATURE:
<221> NAME/KEY: MOD_RES
<222> LOCATION: (15)..(17)
<223> OTHER INFORMATION: variable amino acid
<220> FEATURE:
<221> NAME/KEY: MOD_RES
<222> LOCATION: (20)
<223> OTHER INFORMATION: Asp or Glu

<400> SEQUENCE: 22

Asn Asn Thr Arg Lys Xaa Ile Xaa Ile Gly Pro Gly Xaa Ala Xaa Xaa
 1               5                  10                  15

Xaa Thr Gly Xaa Ile Ile Gly
             20

<210> SEQ ID NO 23
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)
<223> OTHER INFORMATION: variable amino acid
<220> FEATURE:
<221> NAME/KEY: MOD_RES
<222> LOCATION: (8)
<223> OTHER INFORMATION: Lys, His, or Arg
<220> FEATURE:
<221> NAME/KEY: MOD_RES
<222> LOCATION: (13)
<223> OTHER INFORMATION: variable amino acid
<220> FEATURE:
<221> NAME/KEY: MOD_RES
<222> LOCATION: (15)..(17)
<223> OTHER INFORMATION: variable amino acid
<220> FEATURE:
<221> NAME/KEY: MOD_RES
<222> LOCATION: (20)
<223> OTHER INFORMATION: Asp or Glu
```

```
<400> SEQUENCE: 23

Asn Asn Thr Arg Lys Xaa Ile Xaa Ile Gly Pro Gly Xaa Ala Xaa Xaa
1               5                   10                  15

Xaa Thr Gly Xaa Ile Ile Gly
            20

<210> SEQ ID NO 24
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)
<223> OTHER INFORMATION: variable amino acid
<220> FEATURE:
<221> NAME/KEY: MOD_RES
<222> LOCATION: (8)
<223> OTHER INFORMATION: any naturally occurring amino acid other than
      Lys, His or Arg
<220> FEATURE:
<221> NAME/KEY: MOD_RES
<222> LOCATION: (13)
<223> OTHER INFORMATION: variable amino acid
<220> FEATURE:
<221> NAME/KEY: MOD_RES
<222> LOCATION: (15)..(17)
<223> OTHER INFORMATION: variable amino acid
<220> FEATURE:
<221> NAME/KEY: MOD_RES
<222> LOCATION: (20)
<223> OTHER INFORMATION: Asp, Glu, Lys, His or Arg

<400> SEQUENCE: 24

Asn Asn Thr Arg Lys Xaa Ile Xaa Ile Gly Pro Gly Xaa Ala Xaa Xaa
1               5                   10                  15

Xaa Thr Gly Xaa Ile Ile Gly
            20

<210> SEQ ID NO 25
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)
<223> OTHER INFORMATION: variable amino acid
<220> FEATURE:
<221> NAME/KEY: MOD_RES
<222> LOCATION: (8)
<223> OTHER INFORMATION: Lys, His or Arg
<220> FEATURE:
<221> NAME/KEY: MOD_RES
<222> LOCATION: (13)
<223> OTHER INFORMATION: variable amino acid
<220> FEATURE:
<221> NAME/KEY: MOD_RES
<222> LOCATION: (15)..(17)
<223> OTHER INFORMATION: variable amino acid
<220> FEATURE:
<221> NAME/KEY: MOD_RES
<222> LOCATION: (20)
<223> OTHER INFORMATION: Lys, His or Arg

<400> SEQUENCE: 25

Asn Asn Thr Arg Lys Xaa Ile Xaa Ile Gly Pro Gly Xaa Ala Xaa Xaa
1               5                   10                  15
```

Xaa Thr Gly Xaa Ile Ile Gly
            20

<210> SEQ ID NO 26
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
cctcagccat tacacaggcc tgtccaaag                                      29

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ttacagtaga aaaattcccc tc                                             22

<210> SEQ ID NO 28
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gaatctgtag aaattaattg tacaagac                                       28

<210> SEQ ID NO 29
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
tgctctacta atgttacaat gtgcttgtct tat                                 33

<210> SEQ ID NO 30
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
aattcgccct tgaatctgta gaaattaat                                      29

<210> SEQ ID NO 31
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
aattcgccct tttttgctct actaatg 27

<210> SEQ ID NO 32
<211> LENGTH: 35
<212> TYPE: PRT
<213> ORGANISM: Human immunodeficiency virus

<400> SEQUENCE: 32

Cys Thr Arg Pro Ile Asn Asn Arg Arg Lys Ser Ile His Ile Gly Pro
1               5                   10                  15

Gly Gln Ala Phe Tyr Gly Thr Asp Asp Ile Ile Gly Asp Ile Arg Gln
            20                  25                  30

Ala His Cys
        35

<210> SEQ ID NO 33
<211> LENGTH: 35
<212> TYPE: PRT
<213> ORGANISM: Human immunodeficiency virus

<400> SEQUENCE: 33

Cys Thr Arg Pro Ser Asn Asn Arg Arg Lys Ser Ile His Met Gly Pro
1               5                   10                  15

Gly Gln Ala Phe Tyr Gly Thr Asp Asp Ile Ile Gly Gly Ile Arg Lys
            20                  25                  30

Ala Arg Cys
        35

<210> SEQ ID NO 34
<211> LENGTH: 35
<212> TYPE: PRT
<213> ORGANISM: Human immunodeficiency virus

<400> SEQUENCE: 34

Cys Thr Arg Pro Ser Asn Asn Arg Arg Lys Ser Ile His Met Gly Pro
1               5                   10                  15

Gly Gln Ala Phe Tyr Gly Thr Asp Asp Ile Ile Gly Asp Ile Arg Lys
            20                  25                  30

Ala Arg Cys
        35

<210> SEQ ID NO 35
<211> LENGTH: 35
<212> TYPE: PRT
<213> ORGANISM: Human immunodeficiency virus

<400> SEQUENCE: 35

Cys Ile Arg Pro Asn Asn Asn Thr Arg Thr Ser Ile Arg Ile Gly Pro
1               5                   10                  15

Gly Gln Ala Phe Tyr Ala Thr Gly Asn Ile Ile Gly Gly Ile Arg Gln
            20                  25                  30

Ala Tyr Cys
        35

<210> SEQ ID NO 36
<211> LENGTH: 35
<212> TYPE: PRT
<213> ORGANISM: Human immunodeficiency virus

<400> SEQUENCE: 36

```
Cys Thr Arg Pro Asn Asn Asn Thr Arg Lys Ser Val His Ile Gly Leu
1               5                   10                  15

Gly Gln Ala Phe Tyr Ala Thr Gly Asp Ile Ile Gly Asn Ile Arg Lys
            20                  25                  30

Ala His Cys
        35

<210> SEQ ID NO 37
<211> LENGTH: 35
<212> TYPE: PRT
<213> ORGANISM: Human immunodeficiency virus

<400> SEQUENCE: 37

Cys Thr Arg Pro Asn Asn Asn Thr Arg Lys Ser Val His Ile Gly Pro
1               5                   10                  15

Gly Gln Ala Phe Tyr Ala Thr Gly Asp Ile Leu Gly Asn Ile Arg Gln
            20                  25                  30

Ala His Cys
        35

<210> SEQ ID NO 38
<211> LENGTH: 35
<212> TYPE: PRT
<213> ORGANISM: Human immunodeficiency virus

<400> SEQUENCE: 38

Cys Thr Arg Pro Asn Asn Asn Thr Arg Lys Ser Val His Ile Gly Pro
1               5                   10                  15

Gly Gln Ala Phe Tyr Ala Thr Gly Asp Ile Ile Gly Asp Ile Arg Gln
            20                  25                  30

Ala Tyr Cys
        35

<210> SEQ ID NO 39
<211> LENGTH: 35
<212> TYPE: PRT
<213> ORGANISM: Human immunodeficiency virus

<400> SEQUENCE: 39

Cys Thr Arg Pro Asn Asn Asn Thr Lys Lys Ser Val His Ile Gly Pro
1               5                   10                  15

Gly Gln Ala Phe Tyr Ala Thr Gly Asp Ile Ile Gly Asp Ile Arg Gln
            20                  25                  30

Ala Tyr Cys
        35

<210> SEQ ID NO 40
<211> LENGTH: 35
<212> TYPE: PRT
<213> ORGANISM: Human immunodeficiency virus

<400> SEQUENCE: 40

Cys Thr Arg Pro Asn Asp Asn Ile Arg Lys Arg Val His Ile Gly Pro
1               5                   10                  15

Gly Gln Ala Phe Tyr Ala Thr Gly Asp Val Ile Gly Asp Ile Arg Arg
            20                  25                  30

Ala His Cys
        35
```

HETERODUPLEX TRACKING ASSAY

RELATED APPLICATIONS/PATENT'S & INCORPORATION BY REFERENCE

This application is a divisional of U.S. application Ser. No. 11/654,897, filed Jan. 17, 2007, which claims priority to U.S. Provisional Application Ser. No. 60/838,009, filed Aug. 16, 2006 and which is a continuation-in-part of U.S. application Ser. No. 11/333,073, filed Jan. 17, 2006, and issued as U.S. Pat. No. 7,344,830, which is a continuation-in-part of U.S. application Ser. No. 10/695,846, filed Oct. 29, 2003, and issued as U.S. Pat. No. 7,294,458, which is a divisional application of U.S. application Ser. No. 09/963,064, filed Sep. 25, 2001 and issued as U.S. Pat. No. 6,727,060 on Apr. 27, 2004, and which claims priority to U.S. Provisional Application Ser. No. 60/282,354, filed Apr. 6, 2001 and U.S. Provisional Application Ser. No. 60/235,671, filed Sep. 26, 2000.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference. More generally, documents or references are cited in this text, either in a Reference List before the claims, or in the text itself; and, each of these documents or references ("herein-cited references"), as well as each document or reference cited in each of the herein-cited references (including any manufacturer's specifications, instructions, etc.), is hereby expressly incorporated herein by reference.

STATEMENT OF RIGHTS TO INVENTIONS MADE UNDER FEDERALLY SPONSORED RESEARCH

This work was supported by the government, in part, by Grant U01A135004 from the National Institute for Allergy and Infectious Diseases and a National Research Service Award (1F32HD08478-01) from the National Institute of Child Health and Human Development. The government may have certain rights to this invention.

FIELD OF THE INVENTION

The present invention relates to a diagnostic method to monitor coreceptor use in treatment of human immunodeficiency virus (HIV, or "an AIDS virus") infection. This method may assist in determining when to initiate antiretroviral therapy, in selecting antiretroviral therapy, and in predicting clinical disease progression during treatment. Moreover, the present invention relates to qualitative and quantitative methods for evaluating patient-derived HIV samples for coreceptor use, e.g. the presence and/or absence of CCR5 and CXCR4-specific strains or shifts in coreceptor use with respect to disease progression or treatment. The qualitative and quantitative methods of the invention may relate to cell-based systems, such as a cell-fusion assay, and molecular-based systems, such as a heteroduplex tracking assay, to monitor, measure, evaluate, detect, etc: the coreceptor use of patient-derived HIV. The present invention further relates to a diagnostic method to monitor the suppression of CXCR4-specific strains in HIV infected individuals undergoing antiretroviral therapy. The present invention also relates to a diagnostic method to determine HIV-1 coreceptor usage and CXCR4-specific viral load to determine when to initiate antiretroviral therapy, to predict clinical disease progression during combination antiretroviral therapy, and to determine when to change therapy.

BACKGROUND OF THE INVENTION

HIV uses a receptor-mediated pathway in the infection of host cells. HIV-1 requires contact with two cell-surface receptors to gain entry into cells and initiate infection; CD4 is the primary receptor. CXCR4 and CCR5, members of the chemokine receptor family of proteins, serve as secondary coreceptors for HIV-1 isolates that are tropic for T-cell lines or macrophages, respectively (Deng et al. (1996) Nature 381: 661-6; Doranz et al. (1996) Cell 86:1149-59; and Berger et al. (1998) Nature 391:240; Feng et al. (1996) Science 272:872-877; Samson et al. (1996) Nature 382:722-725).

CXCR4 or CCR5, in conjunction with CD4, form a functional cellular receptor for entry of certain strains of HIV into cells. Recent reports indicated that the viral envelope glycoprotein gp120 interacts directly with chemokine receptors generally at a step following CD4 binding (Lapham et al. (1996) Science 274:602-605; Moore (1997) Science 276:51; Wu et al. (1996) Nature 384:179-183; and Hesselgesser et al. (1997) Current Biology 7:112-121).

Coreceptor use therefore plays a critical role in viral tropism, pathogenesis, and disease progression. HIV-1 strains transmitted in vivo generally use CCR5 (R5 viruses), whether by sexual, parenteral, or mother-to-child transmission (Fenyo et al. (1998) Nature 391:240; Samson et al. (1996) Nature 382:722-5; Shankarappa et al. (1999) J. Virol. 73:10489-502; and Scarlatti et al. (1997); Berger et al. (1998); Björndal et al. (1997) J. Virol. 71:7478-7487). These viruses typically infect macrophages and primary CD4+ lymphocytes, and do not form syncytia in vitro (Journal et al. (1997) J. Virol. 71:7478-87); they are said to be macrophage tropic (M-tropic).

Years after chronic infection is established, strains using CXCR4 (X4 strains) emerge in approximately 50% of infected individuals (Berger et al. (1998); Scarlatti et al. (1997); Koot et al. (1993); and Connor et al. (1997) J. Exp. Med. 185:621-8). This is believed to be due to the ability of X4 strains to infect primary T-lymphocytes and then to further replicate in T-cell lines and induce syncytia (Björndal et al. (1997)); they are said to be T-cell tropic (T-tropic). X4 strains not only infect an expanded spectrum of crucial target cells as compared to R5 viruses, but they also exhibit increased cytopathicity and mediate bystander killing of uninfected cells (Blaak et al. (2000) Proc. Natl. Acad. Sci. USA 97:1269-74; Kreisberg et al. (2001) J. Virol. 75:8842-8847; Jekle et al. (2003) J. Virol. 77:5846-54).

Envelope variants selectively interact with either CXCR4 or CCR5. All of the known genetic determinates of coreceptor usage are found in the envelope gene (env), with the key determinates being found in the region of the env gene encoding the third variable (V3) domain of the gp120 glycoprotein. Previously, HIV-1 coreceptor utilization had been predicted according to the sequence of the V3 portion of the env gene (Hung C S et al. (1999); and Briggs D R et al. (2000)). For example, an accumulation of positively charged amino acid located in the V3 domain i.e., at positions 11 and 25 of the V3 domain and is a common feature of X4 viruses (Fouchier R A et al. (1992); Milich L. et al. (1997)). The V3 region of CXCR4-specific viruses also can exhibit greater sequence variation than their R5-specific counterparts, in particular respect with common laboratory HIV isolates at HTLV-IIIB/LAV and JR-CSF (Milich L. et al. (1997)).

The difference in cell tropism correlates with disease progression. Generally, after primary HIV-1 infection, viral populations are usually characterized by molecular heterogeneity. Strains isolated from individuals early in the course of their infection are usually M-tropic (Shankarappa et al. (1999); and Glushakova et al. (1999) J. Clin. Invest. 104:R7-R11). In many cases, the X4 and R5 strains coexist to some extent in the viral swarm or population. For example, viruses isolated from approximately 50% of individuals with advanced immunodeficiency include viruses that are M- and T-tropic. Typically, the emergence of X4 variants is associated with depletion of CD4 cells and acceleration of clinical disease. (See: Berger et al. (1998); Björndal et al. (1997); Shankarappa et al. (1999); Scarlatti et al. (1997); Koot et al. (1993) Ann. Intern. Med. 118:681-688; Connor et al. (1997) J. Exp. Med. 185:621-628; Blaak et al. (2000) Proc. Natl. Acad. Sci. 97:1269-1274). For example, it has been shown that cytopathicity toward the general CD4+ T cell population in lymphoid tissue is associated with the use of CXCR4 (Glushakova et al. (1999)). Additionally, in vitro results suggest that selective blockade of CXCR4 receptors may prevent the switch from the less pathogenic R5 strains to the more pathogenic X4 strains (Este et al. (1999) J. Virol. 73:5577-85).

Current antiretroviral therapies are intended to improve the overall clinical outcome of infected individuals. For example, treatment of infected individuals with combination antiretroviral therapy (cART), formerly called highly active antiretroviral therapy (HAART), has led to a dramatic decline in both HIV-1-related illness and death (Palella et al. (1998) N. Engl. J. Med. 338:853-60; Egger et al. (1997) BMJ 315:1194-9; Ledergerber et al. (1999) 353:863-8; Mocroft et al. (2003) 362:22-9). Early clinical trials demonstrated a reduction of plasma HIV-1 RNA loads to undetectable levels in the majority of treated individuals (Hammer et al. (1997) N. Engl. J. Med. 337:725-33; and Autran et al. (1997) Science 277:112-6). Subsequent studies, however, have showed more limited success. In particular although many patients experience initial immunologic and clinical responses to cART, the suppression of plasma viremia is not always sustained (Deeks et al. (2000); and Mezzaroma et al. (1999)).

cART has been demonstrated to preferentially suppress X4 strains during the first years of therapy, suggesting that shifts in HIV-1 coreceptor usage may contribute to the clinical efficacy of treatment (Philpott et al. (2001) J. Clin. Invest. 107:431-437; Equils, et al. (2000) J. Infect. Dis. 182: 751-757; and Skrabal et al. (2003) AIDS 17:809-814). For example, in comparison to pretherapy determinations, expression of CXCR4 was significantly increased, and CCR5 decreased, following three months of an anti-viral regimen; the changes in coreceptor expression occurred in association with a decrease in viral load and T cell activation, and an increase in naive and memory T cells, suggesting peripheral redistribution of T cell compartments (Giovannetti et al. (1999) Clin. Exp. Immunol. 118:87-94). In another study, cART was reported to reduce the expression of CXCR4 and CCR5 in lymphoid tissue (Andersson et al. (1998) AIDS 12:F123-9). These studies did not address coreceptor usage in patients undergoing HAART. The effects of cART on coreceptor usage by viral populations were heretofore unknown.

In patients undergoing cART, the predominant populations of virus shift back to CCR5-mediated entry after the CXCR4-specific strains emerge. cART may affect either the expression of CCR5 over CXCR4 or, alternatively, it may be influencing the kind of viral variant that predominates, such as CCR5-specific versus CXCR4-specific viruses. There is a correlation between the emergence of CXCR4-specific strains and rapid HIV disease progression.

Because cART is toxic to some patients, costly, and requires life-long adherence, the decision to start treatment in asymptomatic patients is complex, and therefore tailored to the individual (Yeni et al. (2004) JAMA 292:251-65). A small proportion of patients continue to experience disease progression despite cART, and questions remain regarding when to initiate and switch therapies (Egger et al. (1997) Ledergerber et al. (1999); Mocroft et al. (2003); Opravil et al. (2002) AIDS 16:1371-81; Sterling et al. (2003) J. Infect. Dis. 188:1659-65); Anastos et al. (2004) Ann. Intern. Med. 140:256-64; Mezzaroma et al. (1999) Clin. Infect. Dis. 29:1423-30; Deeks et al. (2000) J. Infect. Dis. 181:946-53; and Ledergerber et al. (2004) Lancet 364:51-61). Changing therapy in these patients, particularly after drug resistance or intolerance has developed, is also a challenge.

Currently, the principal measurements guiding therapeutic decisions are CD4 count and plasma HIV-1 RNA, as both are predictors of disease progression and response to cART (Anastos et al. (2004); Yeni et al. (2004); Ledergerber et al. (2004); Kitchen et al. (2001) Clin. Infect. Dis. 33:466-72; Egger et al. (2002) Lancet 360:119-29; and Chene et al. (2003) Lancet 362:679-86). However, debate continues about optimal treatment strategies, highlighting the need for more data to guide clinical management (Holmberg et al. (2004) Clin. Infect. Dis. 39:1699-1704; Miller et al. (2002) J. Infect. Dis. 186:189-197; and Phillips et al. (2003) AIDS 17:1863-1869). In particular, new markers are necessary to identify which patients are at highest risk for clinical disease and therefore most likely to benefit from immediate initiation or change of cART. These patients may be untreated, asymptomatic individuals or those with persistent viremia despite cART.

To accurately predict disease prognosis over time and in response to treatment, a diagnostic method would be useful to monitor the presence (or absence) of CXCR4-specific strains and/or CCR5-specific strains and shifts in coreceptor use over time. A diagnostic method for use in monitoring shifts in coreceptor use may thereby be beneficial for measuring the therapeutic efficacy of various HIV treatment regimes, such as cART. The effect of cART on coreceptor use by populations of virus has not heretofore been quantitatively studied.

The correlation between CXCR4-specific strains and rapid disease progression also indicates that a diagnostic method would be useful to monitor the presence of CXCR4-specific strains, shifts in coreceptor use associated with HIV disease progression, and to monitor the presence of CXCR4-specific strains and shifts in coreceptor use in patients undergoing antiretroviral therapy.

Accordingly, diagnostic methods for use in detecting CXCR4 isolates and/or monitoring shifts in coreceptor use (e.g. shifts from CXCR4-specific HIV to CCR5-specific HIV and vice versa) would be beneficial for predicting disease progression over time or in response to treatment. Moreover, cell-based and molecular-based methods to monitor, measure, evaluate, detect, etc. HIV coreceptor use which are reliable, accurate, and easy to use as well as being qualitative and/or quantitative in their approach would be a welcomed advance to the art.

In particular, diagnostic methods, e.g. cell-based and/or molecular-based methods, for measuring, monitoring, evaluating, detecting, etc. patient-derived HIV samples for coreceptor usage would be beneficial for evaluating HIV disease progression in the face of various anti HIV treatment and therapies.

OBJECTS AND SUMMARY OF THE INVENTION

The present invention relates to diagnostic methods and components thereof for determining the viral load of a population of acquired immunodeficiency virus using the CXCR4 coreceptor (X4-specific viral load) in a patient-derived biological sample. This invention further relates to a method of determining when to initiate antiretroviral therapy in a patient. The present invention also relates to a method of monitoring the efficacy of antiretroviral therapy in a patient.

The present invention encompasses a diagnostic method which may comprise determining the viral load of a population of acquired immunodeficiency (AIDS) virus using the CXCR4 coreceptor (X4-specific viral load) in a patient-derived biological sample comprising the steps of: (a) screening individual molecular clones of patient-derived acquired immunodeficiency primary isolate with a V3 loop sequencing assay to determine CCR5 coreceptor usage and CXCR4 coreceptor usage of each individual molecular clone; (b) determining the proportion of HIV using the CCR5 coreceptor (R5) versus the CXCR4 coreceptor (X4) wherein the proportion is expressed as a variable called the Quantity of X4 and R5 (QXR), which represents the fraction of virus in a specimen using the R5 coreceptor; (c) determining coreceptor specific viral loads of the patient-derived acquired immunodeficiency primary isolate wherein the R5-specific viral load=(VL)(QXR) and the X4-specific viral load=(VL)(1−QXR), wherein X4-specific viral load strongly predicts disease progression during cART.

In a preferred embodiment of the method, the screening of individual molecular clones of patient-derived acquired immunodeficiency primary isolate to determine CCR5 coreceptor usage and CXCR4 coreceptor usage of each individual molecular clone is conducted with a V3 loop sequencing assay.

The present invention further encompasses a diagnostic method which may comprise determining the viral load of a population of acquired immunodeficiency virus using the CXCR4 coreceptor (X4-specific viral load) in a patient-derived biological sample. In one embodiment, the method may comprise the steps of: (a) screening individual molecular clones of patient-derived acquired immunodeficiency primary isolate with a heteroduplex tracking assay to determine the CCR5 coreceptor usage and the CXCR4 coreceptor usage of each individual molecular clone; (b) determining the proportion of HIV using the CCR5 coreceptor (R5) versus the CXCR4 coreceptor (X4) wherein the proportion is expressed as a variable called the Quantity of X4 and R5 (QXR), which represents the fraction of virus in a specimen using the R5 coreceptor; (c) determining coreceptor specific viral loads of the patient-derived acquired immunodeficiency primary isolate wherein the R5-specific viral load=(VL)(QXR) and the X4-specific viral load=(VL)(1−QXR), wherein X4-specific viral load strongly predicts disease progression during cART.

In a preferred embodiment of the method if QXR=1, almost all of the viruses in the population use the R5 coreceptor; if QXR=0, almost all of the viruses in the population use the X4 coreceptor; and if QXR<1, the viruses in the population use a mixture of the R5 and X4 coreceptors.

Preferably, the patient-derived biological sample is any bodily fluid or tissue. In one embodiment, the biological sample may be a bodily fluid which may be selected from the group consisting of blood, plasma, and spinal fluid.

Preferably, the individual molecular clones may each comprise a DNA sequence corresponding to a portion of the HIV genome, the DNA sequence comprising at least a portion of the genetic determinates of coreceptor usage.

In a preferred embodiment, the genetic determinates may be derived from the env gene.

In another preferred embodiment, the molecular clones each may be derived from RNA of the patient-derived HIV and correspond to the HIV genome or a portion thereof and which comprise the genetic determinates of coreceptor usage or a portion thereof. In another preferred embodiment, the molecular clones may be prepared by reverse transcription PCR (RT-PCR) of the RNA of the patient-derived HIV and at least one set of oligonucleotide primers. In a more preferred embodiment, at least one set of oligonucleotide primers may consist of the first set of primers in Table 3. In another more preferred embodiment, at least one set of oligonucleotide primers may include a second set of oligonucleotide primers, consisting of the second set of primers in Table 3. Preferably, the number of individual molecular clones may be at least 20.

In another preferred embodiment, the heteroduplex tracking assay of the method may comprise the steps of: (a) amplifying the individual molecular clone or a portion thereof by PCR to provide amplified DNA comprising the genetic determinates of coreceptor usage or a portion thereof; (b) forming a population of heteroduplex molecules by contacting the amplified DNA with a labeled probe complementary to the amplified DNA under conditions sufficient to form heteroduplexes; (c) separating the population of heteroduplex molecules using a separation means; (d) detecting the presence or absence of heteroduplex molecules; wherein the presence or absence of heteroduplex molecules reveals coreceptor usage. More preferably, the labeled probe may be derived from a known HIV-1 CCR5 clone or from a known HIV-1 CXCR4 clone. In another preferred embodiment, the labeled probe may comprise a detectable moiety, a radioisotope, biotin, a fluorescent moiety, a fluorophore, a chemiluminescent moiety, or an enzymatic moiety.

In another preferred embodiment, the method may be used (a) to assess or predict the degree of HIV progression, (b) to determine when to start or change antiretroviral treatment, or (c) to monitor the efficacy of antiretroviral treatment.

The present invention further encompasses a method of determining when to initiate antiretroviral therapy in a patient which may comprise determining the viral load of a population of acquired immunodeficiency virus using the CXCR4 coreceptor (X4-specific viral load) in a patient-derived biological sample which may comprise the steps of: (a) screening individual molecular clones of patient-derived acquired immunodeficiency primary isolate with a heteroduplex tracking assay to determine the CCR5 coreceptor usage and the CXCR4 coreceptor usage of each individual molecular clone; (b) determining the proportion of EIIV using the CCR5 coreceptor (R5) versus the CXCR4 coreceptor (R4) wherein the proportion is expressed as a variable called the Quantity of X4 and R5 (QXR), which represents the fraction of virus in a specimen using the R5 coreceptor; (c) determining coreceptor specific viral loads of the patient-derived acquired immunodeficiency primary isolate wherein the R5-specific viral load=(VL)(QXR) and the X4-specific viral load=(VL)(1−QXR), and wherein initiation or change of antiretroviral therapy may be considered anytime that the X4-specific viral load is greater than zero.

In a preferred embodiment, if QXR=1, almost all of the viruses in the population use the R5 coreceptor; if QXR=0, almost all of the viruses in the population use the X4 coreceptor; and if QXR<1, the viruses in the population use a mixture of the R5 and X4 coreceptors.

Preferably, the patient-derived biological sample may be any bodily fluid or tissue. In one embodiment, the biological sample may be a bodily fluid which may be selected from the group consisting of blood, plasma, and spinal fluid.

Preferably, the individual molecular clones may each comprise a DNA sequence corresponding to a portion of the HIV genome, the DNA sequence comprising at least a portion of the genetic determinates of coreceptor usage.

In a preferred embodiment, the genetic determinates may be derived from the env gene.

In another preferred embodiment, the molecular clones each may be derived from RNA of the patient-derived HIV and correspond to the HIV genome or a portion thereof and which comprise the genetic determinates of coreceptor usage or a portion thereof. In another preferred embodiment, the molecular clones may be prepared by RT-PCR of the RNA of the patient-derived HIV and at least one set of oligonucleotide primers. In a more preferred embodiment, at least one set of oligonucleotide primers may consist of the first set of primers in Table 3. In another more preferred embodiment, at least one set of oligonucleotide primers may include a second set of oligonucleotide primers, the second set may consist of the second set of primers in Table 3. Preferably, the number of individual molecular clones may be at least 20.

In another preferred embodiment, the heteroduplex tracking assay of the method may comprise the steps of: (a) amplifying the individual molecular clone or a portion thereof by PCR to provide amplified DNA comprising the genetic determinates of coreceptor usage or a portion thereof; (b) forming a population of heteroduplex molecules by contacting the amplified DNA with a labeled probe complementary to the amplified DNA under conditions sufficient to form heteroduplexes; (c) separating the population of heteroduplex molecules using a separation means; (d) detecting the presence or absence of heteroduplex molecules; wherein the presence or absence of heteroduplex molecules reveals coreceptor usage. More preferably, the labeled probe may be derived from a known HIV-1 CCR5 clone or from a known HIV-1 CXCR4 clone. In another preferred embodiment, the labeled probe may comprise a detectable moiety, a radioisotope, biotin, a fluorescent moiety, a fluorophore, a chemiluminescent moiety, or an enzymatic moiety.

In another preferred embodiment, the antiretroviral therapy of the method may be any suitable antiretroviral treatment regimen. More preferably, the antiretroviral therapy may be selected from the group consisting of combination antiretroviral therapy (cART), protease inhibitors, fusion inhibitors, integrase inhibitors, coreceptor specific agents, nonnucleoside analogue reverse transcriptase inhibitors and nucleoside analogue reverse transcriptase inhibitors. Preferably, the nucleoside analoque reverse transcriptase inhibitor may be 3TC or AZT. Preferably, the nonnucleoside analogue reverse transcriptase inhibitor may be nevirapine.

The present invention further encompasses a method of monitoring the efficacy of antiretroviral therapy in a patient which may comprise determining the viral load of a population of acquired immunodeficiency virus using the CXCR4 coreceptor (X4-specific viral load) in a patient-derived biological sample comprising the steps of: (a) screening individual molecular clones of patient-derived acquired immunodeficiency primary isolate with a heteroduplex tracking assay to determine the CCR5 coreceptor usage and the CXCR4 coreceptor usage of each individual molecular clone; (b) determining the proportion of HIV using the CCR5 coreceptor (R5) versus the CXCR4 coreceptor (R4) wherein the proportion is expressed as a variable called the Quantity of $\underline{X}4$ and $\underline{R}5$ (QXR), which represents the fraction of virus in a specimen using the R5 coreceptor; (c) determining coreceptor specific viral loads of the patient-derived acquired immunodeficiency primary isolate wherein the R5-specific viral load=(VL)(QXR) and the X4-specific viral load=(VL)(1−QXR), wherein X4-specific viral load strongly predicts disease progression during cART.

In a preferred embodiment, if QXR=1, almost all of the viruses in the population use the R5 coreceptor; if QXR=0, almost all of the viruses in the population use the X4 coreceptor; and if QXR<1, a the viruses in the population use a mixture of the R5 and X4 coreceptors.

Preferably, the patient-derived biological sample may be any bodily fluid or tissue. In one embodiment, the biological sample may be a bodily fluid which may be selected from the group consisting of blood, plasma, and spinal fluid.

Preferably, the individual molecular clones may each comprise a DNA sequence corresponding to a portion of the HIV genome, the DNA sequence comprising at least a portion of the genetic determinates of coreceptor usage.

In a preferred embodiment, the genetic determinates may be derived from the env gene.

In another preferred embodiment, the molecular clones each may be derived from RNA of the patient-derived HIV and correspond to the HIV genome or a portion thereof and which comprise the genetic determinates of coreceptor usage or a portion thereof. In another preferred embodiment, the molecular clones may be prepared by RT-PCR of the RNA of the patient-derived HIV and at least one set of oligonucleotide primers. In a more preferred embodiment, at least one set of oligonucleotide primers may consist of the first set of primers in Table 3. In another more preferred embodiment, at least one set of oligonucleotide primers may include a second set of oligonucleotide primers, the second set consisting of the second set of primers in Table 3. Preferably, the number of individual molecular clones may be at least 20.

In another preferred embodiment, the heteroduplex tracking assay of the method may comprise the steps of: (a) amplifying the individual molecular clone or a portion thereof by PCR to provide amplified DNA comprising the genetic determinates of coreceptor usage or a portion thereof; (b) forming a population of heteroduplex molecules by contacting the amplified DNA with a labeled probe complementary to the amplified DNA under conditions sufficient to form heteroduplexes; (c) separating the population of heteroduplex molecules using a separation means; (d) detecting the presence or absence of heteroduplex molecules; wherein the presence or absence of heteroduplex molecules reveals coreceptor usage. More preferably, the labeled probe may be derived from a known HIV-1 CCR5 clone or from a known HIV-1 CXCR4 clone. In another preferred embodiment, the labeled probe may comprise a detectable moiety, a radioisotope, biotin, a fluorescent moiety, a fluorophore, a chemiluminescent moiety, or an enzymatic moiety.

In another preferred embodiment, the antiretroviral therapy of the method may be any suitable antiretroviral treatment regimen. More preferably, the antiretroviral therapy may be selected from the group consisting of combination antiretroviral therapy (cART), protease inhibitors, fusion inhibitors, integrase inhibitors, coreceptor specific agents, nonnucleoside analogue reverse transcriptase inhibitors and nucleoside analogue reverse transcriptase inhibitors. Preferably, the nucleoside analoque reverse transcriptase inhibitor may be 3TC or AZT. Preferably, the nonnucleoside analogue reverse transcriptase inhibitor may be nevirapine.

BRIEF DESCRIPTION OF THE FIGURES

The following Detailed Description, given by way of example, but not intended to limit the invention solely to the specific embodiments described, may be best understood in conjunction with the accompanying drawings, in which.

DETAILED DESCRIPTION

Figure 1A:
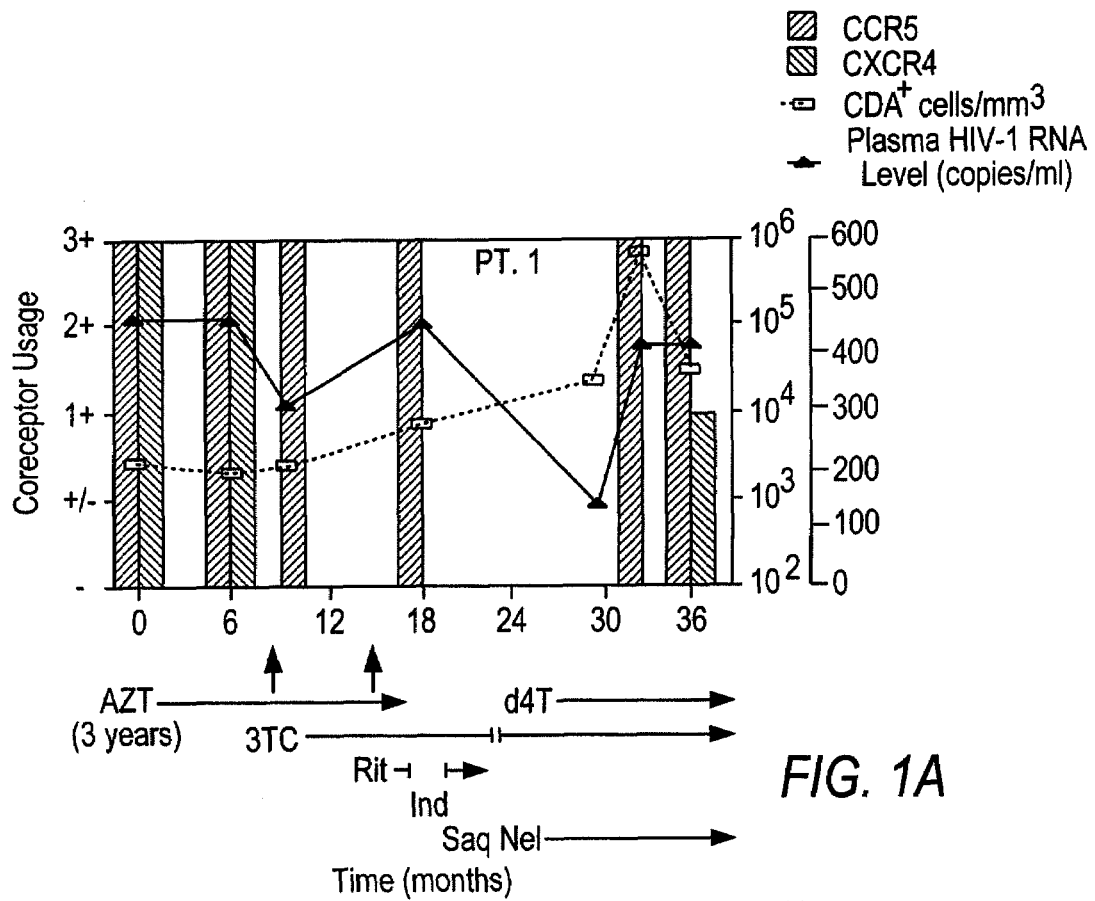
FIG. 1 depicts the effect of combination antiretroviral therapy on HIV-1 coreceptor use over time in representative study subjects. Patients 1, 2, 6, 8, and 10 received new, combination therapy and Patient 13 remained untreated. Arrows note the first time during the study period that a new combination of antiretroviral drugs was initiated. Two arrows appear if a patient received a two drug regimen first, then HAART. The duration of treatment with each agent is indicated. Drugs are abbreviated as follows: AZT, zidovudine; 3TC, lamivudine; Rit, ritonavir; Ind, indinavir; Saq, saquinavir; d4T, stavudine; Nel, nelfinavir; ddI, didanosine; ddC, zalcitabine; and Nev, nevirapine.
Figure 1B:
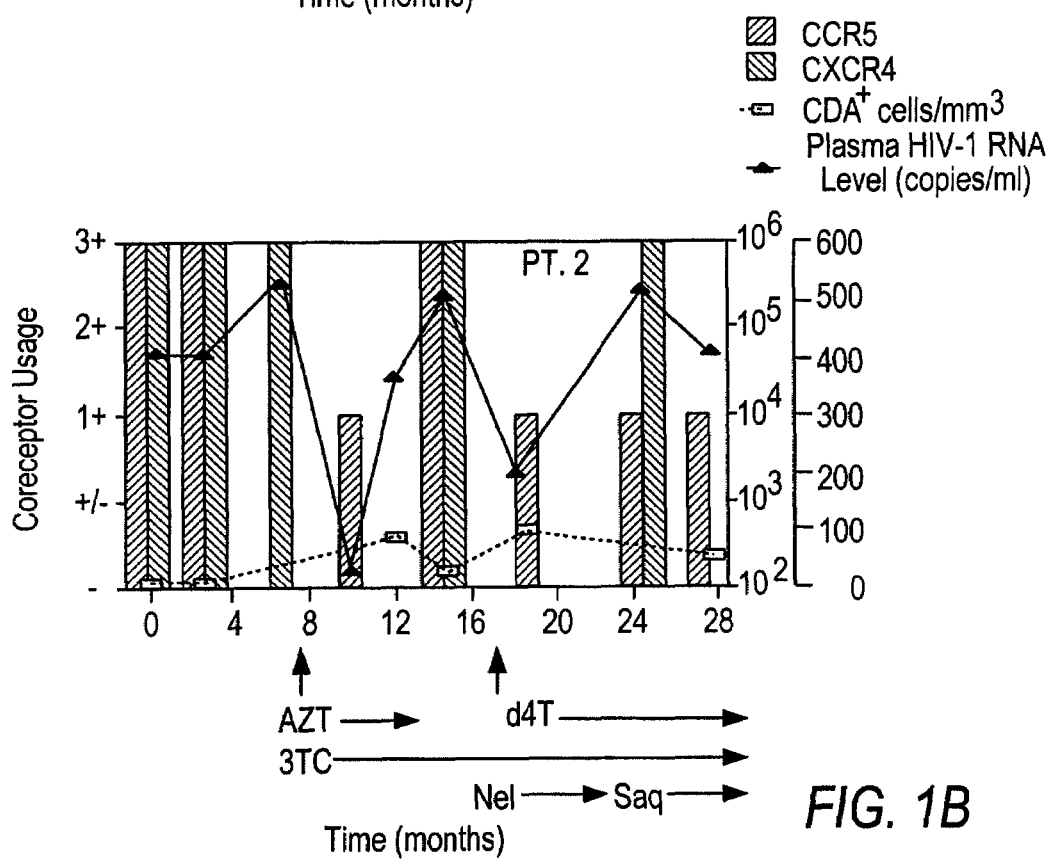
Figure 1C:
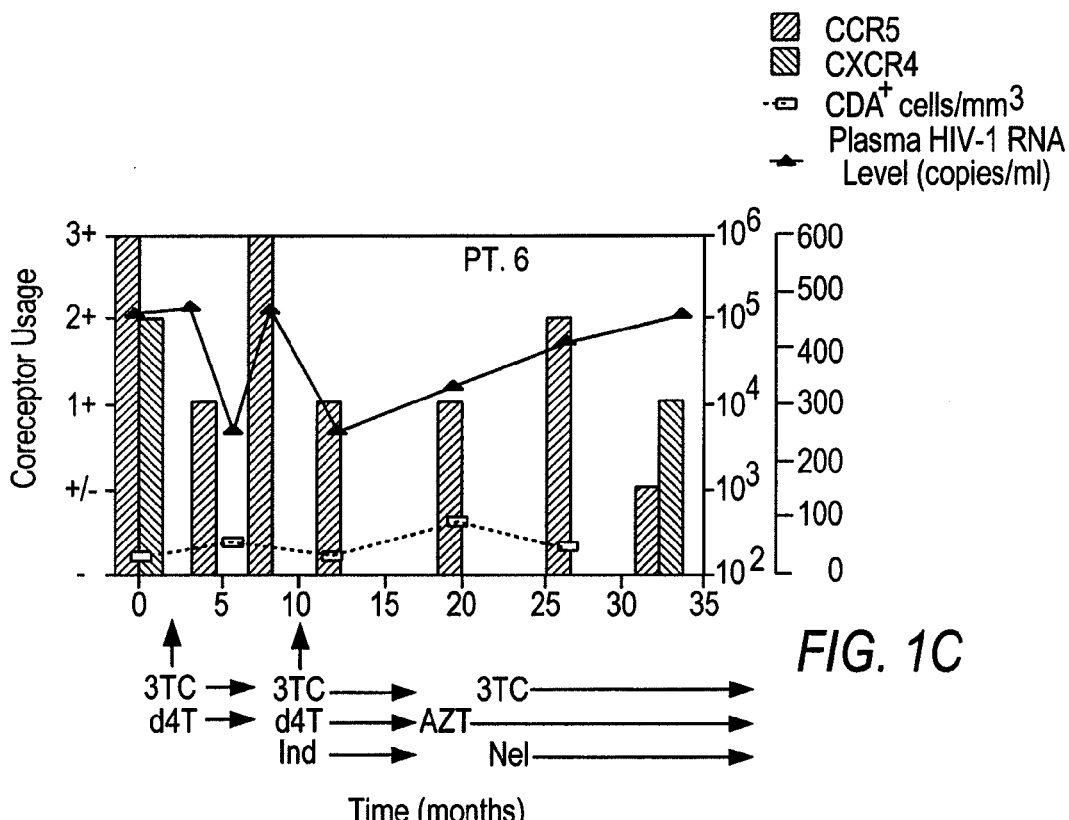
Figure 1D:
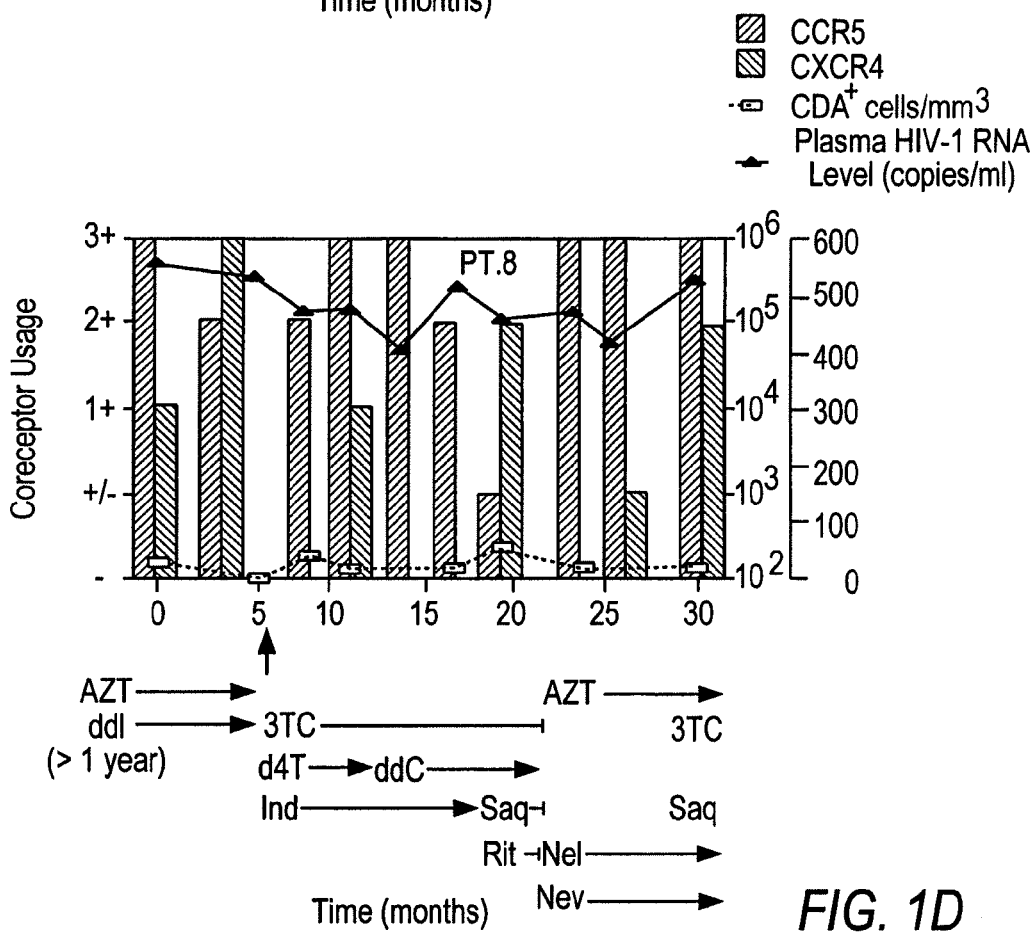
Figure 1E:
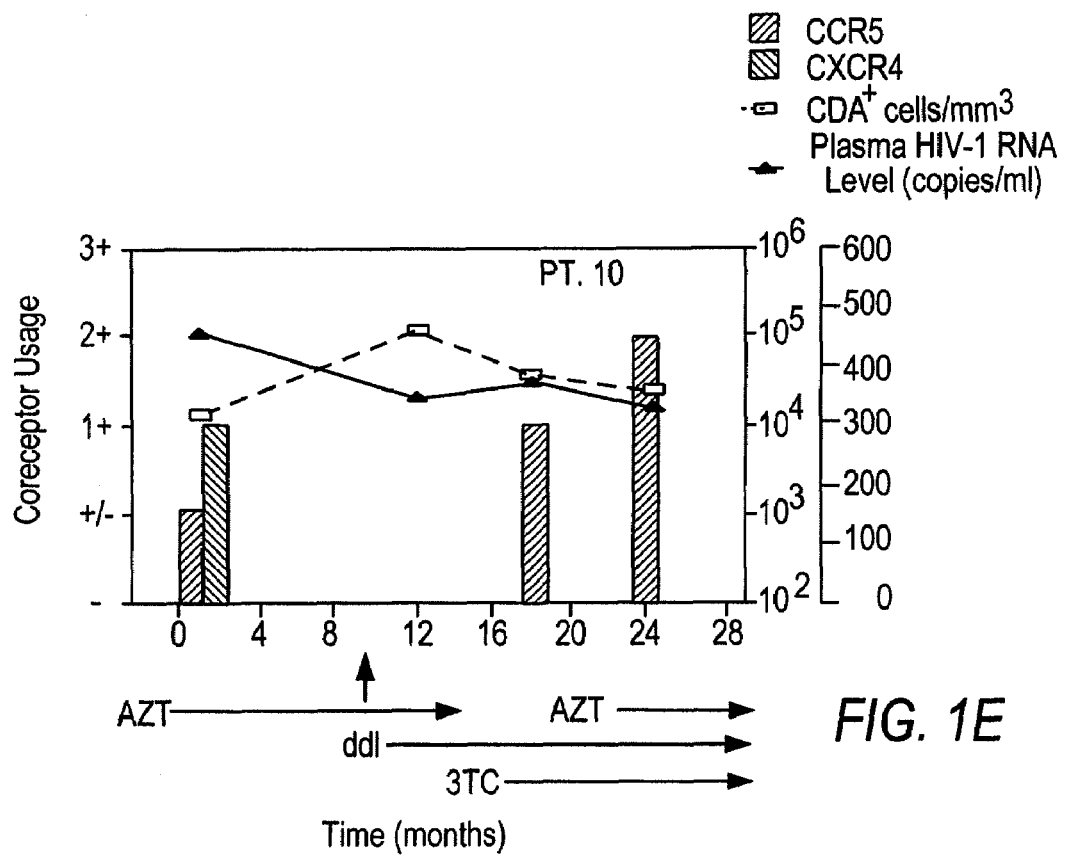
Figure 1F:
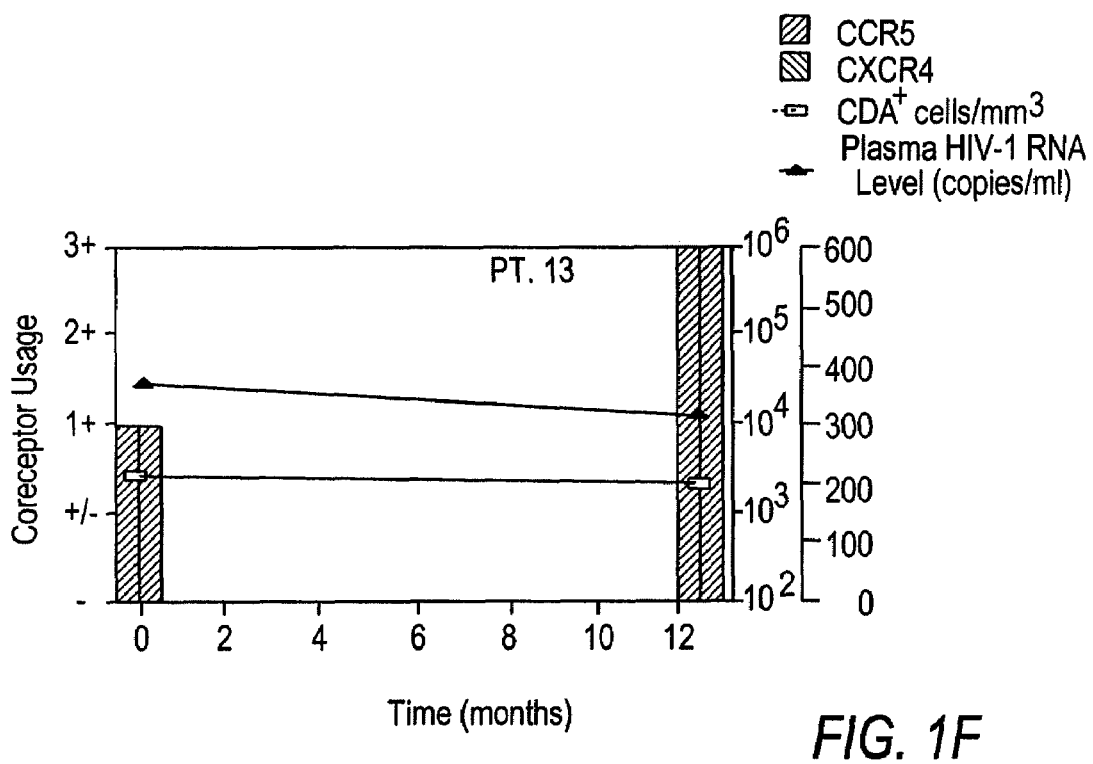

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

The practice of the present invention will employ, unless otherwise indicated, conventional techniques of molecular biology, microbiology, recombinant DNA technology, genetic engineering, polypeptide and nucleic acid synthesis, nucleic acid sequencing, cloning technology, protein/DNA expression technology, and immunology, which are all within the skill of the art. Such techniques are explained fully in the literature. See e.g., Sambrook, et al., MOLECULAR CLONING; A LABORATORY MANUAL, SECOND EDITION (1989); DNA CLONING, VOLUMES I AND II (D. N Glover ed. 1985); OLIGONUCLEOTIDE SYNTHESIS (M. J. Gait ed. 1984); NUCLEIC ACID HYBRIDIZATION (B. D. Hames & S. J. Higgins eds. 1984); TRANSCRIPTION AND TRANSLATION (B. D. Hames & S. J. Higgins eds. 1984); ANIMAL CELL CULTURE (R. I. Freshney ed. 1986); IMMOBILIZED CELLS AND ENZYMES (IRL Press, 1986); B. Perbal, A PRACTICAL GUIDE TO MOLECULAR CLONING (1984); the series, METHODS IN ENZYMOLOGY (Academic Press, Inc.); GENE TRANSFER VECTORS FOR MAMMALIAN CELLS (J. H. Miller and M. P. Calos eds. 1987, Cold Spring Harbor Laboratory), Methods in Enzymology Vol. 154 and Vol. 155 (Wu and Grossman, and Wu, eds., respectively), Mayer and Walker, eds. (1987), IMUNOCHEMICAL METHODS IN CELL AND MOLECULAR BIOLOGY (Academic Press, London), Scopes, (1987), PROTEIN PURIFICATION: PRINCIPLES AND PRACTICE, Second Edition (Springer-Verlag, N.Y.), and HANDBOOK OF EXPERIMENTAL IMMUNOLOGY, VOLUMES I-IV (D. M. Weir and C. C. Blackwell eds 1986), each of which are incorporated herein by reference.

The term "or (a) fragment(s) thereof" as employed in the present invention and in context with polypeptides of the invention, comprises specific peptides, amino acid stretches of the polypeptides as disclosed herein. It is preferred that said "fragment(s) thereof" is/are functional fragment(s). The term "functional fragment" as used herein denotes a part of the above identified polypeptide of the invention which fullfils, at least in part, physiologically and/or structurally related activities of the polypeptide of the invention. It is also envisaged that the fragments, like the full-length polypeptides, may be distinguished between HIV strains in effecting binding. The polypeptides of the present invention can be recombinant polypeptides expressed in eukaryotic cells, like mammalian cells.

The term "nucleic acid hybridization" may be used herein to refer to "molecular-based assays," and may include, for example, the heteroduplex binding assay of the invention. The present invention may also include methods that combine both cell-based and molecular based methods and should not be construed to be limited to either one or the other approach.

The term "molecular clone" may be used herein to refer to the cloning of a portion of the HIV genome, such as a gene or a portion of a gene, which can then be analyzed in accordance with the molecular-based methods of the invention, especially the heteroduplex tracking assay.

The term "genetic determinates" may be used herein to refer to the molecular clones of portions of the env gene which allow a quantitative determination of the proportion of HIV specific for the CCR5 coreceptor and those specific for the CXCR4 coreceptor, for example the third variable (V3) region of the gp120 glycoprotein.

The term "PCR" as used herein refers to the molecular biology technique known as polymerase chain reaction, disclosed by Mullis in U.S. Pat. Nos. 4,683,195 (Mullis et al) and 4,683,202, incorporated herein by reference. The following U.S. Patents may also be referenced for information relating to PCR generally: U.S. Pat. Nos. 6,316,192; 6,309,837; 6,300,073; 6,300,072; 6,284,455; 6,270,977; 6,270,966; 6,268,143; 6,261,431; 6,251,607; 6,232,079; 6,225,093; 6,218,153; 6,207,425; 6,183,963; 6,180,372; 6,146,834; 6,087,097; 6,072,369; 6,068,974; 6,063,563; 6,046,039; 6,031,960; 6,017,699; 6,015,664; 6,015,534; 6,001,612; 5,972,602; 5,909,468; 5,905,732; 5,888,740; 5,883,924; 5,869,318; 5,853,991; 5,837,468; 5,827,657; 5,824,516; 5,824,479; 5,814,489; 5,780,222; 5,776,686; 5,774,497; 5,759,822; 5,716,784; 5,712,125; 5,712,090; 5,691,146; 5,681,741; 5,618,703; 5,618,702; 5,565,340; 5,556,774; 5,556,773; 5,527,510; 5,487,993; 5,426,026; 5,393,657;

5,364,790; 5,364,758; 5,229,297; and 5,187,060; each of which are incorporated herein in their entirety by reference. The term RT-PCR refers to reverse transcription of an RNA molecule to a complementary DNA (cDNA) molecule, followed by PCR of that cDNA.

The term "patient" as used herein may be any animal, preferably a mammal, and even more preferably a human, infected with HIV.

The term "acquired immunodeficiency virus" as used herein refers to the infectious AIDS virus known to one of skill in the art and may be, but is not limited to, HIV-1 and/or HIV-2.

The term "genotype" may be used herein to refer to a strain of HIV at the genetic sequence level. One of skill in the art appreciates that during the course of disease progression the pool of HIV in an infected individual may become a mixture of different strains which are different at the genetic level (i.e. have different "genotypes"). It is further understood by the skilled person that whether any particular strain of HIV from a population of virus in an infected individual is specific for CCR5 coreceptor or the CXCR4 coreceptor is dependent on the genetic determinates contained in that virus's genome, i.e. is reflected in that virus's genotype.

The term "HAART" as used herein refers to any highly active antiretroviral therapy and is more recently referred to as combination antiretroviral therapy, or "cART", used interchangeably herein with "CART". HAART and cART are also used herein interchangeably. HAART may refer to three or more antiretroviral drugs in combination, and usually comprises one protease inhibitor and two or three reverse transcriptase inhibitors.

Methods for sequencing and/or identifying the V3 region may be any desired method, e.g., a method which is by or analogous to the methods cited in U.S. Pat. Nos. 7,160,992; 7,157,225; 7,122,646; 7,118,874; 7,118,751; 7,097,970; 7,097,965; 7,090,848; 7,067,117; 7,063,943; 7,063,849; 7,041,441; 7,037,896; 7,030,234; 7,022,814; 7,018,835; 7,018,633; 6,995,008; 6,989,435; 6,974,866; 6,964,763; 6,955,900; 6,942,852; 6,930,174; 6,926,898; 6,923,970; 6,919,319; 6,916,605; 6,908,734; 6,908,617; 6,908,612; 6,897,301; 6,887,977; 6,884,623; 6,881,828; 6,875,737; 6,869,925; 6,855,804; 6,855,539; 6,855,528; 6,855,321; 6,849,261; 6,821,955; 6,812,026; 6,808,877; 6,806,079; 6,806,055; 6,800,447; 6,797,811; 6,773,915; 6,740,747; 6,740,525; 6,737,521; 6,737,267; 6,727,060; 6,713,286; 6,709,828; 6,696,289; 6,692,938; 6,686,333; 6,660,271; 6,649,735; 6,649,409; 6,627,197; 6,623,940; 6,613,563; 6,610,542; 6,602,705; 6,600,012; 6,596,279; 6,592,872; 6,569,418; 6,562,347; 6,551,824; 6,548,636; 6,548,635; 6,548,631; 6,544,752; 6,544,527; 6,534,312; 6,531,587; 6,531,137; 6,528,626; 6,525,173; 6,521,739; 6,518,030; 6,511,801; 6,509,018; 6,506,554; 6,503,732; 6,493,637; 6,492,123; 6,492,110; 6,482,919; 6,475,492; 6,455,314; 6,451,322; 6,451,313; 6,448,375; 6,448,070; 6,432,675; 6,428,970; 6,420,545; 6,410,326; 6,410,318; 6,399,294; 6,395,275; 6,392,029; 6,372,425; 6,355,785; 6,355,247; 6,342,228; 6,331,404; 6,329,202; 6,329,147; 6,323,185; 6,319,503; 6,303,292; 6,294,654; 6,291,650; 6,291,157; 6,288,042; 6,277,561; 6,261,558; 6,258,932; 6,235,714; 6,225,447; 6,214,540; 6,187,748; 6,187,310; 6,177,549; 6,172,197; 6,168,784; 6,162,631; 6,156,541; 6,143,876; 6,133,029; 6,132,992; 6,120,992; 6,114,115; 6,110,465; 6,080,408; 6,060,064; 6,057,102; 6,042,832; 6,034,223; 6,025,125; 6,020,468; 6,017,880; 6,015,661; 6,010,895; 5,980,899; 5,977,318; 5,969,109; 5,969,108; 5,968,815; 5,968,510; 5,965,532; 5,962,311; 5,955,647; 5,955,342; 5,925,7411; 5,919,462; 5,912,338; 5,889,176; 5,885,796; 5,885,580; 5,885,579; 5,879,925; 5,871,907; 5,866,320; 5,866,137; 5,863,542; 5,858,657; 5,858,366; 5,856,185; 5,852,186; 5,851,795; 5,849,475; 5,844,095; 5,843,634; 5,840,480; 5,840,300; 5,837,242; 5,827,666; 5,817,316; 5,807,979; 5,804,440; 5,798,205; 5,786,199; 5,770,427; 5,766,845; 5,766,599; 5,766,598; 5,763,574; 5,762,938; 5,759,770; 5,756,674; 5,756,312; 5,756,103; 5,744,144; 5,733,760; 5,728,520; 5,714,374; 5,693,752; 5,693,325; 5,670,153; 5,670,152; 5,667,782; 5,658,779; 5,652,144; 5,652,138; 5,637,481; 5,607,847; 5,591,823; 5,580,773; 5,565,332; 5,541,100; 5,534,257; 5,494,807; 5,443,828.

The sequence variation of the V3 loop may be detected by performing any nucleic acid analysis techniques known to those of skill in the art. Some examples of suitable techniques include sequencing techniques (direct DNA sequencing which is also known as population-based sequencing (using either the dideoxy chain termination method or the Maxam-Gilbert method (see Sambrook et al., Molecular Cloning, A Laboratory Manual (2nd Ed., CSHP, New York 1989); Zyskind et al., Recombinant DNA Laboratory Manual, (Acad. Press, 1988)), sequencing of single variants), pyrosequencing, gel electrophoresis sequencing), hybridization (heteroduplex tracking assay, line probe assay, nucleic acid arrays (details on the use of nucleic acid arrays (DNA chips) for the detection of, for example, SNPs, see U.S. Pat. No. 6,300,063 issued to Lipshultz, et al., and U.S. Pat. No. 5,837,832 to Chee, et al.), bead array).

Other nucleic acid analysis techniques include restriction fragment length polymorphism analysis, cleavase fragment length polymorphism analysis as described in U.S. Pat. No. 5,843,669, random amplified polymorphic DNA (RAPD) analysis, arbitrary fragment length polymorphisms (AFLPs), differential sequencing with mass spectrometry, single based extension (SBE) of a fluorescently-labeled primer coupled with fluorescence resonance energy transfer (FRET) between the label of the added base and the label of the primer as described by Chen et al., (PNAS 94:10756-61 (1997), single-strand conformation polymorphism analysis as described in Orita et al., Proc. Nat. Acad. Sci. 86, 2766-2770 (1989), denaturing gradient gel electrophoresis wherein amplification products generated using PCR can be analyzed by the use of denaturing gradient gel electrophoresis based on the different sequence-dependent melting properties and electrophoretic migration of DNA in solution. Erlich, ed., PCR Technology. Principles and Applications for DNA Amplification, (W.H. Freeman and Co, New York, 1992), Chapter 7.

Optionally, high throughput analysis may be achieved by PCR multiplexing techniques well known in the art. (E.g., Z. Lin et al., Multiplex genotype determination at a large number of gene loci, Proc. Natl. Acad. Sci. USA 93(6):2582-87 [1996]).

Optionally, additional methodologies may be achieved by combining existing nucleic acid analysis methodologies. An example is ultradeep sequencing wherein a two stage PCR technique coupled with a novel pyrophosphate sequencing technique would allow the detection of sequence variants (SNP, indels and other DNA polymorphisms) in a rapid, reliable, and cost effective manner.

Conformation-sensitive gel electrophoresis of amplification products may also be used to analyze sequence variation of the V3 loop. (A. Markoff et al., Comparison of conformation-sensitive gel electrophoresis and single strand conformation polymorphism analysis for detection of mutations in the BRCA1 gene using optimized conformation analysis protocols, Eur. J. Genet. 6(2):145-50 [1998]). The sequence variation of the V3 loop may also be detected by performing immunological analysis techniques known to those of skill in the art such as ELISA and protein arrays. The structure of the V3 loop helps to determine HIV coreceptor usage, and therefore methods that characterize V3 structure may also be used to determine whether a viral variant uses CCR5 or CXCR4 (T. Cardozo et al, Structural basis for coreceptor selectivity by the HIV-1 V3 loop. 2007 *AIDS Res and Hum Retroviruses*; in press).

One ordinarily skilled in the art would acknowledge that there are a number of additional methods that may be employed for analyzing sequence variation aside from the preferred methods described herein. The present invention encompasses the following non-limiting types of sequence variation analysis assays: PCR-free genotyping methods, single-step homogeneous methods, homogeneous detection with fluorescence polarization, "Tag" based DNA chip system, fluorescent dye chemistry, TaqMan genotype assays, Invader genotype assays, and microfluidic genotype assays, among others.

The authors of the present invention have surprisingly found that the viral load of acquired immunodeficiency virus in a patient-derived biological sample using the CXCR4 coreceptor (X4-specific viral load) is directly related to disease progression and clinical outcome. The data presented herein strongly suggest that the X4-specific viral load determined by the methods provided herein is a powerful predictor in guiding clinical therapies including when to initiate antiretroviral therapy, the response to antiretroviral therapies, and clinical management.

The present invention relates to diagnostic methods and components thereof for determining the viral load of a population of acquired immunodeficiency virus using the CXCR4 coreceptor in a patient-derived biological sample. The invention further relates to a method of determining when to initiate antiretroviral therapy in a patient. The present invention also relates to a method of monitoring the efficacy of antiretroviral therapy in a patient.

The present invention encompasses a diagnostic method which may comprise determining the viral load of a population of acquired immunodeficiency virus using the CXCR4 coreceptor (X4-specific viral load) in a patient-derived biological sample. In one embodiment, the method comprises the steps of: (a) screening individual molecular clones of patient-derived acquired immunodeficiency primary isolate with a heteroduplex tracking assay to determine the CCR5 coreceptor usage and the CXCR4 coreceptor usage of each individual molecular clone; (b) determining the proportion of HIV using the CCR5 coreceptor (R5) versus the CXCR4 coreceptor (R4) wherein the proportion is expressed as a variable called the Quantity of X4 and R5 (QXR), which represents the fraction of virus in a specimen using the R5 coreceptor; (c) determining coreceptor specific viral loads of the patient-derived acquired immunodeficiency primary isolate wherein the R5-specific viral load+(VL)(QXR) and the X4-specific viral load=(VL)(1−QXR).

In a preferred embodiment of the method if QXR=1, almost all of the viruses in the population use the R5 coreceptor; if QXR=0, almost all of the viruses in the population use the X4 coreceptor; and if QXR<1, the viruses in the population use a mixture of the R5 and X4 coreceptors.

Preferably, the patient-derived biological sample is any bodily fluid or tissue. In one embodiment, the biological sample may be a bodily fluid which may be selected from the group consisting of blood, plasma, and spinal fluid. In another embodiment, the biological sample may be one which contains viral populations that are distinct from those in the readily obtained peripheral blood including the reservoirs of the genital tract and lymphoid tissue.

Patient-derived biological samples may be obtained by methods known to one of skill in the art. For instance, peripheral blood of HIV-infected individuals can be separated into plasma and cell components by methods known in the art. Primary viral isolates of HIV-1 may also be obtained by co-culture with normal donor peripheral blood mononuclear cells (PBMCs). Titration of viral isolates in PBMCs can be carried out. These standard techniques are described throughout the literature; for example, see Fang et al. (1995) Proc. Natl. Acad. Sci. USA 92:12110-4

Preferably, the individual PCR products or molecular clones each comprise a DNA sequence corresponding to a portion of the HIV genome, the DNA sequence comprising at least a portion of the genetic determinates of coreceptor usage.

In a preferred embodiment, the genetic determinates are derived from the env gene. The envelope protein may comprise gp 120, gp 160 or a portion thereof. Envelope sequences are predictive of coreceptor use on the basis of the overall charge of the V3 loop and the presence of basic or acidic residues at positions 275 and 287 of the env gene (Bhattacharya et al. (1996) AIDS Res. Hum. Retrovir. 12:83-90; Hung et al. (1999) J. Virol. 73:8216-26); and Cardozo et al. (2007) AIDS Res. Hum. Retrov., In press.

Cloning strategies for isolating envelope genes of interest are well known to one of skill in the art. See, for example, Sambrook, Fritsch and Maniatis, Molecular Cloning, A Laboratory Manual, $2^{nd}$ Ed., Cold Spring Harbor Laboratory Press, 1989.

Preferably, the cloning methods used in the present invention will decrease the chance of sampling error or recombination. For example, high fidelity cloning of the samples above may be achieved by routine performance of multiple long RT-PCR reactions on limiting dilutions of RNA, followed by multiple PCR's on cDNAs obtained from each RT reaction. In addition, performance of multiple PCR's on each cDNA preparation increases the likelihood of amplifying a different HIV-1 RNA species. Short-term limited dilution techniques are also well known to one of skill in the art, see for example, Connor et al. (1997). Furthermore, quantitation of HIV-1 RNA in the biological samples of the methods described herein may be carried out, for example, by using NucliSens (Organon Teknika Corp., Durham, N.C.). Quantitation methods may set outer limits. In a preferred embodiment, RNA is amplified to ≦80 copies/ml.

In a preferred embodiment of the invention, the molecular clones each are derived from RNA of the patient-derived HIV and correspond to the HIV genome or a portion thereof and which comprise the genetic determinates of coreceptor usage or a portion thereof. In another preferred embodiment, the molecular clones are prepared by RT-PCR of the RNA of the patient-derived HIV and at least one set of oligonucleotide primers. In a more preferred embodiment, at least one set of oligonucleotide primers consists of the first set of primers in Table 3. In another more preferred embodiment, at least one set of oligonucleotide primers includes a second set of oligonucleotide primers, the second set consisting of the second set of primers in Table 3. Preferably, the number of individual molecular clones is at least 20.

In a preferred embodiment, the heteroduplex tracking assay of the method may comprise the steps of: (a) amplifying the individual molecular clone or a portion thereof by PCR to provide amplified DNA comprising the genetic determinates of coreceptor usage or a portion thereof; (b) forming a population of heteroduplex molecules by contacting the amplified DNA with a labeled probe complementary to the amplified DNA under conditions sufficient to form heteroduplexes; (c)

separating the population of heteroduplex molecules using a separation means; (d) detecting the presence or absence of heteroduplex molecules; wherein the presence or absence of heteroduplex molecules reveals particular coreceptor usage. More preferably, the labeled probe may be derived from a known HIV-1 CCR5 clone or from a known HIV-1 CXCR4 clone. In another preferred embodiment, the labeled probe comprises a detectable moiety, a radioisotope, biotin, a fluorescent moiety, a fluorophore, a chemiluminescent moiety, or an enzymatic moiety.

The heteroduplex tracking assay of the invention can be carried out substantially in accordance with the guidance of Delwart et al. (J. Virol. (1994) 68:6672-6683), Delwart et al. (Science (1993) 262:1257-1261), Nelson et al. (J. Virol. (1997) 71:8850-8, Delwart et al. (PCR Methods and Applications 4:S202-S216 (19950 Cold Springs Harbor), and U.S. Pat. No. 5,851,759 (Weiner), each of which are incorporated in their entireties by reference.

The heteroduplex tracking assay can be used to analyze a portion of the HIV-1 genome encompassing determinates of coreceptor utilization to understand, determine, monitor, or detect coreceptor usage. Genetic determinates of HIV-1 coreceptor utilization can be found in the envelope gene (env), with key determinates being found in the third variable (V3) domain of the gp120 glycoprotein.

The heteroduplex tracking assay of the invention can be carried out generally, while not being limited thereto, according to the basic steps of: (a) obtaining HIV viral RNA from the patient, (b) amplifying, e.g. PCR and/or reverse transcription (RT-PCR), a portion of the viral genome containing genetic determinates of coreceptor usage, e.g. a genomic portion comprising the V3 domain of the gp120 envelope glycoprotein, (c) forming heteroduplexes and/or homoduplexes with labeled nucleic acid-based probes prepared from a corresponding genomic region of a known HIV strain, e.g. the same genomic portion comprising the V3 domain of gp120, and (d) subjecting the heteroduplexes and homoduplexes to a separation system, e.g. electrophoresis through non-denaturing polyacrylamide gels, wherein the heteroduplexes and homoduplexes have differing and distinguishable mobilities that results in different mobility patterns, e.g. a electrophoretic pattern, such that the coreceptor usage can be determined.

For example, the presence of an electrophoretic pattern characteristic of X4-heteroduplexes can indicate the presence of CXCR4-specific viruses in the HIV sample. Alternately, the presence of an electrophoretic pattern characteristic of homoduplexes and R5-heteroduplexes can indicate the presence of only CCR5-specific viruses. And, a pattern characteristic of both homoduplexes and X4- and R5-heteroduplexes can indicate that the HIV sample contains a mixed population of CCR5-specific and CXCR4-specific viruses. The heteroduplex tracking assay can be performed at any point during disease progression or during, before, or after administering antiretroviral therapy. Further, the heteroduplex tracking assay can be carried out either to attain qualitative results or quantitative results.

Methods for obtaining and/or extracting HIV RNA from patient-derived samples are well-known. Also, the step of amplifying a portion of the viral genome containing genetic determinates of coreceptor usage a known in the art, and include, for example reverse transcription PCR (RT-PCR). Following RT-PCT, further rounds of PCR can be used to further amplify desired portions of the genome, especially regions containing genetic determinates of coreceptor usage.

It will be appreciated that the heteroduplex tracking assay is based on the observation that when sequences were amplified by nested PCR from peripheral blood mononuclear cells of infected individuals, related DNA products coamplified from divergent templates could randomly reanneal to form heteroduplexes that migrate with reduced mobility in neutral polyacrylamide gels. Using these techniques, one can establish genetic relationships between multiple viral DNA template molecules, such as the different genetic types (i.e. different genotypes) of HIV utilizing the different coreceptors. The HTA of the invention can be described as utilizing a first PCR product as a labeled probe, e.g. radioactive, or nonradioactive which is mixed with an excess ("driver") of an unlabeled PCR product from a different source, i.e., the source for which typing or analysis of is desired, e.g. the PCR product defining the portion of the HIV genome with the coreceptor genetic determinates. The probe sequences are then "driven" completely into heteroduplexes with the driver, and are separated, e.g. by gel electrophoresis, on the basis of size. An autoradiogram or fluoroimage, for example, of the resulting polyacrylamide gel reveals these heteroduplexes and provides a visual display of the relationship between the two virus populations under study. The fact that heteroduplexes migrate with distinct mobilities indicates that the strand-specific composition of mismatched and unpaired nucleotides affects their mobility.

A "heteroduplex" encompasses a double stranded DNA molecule having complementary strands at which one strand (the "target strand", i.e. a single strand of DNA from the PCR product of the HIV genome) contains one or more mismatched or an unpaired nucleotide base. For example, a heteroduplex can form by mixing together a labeled probe (e.g. a double-stranded DNA PCR product of a portion of the env gene of CCR5-specific HIV) and a PCR product of a target sequence (e.g. a double-stranded DNA PCR product of the corresponding portion of the env gene of a CXCR4-specific HIV) such that complementary single-stranded DNA of each PCR product are combined together as a new, double-stranded molecule. However, since the PCR product from the CXCR4-specific HIV will contain genetic determinates characteristic of CXCR4 type viruses, its nucleotide sequence will vary at specific locations with respect to the probe PCR product (which is derived from CCR5). These differences in sequence result in a heteroduplex which has reduced mobility during electrophoresis with respect to homoduplexes owing to a reduced level of base-pairing in the molecule. In contrast, the "homoduplex" may be formed between complementary strand pairs derived from a probe PCR product and a target PCR product such that their nucleotide sequences are the same.

In another embodiment, the heteroduplex tracking assay can comprise the steps of (a) amplifying an individual molecular clone or a portion thereof by PCR to provide amplified DNA comprising the genetic determinates of coreceptor usage or a portion thereof; (b) forming a population of heteroduplex molecules by contacting the amplified DNA with a labeled probe complementary to the amplified DNA under conditions sufficient to form heteroduplexes; (c) separating the population of heteroduplex molecules using a separation means: and (d) detecting the presence or absence of heteroduplex molecules; wherein the presence or absence of heteroduplex molecules reveals coreceptor usage. In one embodiment, the labeled probe may be derived from a known HIV-1 CCR5 clone. In another embodiment, the labeled probe may be derived from a known HIV-1 CXCR4 clone. The labeled probe can comprise a detectable moiety, a radioisotope, biotin, a fluorescent moiety, a fluorophore, a chemiluminescent moiety, or an enzymatic moiety. Appropriate labels and their methods of preparation are well-known.

It is furthermore envisaged that the diagnostic method may involve the use of micro-chips comprising nucleic acid molecules encoding a envelope protein, or a fragment thereof, preferably a V3 region fragment, especially including genetic determinates of coreceptor usage, on gene chips; or an envelope protein, or a fragment thereof, preferably a V3 region fragment, on protein-chips (See U.S. Pat. Nos. 6,066,454; 6,045,996; 6,043,080; 6,040,193; 6,040,138; 6,033,860; 6,033,850; 6,025,601; 6,022,963; 6,013,440; 5,968,740; 5,925,525; 5,922,591; 5,919,523; 5,889,165; 5,885,837; 5,874,219; 5,858,659; 5,856,174; 5,856,101; 5,843,655; 5,837,832; 5,834,758; 5,831,070; 5,770,722; 5,770,456; 5,753,788; 5,744,305; 5,733,729; 5,710,000; 5,631,734; 5,599,695; 5,593,839; 5,578,832; and 5,556,752). Diagnostic gene chips may comprise a collection of polypeptides that specifically detect a envelope protein, or fragments thereof, preferably V3 region fragments; or nucleic acid molecules that specifically detect a nucleic acid molecule encoding a envelope protein, or fragments thereof, preferably V3 region fragments; all of which may be used for the purposes of determining coreceptor use. The envelope protein may be gp160, gp 120, or a portion thereof.

It will be understood that the heteroduplex tracking assay of the invention can be used to provide both qualitative and quantitative information. First, qualitative information can be derived using the HTA of the invention by analyzing the whole HIV population derived from an infected patient to determine whether the isolated population of HIV is CCR5-specific, CXCR4-specific, or mixture of both types. It will be appreciated that qualitative information is based on the whole or substantially the whole HIV population rather than individual clones therefrom. On the contrary, quantitative information can be derived using the HTA of the present invention by analyzing individual HIV clones (e.g. cloned portions of the HIV genome of a plurality of individual HIV viruses from the isolated whole population of HIV from the infected patient) with respect to their coreceptor usage and determining a ratio of CCR5-specific to CXCR4-specific clones. In one embodiment, the invention relates to determining the QXR ratio: the number of HIV clones that are identified as CCR5-specific compared to the total number of clones analyzed. It will be appreciated that the HIV clone can refer to the cloned PCR product. The quantitative HTA is performed by using clones. A qualitative HTA is performed before a quantitiative HTA is done; the qualitative HTA is performed on the PCR-amplified portion of the HIV genome and which contains genetic determinates of the coreceptor preference. A qualitative HTA yields a QXR with a result of QXR=1, or QXR<1; a quantitative HTA provides a numerical measure of QXR when QXR<1.

Figure 5:
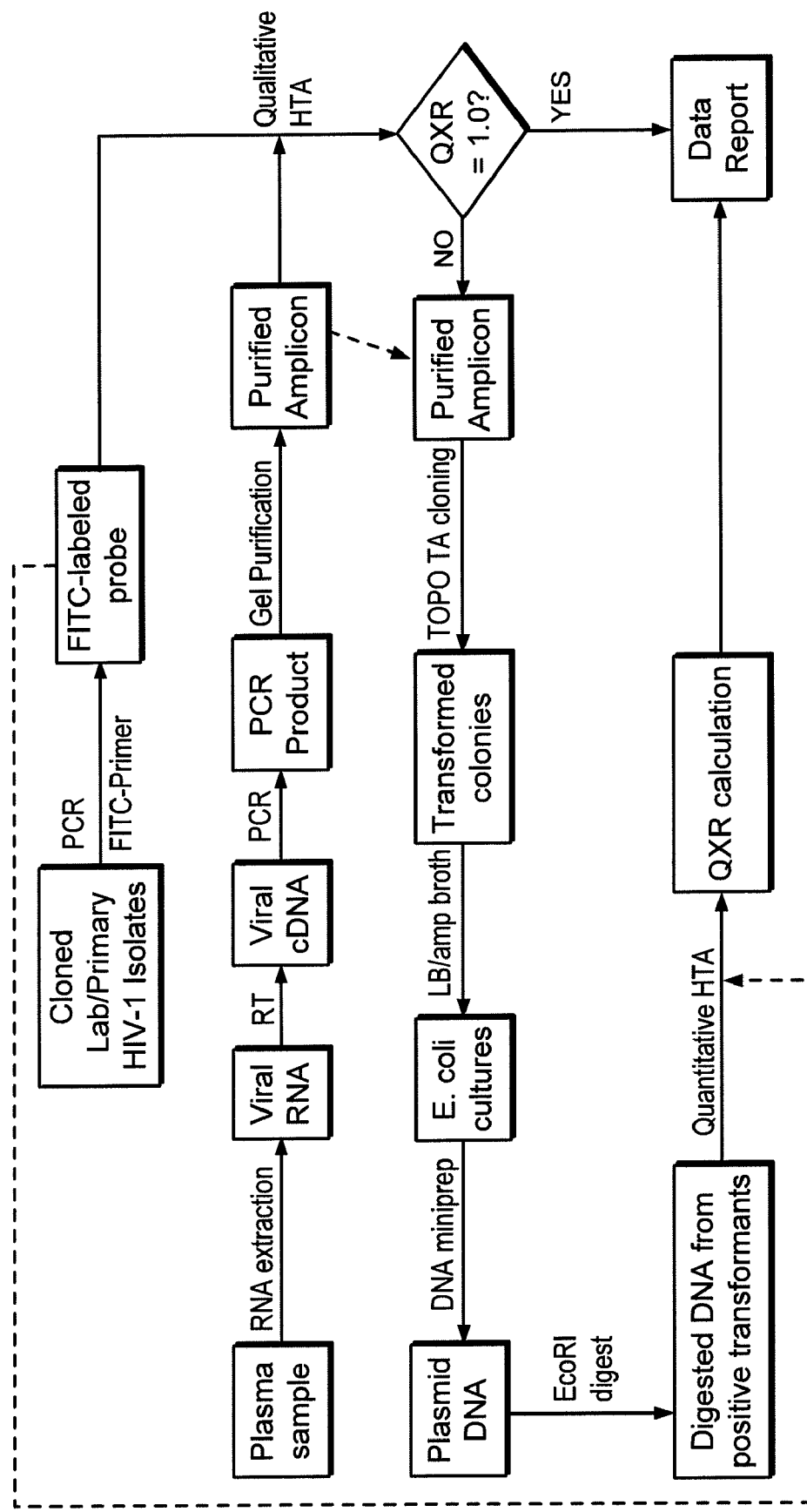
FIG. 5 provides a graphical illustration of the various steps of the heteroduplex tracking assay (HTA) of the invention which provides for both qualitative and quantitative analysis of HIV coreceptor usage.

FIG. 5 depicts a flow chart showing the qualitative and quantitative aspects of the HTA of the present invention. First, HIV RNA is extracted from the infected patient. Next, RT-PCR is carried out to obtain HIV cDNA, from which a PCR product (i.e. PCR amplicon) containing genetic determinates for coreceptor usage is amplied using PCR. The PCR product is then gel purified. Presumably, the PCR product will be a mixed population of molecules—those genotypic for either CCR5 or CXCR4 coreceptors—whenever the isolated HIV sample contains both types of viruses. Next, the PCR product is analyzed by the HTA of the invention, which includes generally the steps of mixing together a labeled probe (e.g. a PCR product corresponding to same region in a known CCR5 strain as the amplified target PCR amplicon to be analyzed) and the amplified target PCR amplicon to form homo- or heteroduplexes. The molecules are then separated by gel electrophoresis, for example, on a 12% polyacrylamide gel. Electrophetic techniques are well known in the art. If the QXR<1 on the qualitative test, then a quantitative test can be done. To perform the quantitative test, the V3 portion of the HIV envelope gene is molecularly cloned and each of 20 clones is analyzed by an individual HTA.

Figure 6:
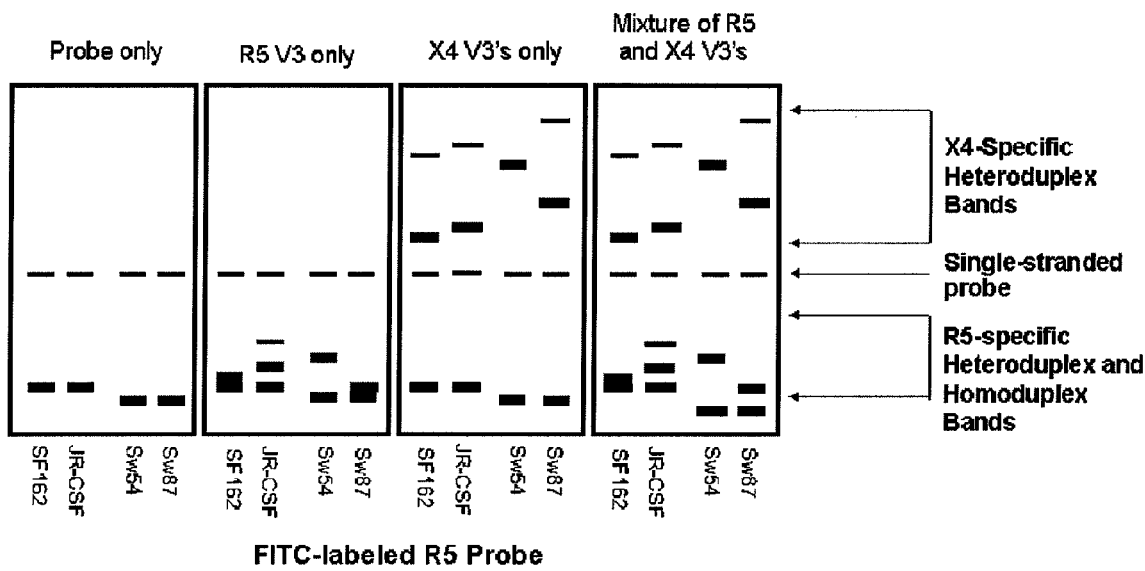
FIG. 6 provides a schematic representation of heteroduplex tracking assay (HTA) analysis of four different targets, including probe only, CCR5-specific HIV V3 region only, CXCR4-specific HIV V3 region only, and a mixture or "quasispecies" of both CCR5-specific and CXCR4-specific HIV V3 regions.

Exemplarly results are represented in FIG. 6. The figures shows four panels of schematic electropherograms. The first panel is the negative control, i.e. labeled probe only. The second panel shows the result of HTA of the V3 portion of the HIV envelope gene of a CCR5 virus. The third panel shows the result of HTA of the V3 portion of the HIV envelope gene of a CXCR4 virus. And, the fourth panel shows the result of HTA of a mixture of CCR5 and CXCR4 virus V3 regions. Four different probes (each based on a CCR5-specific control virus) were used to test each HIV sample. The gels show heteroduplex band patterns for those HIV samples containing CXCR4-specific and CCR5-specific viruses.

The quantitative results of the heteroduplex tracking assay of the method of the present invention may be assessed by statistical methods well known to one of skill in the art. For example, QXR, the proportion of plasma HIV-1 using CCR5, may be stratified into two categories: QXR=1 if all virus identified uses CCR5, and QXR<1 if X4 virus is detected. The association between virologic responses and baseline QXR may be assessed by comparing the percentages of patients with undetectable HIV-1 RNA load across the different strata by using, for example, Fischer's exact test. Further, immunologic responses across two strata may be compared by Wilcoxon rank-sum tests. Kaplan-Meier curves and Cox proportional hazard regression models may be applied to quantify the association of baseline or follow-up QXR (equal 1 versus less than 1) with subsequent clinical progression, defined as a new clinical AIDS-defining event or death.

The quantitative results of the heteroduplex tracking assay of the method of the present invention may further be assessed by other statistical methods well known to one of skill in the art. For example, an additional model analyzing the relationship of X4 viral load to HIV-1 disease progression may be included by stratifying the X4-specific viral load into three strata: patients without detectable X4-specific viral load (i.e., QXR=1) and patients with detectable X4 viraemia below and above the median value of X4-specific viral loads, respectively. To compare the predictive capacity with the established progression markers CD4 and HIV-1 RNA load the concurrent $\log_2$ transformed CD4 values and $\log_{10}$ transformed HIV-1 loads in the univariable and multivariable Cox models may be included. Further, the inverse probability weights may be used to adjust for sampling bias.

Preferably, STATA (Version 9.1, StataCorp, College Station, Tex.) may be used for quantitative analyses.

In another preferred embodiment, the method is used (a) to assess or predict the degree of HIV progression, (b) to determine when to start or change antiretroviral treatment, or (c) to monitor the efficacy of antiretroviral treatment. One of skill in the art (e.g. a physician, preferably one specializing in the treatment of infectious disease) would use appropriate judgment and discretion in determining how often to apply the diagnostic methods for a patient. The frequency of application may vary, depending on various factors, for example, the age, sex, type of antiretroviral therapy administered to, or stage of disease progression in, a patient.

The present invention further encompasses a method of determining when to initiate antiretroviral therapy in a patient which may comprise determining the viral load of a population of acquired immunodeficiency virus using the CXCR4 coreceptor (X4-specific viral load) in a patient-derived biological sample comprising the steps of: (a) screening individual molecular clones of patient-derived acquired immunodeficiency primary isolate with a heteroduplex tracking assay to determine the CCR5 coreceptor usage and the CXCR4 coreceptor usage of each individual molecular clone; (b) determining the proportion of HIV using the CCR5 coreceptor (R5) versus the CXCR4 coreceptor (R4) wherein the proportion is expressed as a variable called the Quantity of X4 and R5 (QXR), which represents the fraction of virus in a specimen using the R5 coreceptor; (c) determining coreceptor specific viral loads of the patient-derived acquired immunodeficiency primary isolate wherein the R5-specific viral load=(VL)(QXR) and the X4-specific viral load=(VL)(1−QXR) and wherein initiation or change of antiretroviral therapy may be considered anytime that the X4-specific viral load is greater than zero.

In a preferred embodiment, if QXR=1, almost all of the viruses in the population use the R5 coreceptor; if QXR=0, almost all of the viruses in the population use the X4 coreceptor; and if QXR<1, the viruses in the population use a mixture of the R5 and X4 coreceptors.

Preferably, the patient-derived biological sample is any bodily fluid or tissue. In one embodiment, the biological sample may be a bodily fluid which may be selected from the group consisting of blood, plasma, and spinal fluid. In another embodiment, the biological sample may be one which contains viral populations that are distinct from those in the readily obtained peripheral blood including the reservoirs of the genital tract and lymphoid tissue.

Patient-derived biological samples may be obtained by methods known to one of skill in the art. For instance, peripheral blood of HIV-infected individuals can be separated into plasma and cell components by methods known in the art. Primary viral isolates of HIV-1 may also be obtained by co-culture with normal donor peripheral blood mononuclear cells (PBMCs). Titration of viral isolates in PBMCs can be carried out. These standard techniques are described throughout the literature; for example, see Fang et al. (1995) Proc. Natl. Acad. Sci. USA 92:12110-4.

Preferably, the individual molecular clones each comprise a DNA sequence corresponding to a portion of the HIV genome, the DNA sequence comprising at least a portion of the genetic determinates of coreceptor usage.

In a preferred embodiment, the genetic determinates are derived from the env gene. The envelope protein may comprise gp 120, gp 160 or a portion thereof. Envelope sequences are predictive of coreceptor use on the basis of the overall charge of the V3 loop and the presence of basic or acidic residues at positions 275 and 287 of the env gene (Bhattacharya et al. (1996) AIDS Res. Hum. Retrovir. 12:83-90; Hung et al. (1999) J. Virol. 73:8216-26; and Cardozo et al (2007) AIDS Res. Hum. Retrovir. In press).

Cloning strategies for isolating envelope genes of interest are well known to one of skill in the art. See, for example, Sambrook, Fritsch and Maniatis, Molecular Cloning, A Laboratory Manual, $2^{nd}$ Ed., Cold Spring Harbor Laboratory Press, 1989.

Preferably, the cloning methods used in the present invention will decrease the chance of sampling error or recombination. For example, high fidelity cloning of the samples above may be achieved by routine performance of multiple long RT-PCR reactions on limiting dilutions of RNA, followed by multiple PCR's on cDNAs obtained from each RT reaction. In addition, performance of multiple PCR's on each cDNA preparation increases the likelihood of amplifying a different HIV-1 RNA species. Short-term limited dilution techniques are also well known to one of skill in the art, see for example, Connor et al. (1997). Furthermore, quantitation of HIV-1 RNA in the biological samples of the methods described herein may be carried out, for example, by using NucliSens (Organon Teknika Corp., Durham, N.C.). Quantitation methods may set outer limits. In a preferred embodiment, RNA is amplified to ≦80 copies/ml.

In a preferred embodiment, the molecular clones each are derived from RNA of the patient-derived HIV and correspond to the HIV genome or a portion thereof and which comprise the genetic determinates of coreceptor usage or a portion thereof. In another preferred embodiment, the molecular clones are prepared by RT-PCR of the RNA of the patient-derived HIV and at least one set of oligonucleotide primers. In a more preferred embodiment, at least one set of oligonucleotide primers consists of the first set of primers in Table 3. In another more preferred embodiment, at least one set of oligonucleotide primers includes a second set of oligonucleotide primers, the second set consisting of the second set of primers in Table 3. Preferably, the number of individual molecular clones is at least 20.

In a preferred embodiment, the heteroduplex tracking assay of the method may comprise the steps of: (a) amplifying the individual molecular clone or a portion thereof by PCR to provide amplified DNA comprising the genetic determinates of coreceptor usage or a portion thereof; (b) forming a population of heteroduplex molecules by contacting the amplified DNA with a labeled probe complementary to the amplified DNA under conditions sufficient to form heteroduplexes; (c) separating the population of heteroduplex molecules using a separation means; (d) detecting the presence or absence of heteroduplex molecules; wherein the presence or absence of heteroduplex molecules reveals coreceptor usage. More preferably, the labeled probe may be derived from a known HIV-1 CCR5 clone or from a known HIV-1 CXCR4 clone. In another preferred embodiment, the labeled probe comprises a detectable moiety, a radioisotope, biotin, a fluorescent moiety, a fluorophore, a chemiluminescent moiety, or an enzymatic moiety.

The heteroduplex tracking assay of the invention can be carried out substantially in accordance with the guidance of Delwart et al. (J. Virol. (1994) 68:6672-6683), Delwart et al. (Science (1993) 262:1257-1261), Nelson et al. (J. Virol. (1997) 71:8850-8; Delwart et al. (PCR Methods and Applications 4:S202-S216 (19950 Cold Springs Harbor), and U.S. Pat. No. 5,851,759 (Weiner), each of which are incorporated in their entireties by reference.

The heteroduplex tracking assay can be used to analyze a portion of the HIV-1 genome encompassing determinates of coreceptor utilization to understand, determine, monitor, or detect coreceptor usage. Genetic determinates of HIV-1 coreceptor utilization can be found in the envelope gene (env), with key determinates being found in the third variable (V3) domain of the gp120 glycoprotein.

The heteroduplex tracking assay of the invention can be carried out generally, while not being limited thereto, according to the basic steps of: (a) obtaining HIV viral RNA from the patient, (b) amplifying, e.g. PCR and/or reverse transcription, a portion of the viral genome containing genetic determinates of coreceptor usage, e.g. a genomic portion comprising the V3 domain of the gp120 envelope glycoprotein, (c) forming heteroduplexes and/or homoduplexes with labeled nucleic acid-based probes prepared from a corresponding genomic region of a known HIV strain, e.g. the same genomic portion comprising the V3 domain of gp120, and (d) subjecting the heteroduplexes and homoduplexes to a separation system, e.g. electrophoresis through non-denaturing polyacrylamide gels, wherein the heteroduplexes and homoduplexes have differing and distinguishable mobilities that results in different mobility patterns, e.g. a electrophoretic pattern, such that the coreceptor usage can be determined.

For example, the presence of an electrophoretic pattern characteristic of X4-heteroduplexes can indicate the presence of CXCR4-specific viruses in the HIV sample. Alternately, the presence of an electrophoretic pattern characteristic of homoduplexes and R5-heteroduplexes can indicate the presence of only CCR5-specific viruses. And, a pattern characteristic of both homoduplexes and X4- and R5-heteroduplexes can indicate that the HIV sample contains a mixed population of CCR5-specific and CXCR4-specific viruses. The heteroduplex tracking assay can be performed at any point during disease progression or during, before, or after administering antiretroviral therapy. Further, the heteroduplex tracking assay can be carried out either to attain qualitative results or quantitative results.

Methods for obtaining and/or extracting HIV RNA from patient-derived samples are well-known. Also, the step of amplifying a portion of the viral genome containing genetic determinates of coreceptor usage a known in the art, and include, for example reverse transcription PCR (RT-PCR). Following RT-PCT, further rounds of PCR can be used to further amplify desired portions of the genome, especially regions containing genetic determinates of coreceptor usage.

It will be appreciated that the heteroduplex tracking assay is based on the observation that when sequences were amplified by nested PCR from peripheral blood mononuclear cells of infected individuals, related DNA products coamplified from divergent templates could randomly reanneal to form heteroduplexes that migrate with reduced mobility in neutral polyacrylamide gels. Using these techniques, one can establish genetic relationships between multiple viral DNA template molecules, such as the different genetic types (i.e. different genotypes) of HIV utilizing the different coreceptors. The HTA of the invention can be described as utilizing a first PCR product as a labeled probe, e.g. radioactive or nonradioactive, which is mixed with an excess ("driver") of an unlabeled PCR product from a different source, i.e., the source for which typing or analysis of is desired, e.g. the PCR product defining the portion of the HIV genome with the coreceptor genetic determinates. The probe sequences are then "driven" completely into heteroduplexes with the driver, and are separated, e.g. by gel electrophoresis, on the basis of size. An autoradiogram or fluoroimage, for example, of the resulting polyacrylamide gel reveals these heteroduplexes and provides a visual display of the relationship between the two virus populations under study. The fact that heteroduplexes migrate with distinct mobilities indicates that the strand-specific composition of mismatched and unpaired nucleotides affects their mobility.

A "heteroduplex" encompasses a doublestranded DNA molecule having complementary strands at which one strand (the "target strand", i.e. a single strand of DNA from the PCR product of the HIV genome) contains one or more mismatched or an unpaired nucleotide base. For example, a heteroduplex can form by mixing together a labeled probe (e.g. a double-stranded DNA PCR product of a portion of the envgene of CCR5-specific HIV) and a PCR product of a target sequence (e.g. a double-stranded DNA PCR product of the corresponding portion of the env gene of a CXCR4-specific HIV) such that complementary single-stranded DNA of each PCR product are combined together as a new, double-stranded molecule. However, since the PCR product from the CXCR4-specific HIV will contain genetic determinates characteristic of CXCR4 type viruses, its nucleotide sequence will vary at specific locations with respect to the probe PCR product (which is derived from CCR5). These differences in sequence result in a heteroduplex which has reduced mobility during electrophoresis with respect to homoduplexes owing to a reduced level of base-pairing in the molecule. In contrast, the "homoduplex" may be formed between complementary strand pairs derived from a probe PCR product and a target PCR product such that their nucleotide sequences are the same.

In another embodiment, the heteroduplex tracking assay can comprise the steps of (a) amplifying an individual molecular clone or a portion thereof by PCR to provide amplified DNA comprising the genetic determinates of coreceptor usage or a portion thereof; (b) forming a population of heteroduplex molecules by contacting the amplified DNA with a labeled probe complementary to the amplified DNA under conditions sufficient to form heteroduplexes; (c) separating the population of heteroduplex molecules using a separation means: and (d) detecting the presence or absence of heteroduplex molecules; wherein the presence or absence of heteroduplex molecules reveals coreceptor usage. In one embodiment, the labeled probe may be derived from a known HIV-1 CCR5 clone. In another embodiment, the labeled probe may be derived from a known HIV-1 CXCR4 clone. The labeled probe can comprise a detectable moiety, a radioisotope, biotin, a fluorescent moiety, a fluorophore, a chemiluminescent moiety, or an enzymatic moiety. Appropriate labels and their methods of preparation are well-known.

It is furthermore envisaged that the diagnostic method may involve the use of micro-chips comprising nucleic acid molecules encoding a envelope protein, or a fragment thereof, preferably a V3 region fragment, especially including genetic determinates of coreceptor usage, on gene chips; or an envelope protein, or a fragment thereof, preferably a V3 region fragment, on protein-chips (See U.S. Pat. Nos. 6,066,454; 6,045,996; 6,043,080; 6,040,193; 6,040,138; 6,033,860; 6,033,850; 6,025,601; 6,022,963; 6,013,440; 5,968,740; 5,925,525; 5,922,591; 5,919,523; 5,889,165; 5,885,837; 5,874,219; 5,858,659; 5,856,174; 5,856,101; 5,843,655; 5,837,832; 5,834,758; 5,831,070; 5,770,722; 5,770,456; 5,753,788; 5,744,305; 5,733,729; 5,710,000; 5,631,734; 5,599,695; 5,593,839; 5,578,832; and 5,556,752). Diagnostic gene chips may comprise a collection of polypeptides that specifically detect a envelope protein, or fragments thereof, preferably V3 region fragments; or nucleic acid molecules that specifically detect a nucleic acid molecule encoding a envelope protein, or fragments thereof, preferably V3 region fragments; all of which may be used for the purposes of determining coreceptor use. The envelope protein may be gp160, gp 120, or a portion thereof.

It will be understood that the heteroduplex tracking assay of the invention can be used to provide both qualitative and quantitative information. First, qualitative information can be derived using the HTA of the invention by analyzing the whole HIV population derived from an infected patient to determine whether the isolated population of HIV is CCR5-specific, CXCR5-specific, or mixture of both types. It will be appreciated that qualitative information is based on the whole or substantially the whole HIV population rather than individual clones therefrom. On the contrary, quantitative information can be derived using the HTA of the present invention by analyzing individual HIV clones (e.g. cloned portions of the HIV genome of a plurality of individual HIV viruses from the isolated whole population of HIV from the infected patient) with respect to their coreceptor usage and determining a ratio of CCR5-specific to CXCR4-specific clones. In one embodiment, the invention relates to determining the QXR ratio: the number of HIV clones that are identified as CCR5-specific compared to the total number of clones analyzed. It will be appreciated that the HIV clone refers to the cloned PCR product.

FIG. 5 depicts a flow chart showing the qualitative and quantitative aspects of the HTA of the present invention. First, HIV RNA is extracted from the infected patient. Next, RT-PCR is carried out to obtain HIV cDNA, from which a PCR product (i.e. PCR amplicon) containing genetic determinates for coreceptor usage is amplied using PCR. The PCR product is then gel purified. Presumably, the PCR product will be a mixed population of molecules—those genotypic for either CCR5 or CXCR4 coreceptors—whenever the isolated HIV sample contains both types of viruses. Next, the PCR product is analyzed by the HTA of the invention, which includes generally the steps of mixing together a labeled probe (e.g. a PCR product corresponding to same region in a known CCR5 strain as the amplified target PCR amplicon to be analyzed) and the amplified target PCR amplicon to form homo- or heteroduplexes. The molecules are then separated by gel electrophoresis, for example, on a 12% polyacrylamide gel. Electrophetic techniques are well known in the art. If the QXR<1 on the qualitative test, then a quantitative test can be done. To perform the quantitative test the V3 portion of the HIV envelope gene is molecularly cloned and each of 20 clones is analyzed by an individual HTA.

Exemplarly results are represented in FIG. 6. The figures shows four panels of schematic electropherograms. The first panel is the negative control, i.e. labeled probe only. The second panel shows the result of HTA of the V3 portion of the HIV envelope gene of a CCR5 virus. The third panel shows the result of HTA of a CXCR4 virus. And, the fourth panel shows the result of HTA of a mixture of CCR5 and CXCR4 virus V3 regions. Four different probes (each based on a CCR5-specific control virus) were used to test each HIV sample. The gels show heteroduplex band patterns for those HIV samples containing CXCR4-specific and CCR5-specific viruses.

The quantitative results of the heteroduplex tracking assay of the method of the present invention may be assessed by statistical methods well known to one of skill in the art. For example, QXR, the proportion of plasma HIV-1 using CCR5, may be stratified into two categories: QXR=1 if all virus identified uses CCR5, and QXR<1 if X4 virus is detected. The association between virologic responses and baseline QXR may be assessed by comparing the percentages of patients with undetectable HIV-1 RNA load across the different strata by using, for example, Fischer's exact test. Further, immunologic responses across two strata may be compared by Wilcoxon rank-sum tests. Kaplan-Meier curves and Cox proportional hazard regression models may be applied to quantify the association of baseline or follow-up QXR (equal 1 versus less than 1) with subsequent clinical progression, defined as a new clinical AIDS-defining event or death.

The quantitative results of the heteroduplex tracking assay of the method of the present invention may further be assessed by other statistical methods well known to one of skill in the art. For example, an additional model analyzing the relationship of X4 viral load to HIV-1 disease progression may be included by stratifying the X4-specific viral load into three strata: patients without detectable X4-specific viral load (i.e., QXR=1) and patients with detectable X4 viraemia below and above the median value of X4-specific viral loads, respectively. To compare the predictive capacity with the established progression markers CD4 and HIV-1 RNA load the concurrent $\log_2$ transformed CD4 values and $\log_{10}$ transformed HIV-1 loads in the univariable and multivariable Cox models may be included. Further, the inverse probability weights may be used to adjust for sampling bias.

Preferably, STATA (Version 9.1, StataCorp, College Station, Tex.) may be used for quantitative analyses.

One of skill in the art (e.g. a physician, preferably one specializing in the treatment of infectious disease) would use appropriate judgment and discretion in determining how often to apply the diagnostic methods for a patient. The frequency of application may vary, depending on various factors, for example, the age, sex, type of antiretroviral therapy administered to, or stage of disease progression in, a patient.

In another preferred embodiment, the antiretroviral therapy of the method is any suitable antiretroviral treatment regimen. More preferably, the antiretroviral therapy is selected from the group consisting of combination antiretroviral therapy (cART), protease inhibitors, fusion inhibitors, integrase inhibitors, coreceptor specific agents, nonnucleoside analogue reverse transcriptase inhibitors and nucleoside analogue reverse transcriptase inhibitors. Preferably, the nucleoside analogue reverse transcriptase inhibitor may be 3TC or AZT. Preferably, the nonnucleoside analogue reverse transcriptase inhibitor is nevirapine.

Antiretroviral therapy may include, but is not limited to, HAART, protease inhibitors, fusion inhibitors, integrase inhibitors, co-receptor specific agents, 3TC, AZT, nevirapine, non-nucleoside analogue reverse transcriptase inhibitors and nucleoside analogue reverse transcriptase inhibitors. HAART can be three or more antiretroviral drugs in combination. The term "HAART" as used herein refers to an combination of highly active antiretroviral agents and usually comprises three drugs.

Typical reverse transcriptase inhibitors include nucleoside analogs, such as, but not limited to, (zidovudine, (AZT, Retrovir), didanosine (ddI, Videx), stavudine, (d4T, Zerit), lamivudine, 3TC, Epivir), abacavir, (ABC, Ziagen), tenofovir, (TDF, Viread), combivir (CBV, combination of AZT and 3TC), and non-nucleoside reverse transcriptase inhibitors, e.g., nevirapine (NVP, Viramune), delavirdine (DLV, rescriptor), efavirenz, (EFV, sustiva,). Protease inhibitors include saquinavir, (SQV, Invirase), ritonavir (RTV, Norvir), indinavir, (IDV, Crixivan), nelfinavir, (NFV, Viracept), fosamprenivir, FPV, Lexiva), kaletra (lopinavir and ritonavir) and fortovase (saquinavir in a soft gelatin form). Thus, HAART can also be "triple cocktail" therapy—a three drug regimen to combat HIV.

The present invention further encompasses a method of monitoring the efficacy of antiretroviral therapy in a patient which may comprise determining the viral load of acquired immunodeficiency virus using the CXCR4 coreceptor (X4-specific viral load) in a patient-derived biological sample comprising the steps of: (a) screening individual molecular clones of patient-derived acquired immunodeficiency primary isolate with a heteroduplex tracking assay to determine the CCR5 coreceptor usage and the CXCR4 coreceptor usage of each individual molecular clone; (b) determining the proportion of HIV using the CCR5 coreceptor (R5) versus the CXCR4 coreceptor (R4) wherein the proportion is expressed as a variable called the Quantity of X4 and R5 (QXR), which represents the fraction of virus in a specimen using the R5 coreceptor; (c) determining coreceptor specific viral loads of the patient-derived acquired immunodeficiency primary isolate wherein the R5-specific viral load=(VL)(QXR) and the X4-specific viral load=(VL)(1−QXR), wherein X4-specific viral load strongly predicts disease progression during cART.

In a preferred embodiment, if QXR=1, almost all of the viruses in a population use the R5 coreceptor; if QXR=0, almost all of the viruses in a population use the X4 coreceptor; and if QXR<1, the viruses in a population use a mixture of the R5 and X4 coreceptors.

Preferably, the patient-derived biological sample is any bodily fluid or tissue. In one embodiment, the biological sample may be a bodily fluid which may be selected from the group consisting of blood, plasma, and spinal fluid. In another embodiment, the biological sample may be one which contains viral populations that are distinct from those in the readily obtained peripheral blood including the reservoirs of the genital tract and lymphoid tissue.

Patient-derived biological samples may be obtained by methods known to one of skill in the art. For instance, peripheral blood of HIV-infected individuals can be separated into plasma and cell components by methods known in the art. Primary viral isolates of HIV-1 may also be obtained by co-culture with normal donor peripheral blood mononuclear cells (PBMCs). Titration of viral isolates in PBMCs can be carried out. These standard techniques are described throughout the literature; for example, see Fang et al. (1995) Proc. Natl. Acad. Sci. USA 92:12110-4.

Preferably, the individual molecular clones each comprise a DNA sequence corresponding to a portion of the HIV genome, the DNA sequence comprising at least a portion of the genetic determinates of coreceptor usage.

In a preferred embodiment, the genetic determinates are derived from the env gene. The envelope protein may comprise gp120, gp160 or a portion thereof. Envelope sequences are predictive of coreceptor use on the basis of the overall charge of the V3 loop and the presence of basic or acidic residues at positions 275 and 287 of the env gene (Bhattacharya et al. (1996) AIDS Res. Hum. Retrovir. 12:83-90; and Hung et al. (1999) J. Virol. 73:8216-26; and; Cardozo et al. (2007) AIDS Res. Hum. Retrovir. In press).

Cloning strategies for isolating envelope genes of interest are well known to one of skill in the art. See, for example, Sambrook, Fritsch and Maniatis, Molecular Cloning, A Laboratory Manual, 2$^{nd}$ Ed., Cold Spring Harbor Laboratory Press, 1989.

Preferably, the cloning methods used in the present invention will decrease the chance of sampling error or recombination. For example, high fidelity cloning of the samples above may be achieved by routine performance of multiple long RT-PCR reactions on limiting dilutions of RNA, followed by multiple PCR's on cDNAs obtained from each RT reaction. In addition, performance of multiple PCR's on each cDNA preparation increases the likelihood of amplifying a different HIV-1 RNA species. Short-term limited dilution techniques are also well known to one of skill in the art, see for example, Connor et al. (1997). Furthermore, quantitation of HIV-1 RNA in the biological samples of the methods described herein may be carried out, for example, by using NucliSens (Organon Teknika Corp., Durham, N.C.). Quantitation methods may set outer limits. In a preferred embodiment, RNA is amplified to ≦80 copies/ml.

In a preferred embodiment, the molecular clones each are derived from RNA of the patient-derived HIV and correspond to the HIV genome or a portion thereof and which comprise the genetic determinates of coreceptor usage or a portion thereof. In another preferred embodiment, the molecular clones are prepared by PCR of the RNA of the patient-derived HIV and at least one set of oligonucleotide primers. In a more preferred embodiment, at least one set of oligonucleotide primers consists of the first set of primers in Table 3. In another more preferred embodiment, at least one set of oligonucleotide primers includes a second set of oligonucleotide primers, the second set consisting of the second set of primers in Table 3. Preferably, the number of individual molecular clones is at least 20.

In a preferred embodiment, the heteroduplex tracking assay of the method may comprise the steps of: (a) amplifying the individual molecular clone or a portion thereof by PCR to provide amplified DNA comprising the genetic determinates of coreceptor usage or a portion thereof; (b) forming a population of heteroduplex molecules by contacting the amplified DNA with a labeled probe complementary to the amplified DNA under conditions sufficient to form heteroduplexes; (c) separating the population of heteroduplex molecules using a separation means; (d) detecting the presence or absence of heteroduplex molecules; wherein the presence or absence of heteroduplex molecules reveals coreceptor usage. More preferably, the labeled probe may be derived from a known HIV-1 CCR5 clone or from a known HIV-1 CXCR4 clone. In another preferred embodiment, the labeled probe comprises a detectable moiety, a radioisotope, biotin, a fluorescent moiety, a fluorophore, a chemiluminescent moiety, or an enzymatic moiety.

The heteroduplex tracking assay of the invention can be carried out substantially in accordance with the guidance of Delwart et al. (J. Virol. (1994) 68:6672-6683), Delwart et al. (Science (1993) 262:1257-1261), Nelson et al. (J. Virol. (1997) 71:8850-8; Delwart et al. (PCR Methods and Applications 4:S202-S216 (19950 Cold Springs Harbor), and U.S. Pat. No. 5,851,759 (Weiner), each of which are incorporated in their entireties by reference.

The heteroduplex tracking assay can be used to analyze a portion of the HIV-1 genome encompassing determinates of coreceptor utilization to understand, determine, monitor, or detect coreceptor usage. Genetic determinates of HIV-1 coreceptor utilization can be found in the envelope gene (env), with key determinates being found in the third variable (V3) domain of the gp120 glycoprotein.

The heteroduplex tracking assay of the invention can be carried out generally, while not being limited thereto, according to the basic steps of: (a) obtaining HIV viral RNA from the patient, (b) amplifying, e.g. PCR and/or reverse transcription, a portion of the viral genome containing genetic determinates of coreceptor usage, e.g. a genomic portion comprising the V3 domain of the gp120 envelope glycoprotein, (c) forming heteroduplexes and/or homoduplexes with labeled nucleic acid-based probes prepared from a corresponding genomic region of a known HIV strain, e.g. the same genomic portion comprising the V3 domain of gp120, and (d) subjecting the heteroduplexes and homoduplexes to a separation system, e.g. electrophoresis through non-denaturing polyacrylamide gels, wherein the heteroduplexes and homoduplexes have differing and distinguishable mobilities that results in different mobility patterns, e.g. a electrophoretic pattern, such that the coreceptor usage can be determined.

For example, the presence of an electrophoretic pattern characteristic of X4-heteroduplexes can indicate the presence of CXCR4-specific viruses in the HIV sample. Alternately, the presence of an electrophoretic pattern characteristic of homoduplexes and R5-heteroduplexes can indicate the presence of only CCR5-specific viruses. And, a pattern characteristic of both homoduplexes and X4- and R5-heteroduplexes can indicate that the HIV sample contains a mixed population of CCR5-specific and CXCR4-specific viruses. The heteroduplex tracking assay can be performed at any point during disease progression or during, before, or after administering antiretroviral therapy. Further, the heteroduplex tracking assay can be carried out either to attain qualitative results or quantitative results.

Methods for obtaining and/or extracting HIV RNA from patient-derived samples are well-known. Also, the step of amplifying a portion of the viral genome containing genetic determinates of coreceptor usage a known in the art, and include, for example reverse transcription PCR (RT-PCR). Following RT-PCT, further rounds of PCR can be used to further amplify desired portions of the genome, especially regions containing genetic determinates of coreceptor usage.

It will be appreciated that the heteroduplex tracking assay is based on the observation that when sequences were amplified by nested PCR from peripheral blood mononuclear cells of infected individuals, related DNA products coamplified from divergent templates could randomly reanneal to form heteroduplexes that migrate with reduced mobility in neutral polyacrylamide gels. Using these techniques, one can establish genetic relationships between multiple viral DNA template molecules, such as the different genetic types (i.e. different genotypes) of HIV utilizing the different coreceptors. The HTA of the invention can be described as utilizing a first PCR product as a labeled probe, e.g. radioactive or nonradioactive, which is mixed with an excess ("driver") of an unlabeled PCR product from a different source, i.e., the source for which typing or analysis of is desired, e.g. the PCR product defining the portion of the HIV genome with the coreceptor genetic determinates. The probe sequences are then "driven" completely into heteroduplexes with the driver, and are separated, e.g. by gel electrophoresis, on the basis of size. An autoradiogram or fluoroimage, for example, of the resulting polyacrylamide gel reveals these heteroduplexes and provides a visual display of the relationship between the two virus populations under study. The fact that heteroduplexes migrate with distinct mobilities indicates that the strand-specific composition of mismatched and unpaired nucleotides affects their mobility.

A "heteroduplex" encompasses a doublestranded DNA molecule having complementary strands at which one strand (the "target strand", i.e. a single strand of DNA from the PCR product of the HIV genome) contains one or more mismatched or an unpaired nucleotide base. For example, a heteroduplex can form by mixing together a labeled probe (e.g. a double-stranded DNA PCR product of a portion of the envgene of CCR5-specific HIV) and a PCR product of a target sequence (e.g. a double-stranded DNA PCR product of the corresponding portion of the env gene of a CXCR4-specific HIV) such that complementary single-stranded DNA of each PCR product are combined together as a new, double-stranded molecule. However, since the PCR product from the CXCR4-specific HIV will contain genetic determinates characteristic of CXCR4 type viruses, its nucleotide sequence will vary at specific locations with respect to the probe PCR product (which is derived from CCR5). These differences in sequence result in a heteroduplex which has reduced mobility during electrophoresis with respect to homoduplexes oweing to a reduced level of base-pairing in the molecule. In contrast, the "homoduplex" may be formed between complementary strand pairs derived from a probe PCR product and a target PCR product such that their nucleotide sequences are the same.

In another embodiment, the heteroduplex tracking assay can comprise the steps of (a) amplifying an individual molecular clone or a portion thereof by PCR to provide amplified DNA comprising the genetic determinates of coreceptor usage or a portion thereof; (b) forming a population of heteroduplex molecules by contacting the amplified DNA with a labeled probe complementary to the amplified DNA under conditions sufficient to form heteroduplexes; (c) separating the population of heteroduplex molecules using a separation means: and (d) detecting the presence or absence of heteroduplex molecules; wherein the presence or absence of heteroduplex molecules reveals coreceptor usage. In one embodiment, the labeled probe may be derived from a known HIV-1 CCR5 clone. In another embodiment, the labeled probe may be derived from a known HIV-1 CXCR4 clone. The labeled probe can comprise a detectable moiety, a radioisotope, biotin, a fluorescent moiety, a fluorophore, a chemiluminescent moiety, or an enzymatic moiety. Appropriate labels and their methods of preparation are well-known.

It is furthermore envisaged that the diagnostic method may involve the use of micro-chips comprising nucleic acid molecules encoding a envelope protein, or a fragment thereof, preferably a V3 region fragment, especially including genetic determinates of coreceptor usage, on gene chips; or an envelope protein, or a fragment thereof, preferably a V3 region fragment, on protein-chips (See U.S. Pat. Nos. 6,066,454; 6,045,996; 6,043,080; 6,040,193; 6,040,138; 6,033,860; 6,033,850; 6,025,601; 6,022,963; 6,013,440; 5,968,740; 5,925,525; 5,922,591; 5,919,523; 5,889,165; 5,885,837; 5,874,219; 5,858,659; 5,856,174; 5,856,101; 5,843,655; 5,837,832; 5,834,758; 5,831,070; 5,770,722; 5,770,456; 5,753,788; 5,744,305; 5,733,729; 5,710,000; 5,631,734; 5,599,695; 5,593,839; 5,578,832; and 5,556,752). Diagnostic gene chips may comprise a collection of polypeptides that specifically detect a envelope protein, or fragments thereof, preferably V3 region fragments; or nucleic acid molecules that specifically detect a nucleic acid molecule encoding a envelope protein, or fragments thereof, preferably V3 region fragments; all of which may be used for the purposes of determining coreceptor use. The envelope protein may be gp160, gp 120, or a portion thereof.

It will be understood that the heteroduplex tracking assay of the invention can be used to provide both qualitative and quantitative information. First, qualitative information can be derived using the HTA of the invention by analyzing the whole HIV population derived from an infected patient to determine whether the isolated population of HIV is CCR5-specific, CXCR5-specific, or mixture of both types. It will be appreciated that qualitative information is based on the whole or substantially the whole HIV population rather than individual clones therefrom. On the contrary, quantitative information can be derived using the HTA of the present invention by analyzing individual HIV clones (e.g. cloned portions of the HIV genome of a plurality of individual HIV viruses from the isolated whole population of HIV from the infected patient) with respect to their coreceptor usage and determining a ratio of CCR5-specific to CXCR4-specific clones. In one embodiment, the invention relates to determining the QXR ratio: the number of HIV clones that are identified as CCR5-specific compared to the total number of clones analyzed. It will be appreciated that the HIV clone refers to the cloned PCR product.

FIG. 5 depicts a flow chart showing the qualitative and quantitative aspects of the HTA of the present invention. First, HIV RNA is extracted from the infected patient. Next, RT-PCR is carried out to obtain HIV cDNA, from which a PCR product (i.e. PCR amplicon) containing genetic determinates for coreceptor usage is amplied using PCR. The PCR product is then gel purified. Presumably, the PCR product will be a mixed population of molecules—those genotypic for either CCR5 or CXCR4 coreceptors—whenever the isolated HIV sample contains both types of viruses. Next, the PCR product is analyzed by the HTA of the invention, which includes generally the steps of mixing together a labeled probe (e.g. a PCR product corresponding to same region in a known CCR5 strain as the amplified target PCR amplicon to be analyzed)

and the amplified target PCR amplicon to form homo- or heteroduplexes. The molecules are then separated by gel electrophoresis, for example, on a 12% polyacrylamide gel. Electrophetic techniques are well known in the art. If the QXR<1 on the qualitative test, then a quantitative test can be done. To perform the quantitative test the V3 portion of the HIV envelope gene is molecularly cloned and each of 20 clones is analyzed by an individual HTA.

Exemplarly results are represented in FIG. 6. The figures shows four panels of schematic electropherograms. The first panel is the negative control, i.e. labeled probe only. The second panel shows the result of HTA of the V3 region of the envelope gene of a CCR5 virus. The third panel shows the result of HTA of the V3 region of the envelope gene of a CXCR4 virus. And, the fourth panel shows the result of HTA of a mixture of CCR5 and CXCR4 virus V3 regions. Four different probes (each based on a CCR5-specific control virus) were used to test each HIV sample. The gels show heteroduplex band patterns for those HIV samples containing CXCR4-specific and CCR5-specific viruses.

The quantitative results of the heteroduplex tracking assay of the method of the present invention may be assessed by statistical methods well known to one of skill in the art. For example, QXR, the proportion of plasma HIV-1 using CCR5, may be stratified into two categories: QXR=1 if all virus identified uses CCR5, and QXR<1 if X4 virus is detected. The association between virologic responses and baseline QXR may be assessed by comparing the percentages of patients with undetectable HIV-1 RNA load across the different strata by using, for example, Fischer's exact test. Further, immunologic responses across two strata may be compared by Wilcoxon rank-sum tests. Kaplan-Meier curves and Cox proportional hazard regression models may be applied to quantify the association of baseline or follow-up QXR (equal 1 versus less than 1) with subsequent clinical progression, defined as a new clinical AIDS-defining event or death.

The quantitative results of the heteroduplex tracking assay of the method of the present invention may further be assessed by other statistical methods well known to one of skill in the art. For example, an additional model analyzing the relationship of X4 viral load to HIV-1 disease progression may be included by stratifying the X4-specific viral load into three strata: patients without detectable X4-specific viral load (i.e., QXR=1) and patients with detectable X4 viraemia below and above the median value of X4-specific viral loads, respectively. To compare the predictive capacity with the established progression markers CD4 and HIV-1 RNA load the concurrent $\log_2$ transformed CD4 values and $\log_{10}$ transformed HIV-1 loads in the univariable and multivariable Cox models may be included. Further, the inverse probability weights may be used to adjust for sampling bias.

Preferably, STATA (Version 9.1, StataCorp, College Station, Tex.) may be used for quantitative analyses.

One of skill in the art (e.g. a physician, preferably one specializing in the treatment of infectious disease) would use appropriate judgment and discretion in determining how often to apply the diagnostic methods for a patient. The frequency of application may vary, depending on various factors, for example, the age, sex, type of antiretroviral therapy administered to, or stage of disease progression in, a patient.

In another preferred embodiment, the antiretroviral therapy of the method is any suitable antiretroviral treatment regimen. More preferably, the antiretroviral therapy is selected from the group consisting of combination antiretroviral therapy (cART), protease inhibitors, fusion inhibitors, integrase inhibitors, coreceptor specific agents, nonnucleoside analogue reverse transcriptase inhibitors and nucleoside analogue reverse transcriptase inhibitors. Preferably, the nucleoside analogue reverse transcriptase inhibitor may be 3TC or AZT. Preferably, the nonnucleoside analogue reverse transcriptase inhibitor is nevirapine.

Antiretroviral therapy may include, but is not limited to, HAART, protease inhibitors, fusion inhibitors, integrase inhibitors, co-receptor specific agents, 3TC, AZT, FTC, efavirenz, nevirapine, non-nucleoside analogue reverse transcriptase inhibitors and nucleoside analogue reverse transcriptase inhibitors. HAART can be three or more antiretroviral drugs in combination. The term "HAART" as used herein refers to a combination of highly active antiretroviral agents and usually comprises three drugs Typical reverse transcriptase inhibitors include nucleoside analogs, such as, but not limited to, zidovudine, (AZT, Retrovir), didanosine (ddI, Videx), stavudine, (d4T, Zerit), lamivudine, 3TC, Epivir), abacavir, (ABC, Ziagen), tenofovir, (TDF, Viread), combivir (CBV, combination of AZT and 3TC), and non-nucleoside reverse transcriptase inhibitors, e.g., nevirapine (NVP, Viramune), delavirdine (DLV, rescriptor), efavirenz, (EFV, sustiva,). Protease inhibitors include saquinavir, (SQV, Invirase), ritonavir (RTV, Norvir), indinavir, (IDV, Crixivan), nelfinavir, (NFV, Viracept), fosamprenivir, FPV, Lexiva), kaletra (lopinavir and ritonavir) and fortovase (saquinavir in a soft gelatin form). Thus, HAART can also be "triple cocktail" therapy—a three drug regimen to combat HIV.

The present invention further encompasses a diagnostic composition comprised of the methods of the present invention in the form of a kit. The diagnostic composition may comprise the components as defined herein above wherein said components are bound to/attached to and/or linked to a solid support. It is furthermore envisaged, that the diagnostic composition may comprise nucleic acid sequences encoding an envelope protein, or a fragment thereof, preferably a V3 region fragment; or indicator cell lines of this invention; all of which may be contained on micro-chips identifiable with a suitable means for detection.

Solid supports are well known in the art and comprise, inter alia, commercially available column materials, polystyrene beads, latex beads, magnetic beads, colloid metal particles, glass and/or silicon chips and surfaces, nitrocellulose strips, membranes, sheets, duracytes, wells and walls of reaction trays, plastic tubes etc. Suitable methods for fixing/immobilizing cells, nucleic acid sequences, or polypeptides of the invention are well known and include, but are not limited to ionic, hydrophobic, covalent interactions and the like.

The diagnostic composition of the present invention may be used as a kit, inter alia, for carrying out the methods of the present invention, for example diagnostic kits or research tools. Additionally, the kit of the invention may contain suitable means for any other scientific, medical and/or diagnostic purposes.

Diagnostic compositions and kits of the present invention may be manufactured by standard procedures that are well known to one of skill in the art. Kits may advantageously include instructions for use and/or admixture of ingredients.

One of skill in the art appreciates that the diagnostic compositions and kits of the present invention are not limited to use with HIV, but may be used, based on the teachings herein and knowledge of one of skill in the art, to identify and quantitate analogous coreceptors of other lentiviruses, such as SIV and FIV. (See, for example, U.S. Pat. Nos. 5,863,542 and 5,766,598).

The present invention is additionally described by way of the following illustrative, non-limiting Examples, that provide a better understanding of the present invention and of its many advantages.

EXAMPLES

The Examples show that HAART not only reduces the quantity of virus but also affects HIV-1 coreceptor use. Briefly, methods were devised for quantifying the proportion of viruses in patient-derived virus that used each coreceptor and monitoring the effect of combination antiretroviral therapy, particularly HAART, on coreceptor use. The Examples further show that QXR and X4-specific viral load are predictors of disease progression and clinical outcome.

Example 1

Study Population

Coreceptor use was examined in twenty-two women who participated in two prospective studies of HIV-1 infection. Nineteen were enrolled in the Bronx-Manhattan site of Women's Interagency HIV Study (WIHS), a National Institutes of Health (NIH) multicenter study of the natural history of HIV-1 infection in women. Three took part in a study of HIV-1 pathogenesis performed at the Wadsworth Center of the New York State Department of Health in Albany, N.Y. Both studies included individuals with a broad spectrum of HIV-1 disease. The institutional review boards at each clinical site and the New York State Department of Health approved the investigation. Each woman provided informed consent at enrollment.

To examine the effect of combination antiretroviral therapy on HIV-1 coreceptor use, women infected with CXCR4 strains were sought. After screening twenty-two women, most with advanced HIV-1 disease, fifteen participants meeting the following criteria were studied: 1) viral isolates displayed CXCR4 strains while untreated or taking nucleoside analogues alone; and 2) antiretroviral therapy, when initiated, was documented by the WIHS database, Wadsworth study questionnaires, and records of treating physicians.

Sample Collection, Preparation, and Analysis

Once the study population was selected, blood was drawn and separated into plasma and cell components (Anastos et al. (2000) J. AIDS Hum. Retro. (in press); Fang et al. (1995)). HIV-1 RNA in plasma was quantitated by using NucliSens (Organon Teknika Corp., Durham, N.C.), with a lower limit of quantitation of ~80 copies/ml. The CCR5 genotype of each patient was determined as described (Samson et al. (1996)).

Derivation of Primary Viral Isolates and Biological Clones

Primary isolates of HIV-1 were obtained by co-culture with normal donor PBMCs. Fang et al. (1995). Viral isolates were titrated in PBMCs (Fang et al. (1995)). Biological clones were derived from primary isolates by short-term limiting dilution cloning (Connor et al. (1997)).

Patient Population and Response to Therapy

Initially, most of the fifteen women displayed high plasma HIV-1 RNA levels and CD4+ cell depletion (means of 5.22 $\log_{10}$ copies/ml and 147 cells/mm$^3$, respectively). At that time, eight women were receiving antiretroviral therapy, primarily zidovudine monotherapy. While under study, however, 12 initiated new combination regimens; 9 received HAART (Group I) and 3 received two or more nucleoside analogues (Group II). Three individuals, by contrast, did not initiate new therapy during the study (Group III) (Table 1). In Table 1, "Before therapy" refers to data obtained at the visit immediately preceding initiation of new two or three drug antiretroviral therapy in Groups I & II. For Group III, data from the first time point are shown (a). "Follow-up" refers to data obtained at the first time point following the initiation of the anti-HIV therapy listed for Groups I & II. For Group III, data from the final time point are displayed (b). Comparisons of QXR before and after initiation of new, combination antiretroviral therapy were statistically significant for Group I, HAART recipients (c), (P=0.023) and Groups I & II combined, consisting of all treated patients (P=0.003).

TABLE 1

| | Patient Characteristics Before and After Antiretroviral Therapy | | | | | | | |
|---|---|---|---|---|---|---|---|---|
| | Status Before Combination Therapy[a] | | | | Follow-up Status[b] | | | |
| Pt. | HIV-1 RNA, log copies per ml | CD4+ count, cells per mm3 | Anti-HIV Therapy | QXR, proportion of HIV-1 Using R5 | HIV-1 RNA, log copies per ml | CD4+ count, cells per mm3 | Anti-HIV Therapy | QXR, proportion of HIV-1 Using R5 |
| | | | Group I: HAART Recipients | | | | | |
| 1 | 5.30 | 188 | AZT | 0.36 | 5.08 | 578 | 3TC, d4T, Nel | 1.00 |
| 2 | 5.69 | 3 | None | 0.00 | 3.41 | 90 | 3TC, d4T, Nel | 1.00 |
| 3 | 5.75 | 291 | None | 0.34 | 4.54 | 370 | AZT, 3TC. Saq | 0.45 |
| 4 | 5.28 | 9 | d4T | 0.36 | 3.08 | 15 | 3TC, d4T, Rit | 0.36 |
| 5 | 6.08 | 41 | None | 0.36 | 4.96 | 11 | 3TC, d4T, Saq | 0.90 |
| 6 | 5.11 | 19 | None | 0.45 | 3.70 | 24 | 3TC, d4T, Ind | 1.00 |
| 7 | 4.94 | 42 | AZT | 0.36 | 5.61 | 10 | 3TC, d4T, Ind | 0.36 |
| 8 | 5.65 | 0 | AZT, ddl | 0.44 | 5.29 | 23 | 3TC, d4T, Ind | 1.00 |
| 9 | 5.58 | 259 | AZT | 0.90 | 4.86 | 282 | 3TC, d4T, Ind | 1.00 |

TABLE 1-continued

Patient Characteristics Before and After Antiretroviral Therapy

| | Status Before Combination Therapy[a] | | | | Follow-up Status[b] | | | |
|---|---|---|---|---|---|---|---|---|
| Pt. | HIV-1 RNA, log copies per ml | CD4+ count, cells per mm3 | Anti-HIV Therapy | QXR, proportion of HIV-1 Using R5 | HIV-1 RNA, log copies per ml | CD4+ count, cells per mm3 | Anti-HIV Therapy | QXR, proportion of HIV-1 Using R5 |
| Group II: Recipients of Combination Antiretroviral Therapy | | | | | | | | |
| 10 | 5.04 | 307 | AZT | 0.00 | 4.58 | 378 | 3TC, ddI | 1.00 |
| 11 | 5.10 | 222 | AZT, ddI | 0.00 | 4.94 | 213 | AZT, 3TC, d4T | 0.36 |
| 12 | 5.04 | 251 | None | 0.36 | 4.23 | 345 | AZT, 3TC | 1.00 |
| Group III: Recipients of No Therapy or AZT Monotherapy | | | | | | | | |
| 13 | 4.32 | 191 | None | 0.45 | 4.13 | 184 | None | 0.36 |
| 14 | 4.28 | 670 | None | 0.52 | 3.83 | 429 | None | 0.36 |
| 15 | 5.23 | 43 | AZT | 0.00 | 5.36 | NA | None | 0.00 |
| Mean Values for Treatment Groups | | | | | | | | |
| Group I | 5.49 | 94 | | 0.40 | 4.50 | 155 | | 0.74[c] |
| Group II | 5.06 | 260 | | 0.12 | 4.58 | 312 | | 0.79 |
| Group I & II, Combined | 5.38 | 136 | | 0.33 | 4.52 | 194 | | 0.75[c] |
| Group III | 4.61 | 301 | | 0.32 | 4.44 | 307 | | 0.24 |

For those initiating new therapy, HIV-1 RNA levels dropped by an average of 0.86 $\log_{10}$ copies/ml and CD4+ counts increased by an average of 58 cells/ml by the first study visit after starting the new regimens. The viral levels rebounded by 0.69 $\log_{10}$ copies/ml, however, by the end of the 28.5 month mean follow-up period for treated patients, at which time 11 of the 12 women continued to take antiretroviral therapy (6 HAART, 5 two drug regimens).

Assay for Coreceptor Use

Changes in coreceptor use of primary HIV-1 isolates and biological clones obtained from participants in the study over time were followed by using a HOS-CD4+ cell system. The parental HOS-CD4+ line is a human osteogenic sarcoma cell line stably expressing high levels of CD4. HOS-CD4+ cells transfected with genes encoding either CCR5 or CXCR4 in addition to CD4 (cell lines HOS-CD4.CCR5 and HOS-CD4.CXCR4 respectively) served as indicator lines for coreceptor use. Deng et al. (1996). To determine coreceptor use, HOS-CD4.CCR5 and HOS-CD4.CXCR4 cells were seeded onto 12-well plates and, after 24 hours, inoculated with a standard quantity of titered virus; $10^2$ TCID$_{50}$ of first passage primary viral isolates or biological clones were assayed in duplicate. HIV JR-FL and LAV/HTLV-IIIB inoculated in parallel as CCR5- and CXCR4-specific positive control viruses, respectively, and uninoculated cells were used as negative controls. To eliminate any artifacts resulting from infection via low levels of endogenous coreceptor expression, parental HOS-CD4+ cells were also inoculated with duplicate primary and control isolates.

Supernatants were harvested at day 10 after infection and analyzed for HIV-1 p24 antigen using a commercially available ELISA assay (NEN Life Science Products, Boston). ELISA values were standardized so that 0 pg/ml was set at the level equal to three times the mean value of the negative controls. A culture was considered positive if the p24 antigen level was equal to or greater than 25 pg/ml. Experimental results were discarded if: 1) any parental HOS-CD4+ culture tested positive; or 2) any JR-FL or LAV/HTLV-IIIB positive control culture tested negative. If the variance in p24 antigen level between duplicate cultures was greater than 25%, the coreceptor use assay for that particular viral isolate was repeated. Results of the coreceptor use assay were then categorized in a semiquantitative manner according to p24 antigen level as follows: negative (p24<25 pg/ml), +/−(25-50 pg/ml), 1+(50-250 pg/ml), 2+(250-500 pg/ml), and 3+($\geq$500 pg/ml).

Phenotypic Characterization

The presence of syncytium-inducing (SI) variants of HIV-1 in patient primary viral isolates was determined by infection of MT-2 cell cultures as previously described (Koot et al. (1993)). A pooled stock of HIV LAV/HTLVIII was used as a positive control.

Example 2

Antiretroviral Therapy Preferentially Suppresses CXCR4 Strains

Fourteen women initially displayed viral populations composed of both CCR5 and CXCR4 viruses (FIG. 1) and one displayed virus that exclusively used CXCR4. CXCR4 viruses persisted at subsequent time points in patients who did not initiate new combination therapy, a finding exemplified in FIG. 1 by Patient 13, who remained untreated throughout the study, and Patients 1, 2, and 8, whose virus was sampled on multiple occasions before new therapy commenced. Viruses using CXCR4 appeared to be preferentially suppressed, however, when new regimens were initiated. Not only were CXCR4 strains eliminated by the first time point after starting new therapy in half of the treated women (FIG. 1, Patients 1, 2, 6, 8, and 10), but the proportion of these viruses seemed to be diminished in most of the others. In addition, patients who experienced a rebound in HIV-1 RNA levels and CXCR4 strains while on therapy often achieved suppression of CXCR4 strains a second time when the antiretroviral regimen was changed (FIG. 1, Patients 2 and 8).

Coreceptor Use by Biologically Cloned Viruses

Delineation of the proportion of individual viruses using each coreceptor was prompted by two aspects of the pattern of HIV-1 coreceptor use in these individuals. First, analyses of primary viral isolates by the HOS-CD4+ system indicated coreceptor use by both CCR5 and CXCR4 viruses at many time points (FIG. 1). Because primary isolates comprise a molecular mixture of viral quasispecies, inventors wished to determine whether use of both coreceptors was due to dual tropic viruses or a mixture of individual viruses with CCR5 and CXCR4 tropisms. In addition, to compare coreceptor use rigorously over time, it is desirable to quantitate the proportion of virus using each coreceptor. For these reasons, biologic clones, which were derived from the patients' primary isolates by performing limiting dilution cultures, were isolated. Coreceptor use was then determined for 25 clones from each isolate by employing the HOS-CD4+ cell system. Biologic clones from these patients used either CCR5 or CXCR4; no dual tropic viruses were detected among the 525 clones by using our assay system. In addition, the distribution of coreceptor use by the clones generally confirmed the semiquantitative results obtained for primary isolates; proportions of HIV-1 using each coreceptor appeared roughly similar whether the cloned virus or primary isolates were examined (Table 2A, HIV-1 coreceptor use in primary viral isolates and biologic clones).

TABLE 2A

| Pt | Months After Baseline | Treatment | Co-Receptor Use of Primary Viral Isolates | | Distribution of Co-Receptor Use by Biologic Clones | |
|---|---|---|---|---|---|---|
| | | | CCR5 | CXCR4 | CCR5 | CXCR4 |
| 2 | 16 | AZT, 3TC | +++ | +++ | 8 | 17 |
| | 18 | HAART | + | − | 25 | 0 |
| | 26 | HAART | + | +++ | 4 | 21 |
| 5 | 0 | None | ++ | +++ | 11 | 14 |
| | 6 | HAART | +++ | + | 21 | 4 |
| | 9 | d4T, Ind | +++ | +++ | 10 | 15 |
| | 16 | HAART | +++ | − | 25 | 0 |
| 14 | 0 | None | +++ | ++ | 13 | 12 |
| | 7 | None | +++ | +++ | 9 | 16 |

In Table 2A coreceptor use was determined for the primary viral isolate obtained at each time point and for 25 biologic clones derived from each isolate.

Studies of biologic clones obtained at serial time points also confirmed that the predominant viral population shifted from CXCR4 to the less pathogenic CCR5 after initiating a change in the regimen of combination antiretroviral therapy (Table 2A). For example, analyses of virus obtained from Patient 2 sixteen months after baseline and eight months after initiation of double therapy showed only eight clones that used CCR5 as compared to seventeen that used CXCR4. After a switch to a HAART regime that included two new drugs, however, the viral population in this patient shifted and all 25 biologic clones used CCR5. A similar pattern was exhibited by biologic clones from Patient 5, whose virus shifted dramatically to CCR5 on the two occasions that HAART was initiated. Patient 14, by contrast, remained untreated and her viral population evolved to comprise a larger proportion of clones using CXCR4 over time.

The MT2 assay to detect SI viruses in culture was also performed on primary isolates derived at each time point. These results confirmed the pattern of HIV-1 coreceptor use described here. Thirteen of the fifteen patients were infected initially with SI virus. In all eleven of those who displayed SI virus and received new combination therapy, the phenotype changed at least transiently to non-syncytia inducing (NSI) after treatment (data not shown).

Sequence Analyses of the HIV-1 V3 Loop

HIV-1 virions were isolated from plasma samples as described (Fang et al. (1996) J. AIDS Hum. Retro. 12:352-7). Reverse transcriptase polymerase chain reaction amplification produced a 920-bp amplicon spanning the V3 region of the env gene. Reaction conditions were controlled rigorously to minimize recombination and other artifacts (Fang et al. (1996)). Amplified products were cloned into a TOPO™ TA vector (Invitrogen, Carlsbad, Calif.), verified by restriction digestion, and sequenced. Alignment of the sequences was initially done using the PILEUP program in the GCG Suite (Genetics Computer Group, Madison, Wis.), then checked manually. Envelope sequences were used to predict coreceptor use on the basis of the overall charge of the V3 loop and the presence of basic or acidic residues at positions 275 and 287 of the env gene (Bhattacharyya et al. (1996); and Hung et al. (1999)).

Coreceptor Use Determined by Sequence Analysis of HIV-1 RNA Molecular Clones

These sequences predicted a pattern of coreceptor use that essentially paralleled the one obtained by using viral culture (Table 2B, Coreceptor use determined by cocultivation of PBMCs vs. sequence analysis of plasma HIV-1 RNA). Table 2B shows a comparison of coreceptor use over time determined by two methods in representative study patients. At each time point, coreceptor use was assayed by co-cultivating PBMCs and determining the V3 loop sequence of virion-derived HIV-1 RNA.

The sequence data underscored the change in coreceptor use seen after initiation of treatment. These experiments suggest that study of cultivated virus reflects the coreceptor use of currently replicating virus and is likely to reveal the shifts in viral populations that occur as a result of recent antiretroviral therapy.

TABLE 2B

| Pt | Months After Baseline | Treatment | Co-Receptor Use by Cocultivated Virus | | Distribution of Co-Receptor Use Predicted by V3 Loop Sequences | | Total # of Clones |
|---|---|---|---|---|---|---|---|
| | | | CCR5 | CXCR4 | CCR5 | CXCR4 | |
| 1 | 6 | AZT | +++ | +++ | 9 | 4 | 13 |
| | 33 | HAART | +++ | − | 13 | 0 | 13 |
| | 36 | HAART | +++ | + | 8 | 2 | 10 |
| 2 | 16 | AZT, 3TC | +++ | +++ | 1 | 13 | 14 |
| | 22 | HAART | + | ++ | 0 | 13 | 13 |
| | 26 | HAART | + | +++ | 3 | 8 | 11 |
| 5 | 0 | None | ++ | +++ | 2 | 10 | 12 |
| | 6 | HAART | +++ | + | 8 | 3 | 11 |
| | 9 | d4T, Ind | +++ | +++ | 2 | 10 | 12 |
| | 16 | HAART | +++ | − | 12 | 0 | 12 |
| 14 | 0 | None | +++ | ++ | 5 | 6 | 11 |

Statistical Methods

The Wilcoxon Rank Sum Test was used to make comparisons between the magnitude of log viral level, CD4+ counts, and QXR values. Data for factors relating to changes in QXR values were analyzed by multivariate Poisson regression. Variables included log HIV-1 RNA levels, changes in viral levels, CD4+ cell counts, changes in CD4+ cell counts, and indicator variables for levels of antiretroviral therapy.

To quantitate HIV-1 coreceptor use, inventors constructed a variable, λ, as the proportion of strains using CCR5. This variable has since been renamed QXR. QXR=1 represents an isolate in which all strains prefer the CCR5 coreceptor but QXR=0 indicates that all prefer CXCR4. QXR values were assessed by utilizing qualitative assay data derived from primary isolates, biologic clones, and sequences of the V3 portion of the env gene. In determination of the coreceptor use of 525 biologic clones, none was dual tropic, suggesting that true dual tropic viruses are rare when using our assay method. It was therefore assumed for this calculation that the probability of a single virion possessing the phenotypic attributes of both coreceptors is small. Thus, for the vast majority of virions, each virion uses either CCR5 or CXCR4. This relationship can be stated as a mixture $$D = QXR(CCR5) + (1-QXR)(CXCR4); 0 \leq QXR \leq 1,$$

where D is the distribution of viral phenotypes. By design, it is a binomial population.

QXR values were constructed by relating data derived from the same patient sample by using three different analyses: biologic cloning, V3 sequencing of patient-derived molecular clones, and qualitative assays of primary isolates. To construct QXR values, inventors first calculated the proportion of biologic and, if available, molecular clones using CCR5 at each time point, then linked the proportion to the qualitative coreceptor use score (− to 3+) of primary isolates obtained simultaneously. Data that were not available were interpolated. The data were transformed to approximate a Poisson distribution. Poisson regression analysis was then performed to determine the factors associated with changes in QXR values.

Quantitation of Coreceptor Use by CCR5 and CXCR4

The large number of biologic and molecular clones permitted derivation of a system to quantitate the proportion of virus in a clinical specimen that uses each coreceptor. In this system, QXR is a continuous, nonlinear variable between one and zero derived from the results presented here showing coreceptor use by biologically and molecularly cloned virus; it describes the mixed proportion of viruses using CCR5 and CXCR4. A QXR value near one describes a population of viruses that almost all use CCR5; a value near zero describes a population that almost all use CXCR4. By applying this method, it was determined the proportion of virus using each coreceptor for each patient over time.

To quantitate the effect of combination therapy on HIV-1 coreceptor use, inventors compared the QXR values of virus obtained at the visits before and immediately after initiating new combination therapy. This comparison demonstrated a clear, statistically significant shift of the predominant viral population from CXCR4 to CCR5 (Table 1). The mean QXR values for virus from all twelve patients starting combination therapy (Groups I & II) changed from 0.33 to 0.75 (P=0.003 by using the binomial proportion comparison test). For the subset of nine who initiated HAART (Group I), the shift in QXR extended from 0.40 to 0.74 (P=0.023). In addition, inventors assessed separately the effect of initiating treatment with two or more nucleoside analogues and no protease inhibitor on coreceptor use. Five of the patients who ultimately received HAART had received regimens consisting of two nucleoside analogues previously. The QXR values of virus obtained before or after initiation of two or more nucleoside analogues in a group of eight patients (Group II and Patients 1, 2, 6, 7, and 9) were compared; in this group the QXR values changed from 0.30 to 0.84 (P=0.008). By contrast, in the Group III patients, who did not initiate combination therapy, the mean QXR value decreased from 0.32 to 0.24 during the course of this study. These numerical comparisons of coreceptor use demonstrated a shift in the predominant viral population from CXCR4 to CCR5 following initiation of a variety of combination antiretroviral regimens.

Long-term Analysis of Antiretroviral Therapy, Viral Level, and CD4+ Cell Count Effects on Coreceptor Use The period of follow-up for treated women in this study averaged 28.5 months, during which their coreceptor use, plasma HIV-1 RNA levels, and CD4+ cell count varied, sometimes in concert (FIG. 1). The mulitvariate regression indicated that antiretroviral therapy with two or more drugs was by far the most significant factor in determining QXR, the numerical expression of the proportion of viruses using CCR5 (P=0.01). Although changes in viral level and CD4+ cell count had a significant effect on QXR in univariate analysis, they lost all significance when considered in a multivariate regression analysis with antiretroviral therapy. The strength of the relationship between initiation of therapy and shift in HIV-1 coreceptor use is reflected in the course of treated individuals like Patient 8, who maintained high plasma HIV-1 RNA levels during treatment but demonstrated a substantial, long-term shift in viral population toward CCR5 (FIG. 1).

Example 3

Dynamics of HIV-1 Coreceptor Utilization Switch

Figure 2:
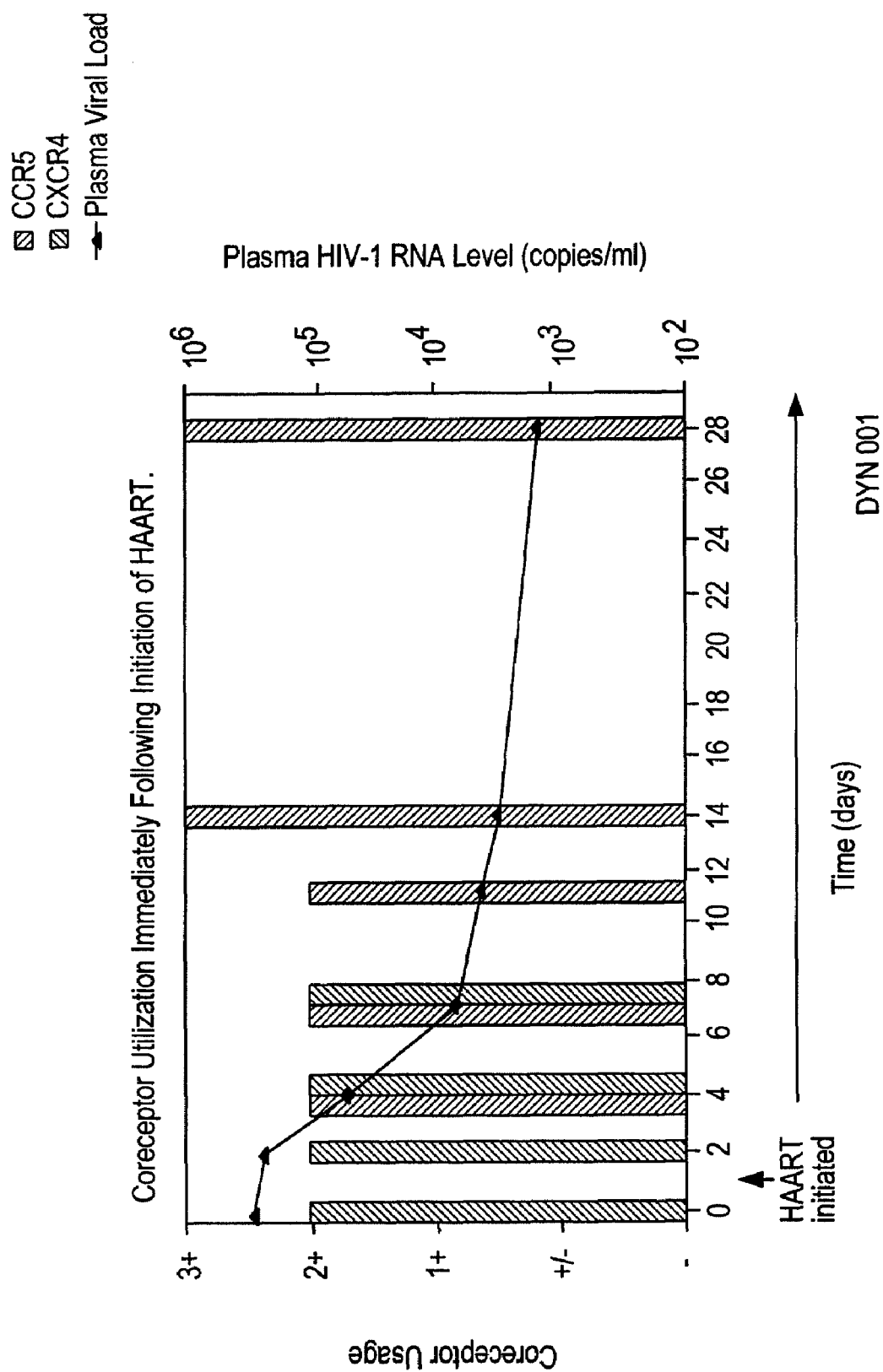
FIG. 2 depicts the dynamics of the shift in coreceptor utilization immediately following initiation of HAART.

The dynamics of the shift in coreceptor utilization immediately following initiation of HAART have been characterized. Coreceptor utilization immediately following the initiation of HAART was determined by studying virus derived from the patient's PBMC's. Results show the following: 1) this patient was unusual in that her initial viral population was composed of X4 viruses only, 2) by the third day after the initiation of HAART, the viral population had switched to equal proportions of X4 and R5 using strains, and 3) by day 11, the population had entirely switched to R5 using virus (FIG. 2).

Comparison of coreceptor usage in this patient was also performed using a recombinant assay that does not require culturable primary isolates. The results of the recombinant assay were identical to the results obtained using virus derived from the patient's PBMC's. These data document a rapid, complete switch in coreceptor utilization by virus in peripheral blood that occurred less than two weeks after initiating HAART. To understand the complexities of HIV-1 pathogenesis, it is necessary to consider the heterogeneity of viral populations and viral reservoirs. This approach will provide insight into the dynamics of suppressing different populations of virus.

Example 4

Rapid Cell Fusion Assay for Coreceptor Utilization

Viral coreceptor usage was separately evaluated through the use of a Rapid Cell Fusion Assay. This assay enables determination of coreceptor usage from cloned HIV env gene sequences obtained directly from patient samples (e.g. blood, mucosal tissue). This method allows for greater efficiency in determination of viral coreceptor usage, by circumventing the need for cultivation of primary isolates. The Rapid Cell Fusion Assay can advantageously produce a result within one week after obtaining a patient sample. In addition, the Rapid Cell Fusion Assay allows study of patient-derived virus obtained from sites other than the peripheral blood, particularly those sites from which cultured virus cannot be obtained. For example, while circulating macrophages and CD4+ T cells are the dominant reservoir of HIV-1, viral populations distinct from those in the peripheral blood exist in many reservoirs, including the genital tract. It is important to study these different reservoirs as HIV-1 viral populations in infected individuals demonstrate marked heterogeneity, with virus varying in the same compartment over time and in different compartments contemporaneously (Myers et al. (1995); Meyerhans et al. (1989); Vernazza et al. (1994); Cheng-Mayer et al. (1989); Koyanagi et al. (1987); ); Kemal et al. (2003)). Even in patients receiving combination anti-HIV-1 therapy, studies of lymphoid tissue reservoirs showed persistent viral replication in lymph nodes, with viral load in tissue exceeding that in plasma by orders of magnitude in most cases (Wong et al. (1997); Cavert et al. (1997); Haase et al. (1996)).

Steps of the Rapid Cell Fusion Assay

The HL3T1 cell line was derived by stable transfection of parental HeLa cells with a chloramphenicol acetyltransferse (CAT) reporter construct containing a CAT gene is linked to an HIV-1 LTR promoter. The HL3T1 cells produce CAT protein only upon introduction of an active HIV-1 Tat protein. HL3T1 cells were transfected with a cloned env gene derived from a patient of interest. The cloned env gene product is expressed on the surface of the HL3T1 cells.

Indicator cell lines GHOST.CCR5 and GHOST.CXCR4 (respectively hereinafter "R5-tat" and "X4-tat") cells were transfected with pSV2tat72, a construct expressing high levels of HIV-1 Tat under the control of the SV40 early promoter.

HL3T1 cells containing a cloned patient env gene were fused to R5-tat and X4-tat cells. Cell surface envelope protein variants will selectively interact with either CCR5 or CXCR4. Fusion only occurs when an HL3T1 envelope protein interacts with an indicator cell expressing a compatible coreceptor. Therefore, HL3T1 cells will fuse with either R5-tat and X4-tat, depending on the patient's env gene specificity. To initiate fusion, transfected HL3T1 and R5-tat or X4-tat cells were mixed in 6-well plates at 37° C. and allowed to fuse for 48 hours. To quantitate fusion, the cells were lysed with 0.5% NP-40. Fusion of HL3T1 cells to R5-tat or X4-tat activated CAT gene expression. Aliquots of the cell lysates were monitored for CAT production using a commercially available kit (CAT-ELISA, Boehringer Mannheim).

Twenty-five clones from each sample were analyzed to ensure that the fusion assay reflected the heterogeneous nature of HIV-1 populations. Sample results of the Rapid Cell Fusion Assay for Coreceptor Utilization are presented below. For all env clones assayed in this manner, sequence analysis has revealed a 97% correlation between coreceptor usage and predicted env genotype.

| CLONE | V3 LOOP SEQUENCE | CORECEPTOR | |
|---|---|---|---|
| AF2P12-1 | CIRPNNNTRTSIRIGPGQAFYATGNIIGDIRQAYC | CCR5 | (SEQ ID No.1) |
| AF2P12-2 | CIRPNNNTRTSIRIGPGQAFYATGNIIGGIRQAYC | CCR5 | (SEQ ID NO.35) |
| AF2P12-3 | CIRPNNNTRTSIRIGPGQAFYATGNIIGDIRQAYC | CCR5 | (SEQ ID NO.1) |
| AF2P12-4 | CIRPNNNTRTSIRIGPGQAFYATGNIIGDIRQAYC | CCR5 | (SEQ ID NO.1) |
| AF2P12-6 | CIRPNNNTRTSIRIGPGQAFYATGNIIGDIRQAYC | CCR5 | (SEQ ID NO.1) |
| AF2P12-8 | CIRPNNNTRTSIRIGPGQAFYATGNIIGDIRQAYC | CCR5 | (SEQ ID NO.1) |
| AF2P12-9 | CIRPNNNTRTSIRIGPGQAFYATGNIIGDIRQAYC | CCR5 | (SEQ ID NO.1) |
| AF2P12-10 | CIRPNNNTRTSIRIGPRQAFYATGNIIGDIRQAYC | CXCR4 | (SEQ ID No.2) |
| AF2P12-11 | CIRPNNNTRTSIRIGPGQAFYATGNIVGDIRQAYC | CCR5 | (SEQ ID NO.3) |
| AF2P12-12 | CIRPNNNTRTSIRIGPGQAFYATGNIIGDIRQAYC | CCR5 | (SEQ ID NO.1) |
| AF3P-2 | ........RKSVHIGPGQAFYATGDIIGNIRKAHC | negative | (SEQ ID NO.4) |
| AF3P-4 | CTRPNNNTRKSVHIGPGQAFYATGDIIGNIRKAHC | CCR5 | (SEQ ID NO.5) |
| AF3P-5 | CTRPNNNTRKSVHIGPGQAFYATGDIIGNIRKANC | CCR5 | (SEQ ID NO.5) |
| AF3P-6 | CTRPNNNTRKSVHIGPGQAFYATGDIIGNIRKAHC | CCR5 | (SEQ ID NO.6) |
| AF3P-7 | CTRPNNNTRKSVHIGPGQAFYATGDIIGNIRKAHC | CCR5 | (SEQ ID NO.5) |
| AF3P-8 | CTRPNNNTRKSVHIGPGQAFYATGDIIGNIRKAHC | CCR5 | (SEQ ID NO.5) |
| AF3P-9 | CTRPNNNTRKSVHIGLGQAFYATGDIIGNIRKAHC | CCR5 | (SEQ ID NO.36) |
| AF3P-10 | CTRPNNNTRKSVHIGPGQAFYATGDIIGNIRKAHC | CCR5 | (SEQ ID NO.5) |
| AF3P-11 | CTRPNNNTRKSVHIGPGQAFYATGDILGNIRQAHC | CCR5 | (SEQ ID NO.37) |
| AF3P-12 | CTRPNNNTRKSVHIGPGQAFYATGDIIGNMRKAHC | CCR5 | (SEQ ID NO.7) |
| AF5P-5 | CTRPNNNTRKSVHIGPGQAFYATGDIIGDIRQAYC | CCR5 | (SEQ ID NO.38) |
| AF5P-6 | CTRPNNNTKKSVHIGPGQAFYATGDIIGDIRQAYC | CCR5 | (SEQ ID NO.39) |
| AF5P-8 | CTRPNNNTRKSVHIGPGQAFYATGDIIGDIRQAYC | CCR5 | (SEQ ID NO.38) |
| AF6P-1 | CTRPINNRRKSIHMGPGQAFYGT.DDIIGDIRKARC | CCR5 | (SEQ ID NO.8) |
| AFGP-3 | CTRPINNRRKSIHMGPGQAFYGT.DDIIGDIRKARC | CCR5 | (SEQ ID NO.8) |
| AF6P-7 | CTRPSNNRRKSIHKGDQDKHSMEHDDVIGDIRKARC | negative | (SEQ ID NO.9) |
| AF6P-9 | CTRPINNRRKSIHMGPGQAFYGT.DDIIGDIRKARC | CCR5 | (SEQ ID NO.8) |
| AFGP-10 | CTRPINNRRKSIHIGPGQAFYGT.DDIIGDIRQAHC | CCR5 | (SEQ ID NO.32) |
| AFGP-11 | CTRPSNNRRKSIHMGPGQAFYGT.DDIIGGIRKARC | CCR5 | (SEQ ID NO.33) |
| AF6P-12 | CTRPSNNRRKSIHMGPGQAFYGT.DDIIGDIRKARC | CCR5 | (SEQ ID NO.34) |
| AF7P-9 | CIRPNNNTRQSVHIGPGQALYTTEIIGDIRKAHC | CCR5 | (SEQ ID NO.11) |
| AF7P-12 | CIRPNNNTRQSVHIGPGQALYTTEIIGDIRKAHC | CCR5 | (SEQ ID NO.11) |
| AF9P2-3 | CTRPNNNTITSIRIGPGQAFYATGSIIGNIRQAHC | CCR5 | (SEQ ID NO.12) |
| AF9P2-4 | CTRPNNNTITSIRIGPGQAFYATGSIIGNTRQAHC | CCR5 | (SEQ ID NO.13) |
| AF9P2-7 | CTRPNNNTITSIRIGPGQAFYATGSIIGNIRQAHC | CCR5 | (SEQ ID NO.12) |
| AF9P2-9 | CTRPNNNTITSIRIGPGQAFYATGSIIGNIRQAHC | CCR5 | (SEQ ID No.12) |
| AF9P2-10 | CTRPNNNTITSIRIGPGQAFYATGSIIGNIRQAHC | CCR5 | (SEQ ID NO.12) |

-continued

| CLONE | V3 LOOP SEQUENCE | CORECEPTOR | |
|---|---|---|---|
| AF9P2-11 | CTRPNNNTITSIRIGPGQAFYATGSIIGNIRQAHC | CCR5 | (SEQ ID NO.12) |
| AF9P2-12 | CTRPNNNTITSIRIGPGQAFYATGSIIGNIRQAHC | CCR5 | (SEQ ID NO.12) |
| AF10P97-2 | CTRPNDNIRKSVHIGPGQAFYATGDIIGDIRRAHC | CCR5 | (SEQ ID NO.14) |
| AF10P97-4 | CTRPNDNIRKRVHIGPGQAFYATGDVIGDIRRAHC | CXCR4 | (SEQ ID NO.40) |
| AF10P97-6 | CTRPNDNIRKSVHIGPGQAFYATGDIIGDIRRAHC | CCR5 | (SEQ ID NO.14) |
| AF10P97-11 | CTRPNDNIRKSVHIGPGQAFYATGDIIGDIRRAHC | CCR5 | (SEQ ID NO.14) |

Figure 3:
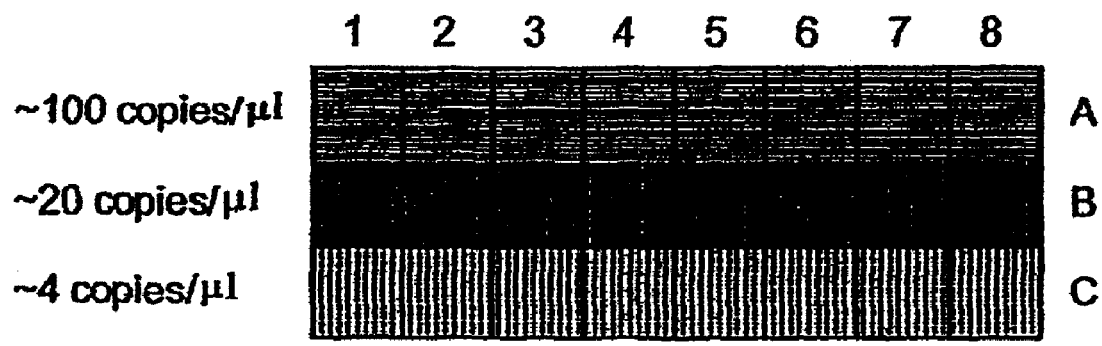
FIG. 3 depicts an example of a template set-up for a PE2400 PCR tray-retainer.

Sequence Identifiers (SEQ ID NO:1)  CIRPNNNTRTSIRIGPGQAFYATGNIIGDIRQAYC (SEQ ID NO:2)  CIRPNNNTRTSIRIGPRQAFYATGNIIGDIRQAYC (SEQ ID NO:3)  CIRPNNNTRTSIRIGPGQAFYATGNIVGDIRQAYC (SEQ ID NO:4)  RKSVHIGPGQAFYATGDIIGNIRKAHC (SEQ ID NO:5)  CTRPNNNTRKSVHIGPGQAFYATGDIIGNIRKAHC (SEQ ID NO:6)  CTRPNNNTRKSVHIGPGQAFYATGDIIGNIRQAHC (SEQ ID NO:7)  CTRPNNNTRKSVHIGPGQAFYATGDIIGNMRKAHC (SEQ ID NO:8)  CTRPINNRRKSIHMGPGQAFYGT.DDIIGDIRKARC (SEQ ID NO:9)  CTRPSNNRRKSIHKGDQDKHSMEHDDVIGDIRKARC (SEQ ID NO:10) CTRPINNRRKSIHIGPGQAFYGT.DDIIGDIRQAHC (SEQ ID NO:11) CIRPNNNTRQSVHIGPGQALYTTEIIGDIRKAHC (SEQ ID NO:12) CTRPNNNTITSIRIGPGQAFYATGSIIGNIRQAHC (SEQ ID NO:13) CTRPNNNTITSIRIGPGQAFYATGSIIGNTRQAHC (SEQ ID NO:14) CTRPNDNIRKSVHIGPGQAFYATGDIIGDIRRAHC Methods of env Gene Cloning In cloning the env gene from patients by the use of long RT-PCR, two potential problems may result: 1) recombination between molecules; and 2) underestimates of sequence diversity. High fidelity cloning of the samples above was achieved by routine performance of multiple RT reactions on limiting dilutions of RNA, followed by multiple PCR's on cDNAs obtained from each RT reaction. Performance of multiple PCR's on each cDNA preparation increased the likelihood of amplifying a different HIV-1 RNA species. These measures also decrease the chance of recombination. Accordingly, the following protocol was developed:

1. Peripheral blood was collected and separate into plasma and cell components. Other fluids and tissues derived from an HIV-infected individual can also be used, with minor modifications to the RNA extraction protocol outlined below.
2. HIV-1 RNA was quantitated in plasma by using NucliSens (Organon Teknika Corp., Durham, N.C.), with a lower limit of quantitation set at approximately 80 copies/ml.
3. RNA extraction:
   a) HIV-1 RNA was extracted from plasma using Qiagen's Viral RNA Kit and following the manufacturer's standard protocol.
   b) Samples were standardized by extracting a volume of plasma equal to 10000 copies of HIV-1 RNA. For example, if the patient's plasma viral load is 25000 copies/ml, 0.4 ml of plasma in the extraction should be used.
   c) Following extraction, the virus was resuspended in 100 ul of Rnase-free water (to give a final concentration of <100 copies of HIV-1 RNA per ul) and optionally treated with Rnase-free Dnase to remove any contaminating DNA.
4. RT-PCR using limiting dilution to ensure minority species amplification:
   a) Samples of serially diluted RNA template were generated in a series of 1:5 dilutions using the following template concentrations:
      ~100 copies/µl
      ~20 copies/µl
      ~4 copies/µl
      This dilution series is sufficient to ensure minority species amplification. Conditions are adaptable to achieve limiting dilutions.
   b) 1 ul aliquots of RNA template were distributed into the wells of a PE2400 or PE9700 PCR tray-retainer and 8-24 tubes containing of each RNA dilution were prepared. An example of the template set-up for a PE2400 is shown in FIG. 3.
   c) An RT reaction mix was prepared:

| reagent | per reaction |
|---|---|
| Rnase-free H$_2$O | 2 ul |
| 10x PCRII buffer | 2 ul |
| 25 mM MgCl$_2$ | 4 ul |
| 10 mM dATP | 2 ul |

-continued

| reagent | per reaction |
|---|---|
| 10 mM dCTP | 2 ul |
| 10 mM dGTP | 2 ul |
| 10 mM dTTP | 2 ul |
| Rnase Inhibitor | 1 ul |
| 50 mM Random Hexamers | 1 ul |
| MMLV RT (50 U/ul) | 1 ul |

All reagents are commercially available from Perkin Elmer. Each well received a 19 ul aliquot. Samples were incubated for 60 minutes at 37° C., followed by heat inactivation for 5 minutes at 95° C. Samples were stored at 4° C.

d) The Primary PCR reaction mix was prepared:

| reagent | per reaction |
|---|---|
| sterile H$_2$O | 67.5 ul |
| 10x PCRII buffer | 8 ul |
| 25 mM MgCl$_2$ | 2 ul |
| primer HIVGao1F (20 uM) | 1 ul |
| primer HIVGao1R (20 uM) | 1 ul |
| Taq polymerase (50 U/ul) | 0.5 ul |

Primer sequences for HIVGao1F and HIVGao1R were:

(SEQ ID NO:15)
HIVGao1F: 5'-GGCTTAGGCATCTCCTATGGCAGGAAGAA-3'

(SEQ ID NO:16)
HIVGao1R: 5'-GGCTTAGGCATCTCCTATGGCAGGAAGAA-3'

80 ul aliquots were transferred into each well containing the RT mix. The cycle parameters were:

| Cycle file | Temp. | Time |
|---|---|---|
| 1 hold: | 94° C. | 5 minutes |
| 5 cycles: | 94° C. | 1 minute |
|  | 50° C. | 1 minute |
|  | 72° C. | 3.5 minute |
| 30 cycles: | 94° C. | 1 minute |
|  | 55° C. | 1 minute |
|  | 72° C. | 3.5 minute |
| 1 hold: | 72° C. | 10 minutes |
| 1 hold: | 4° C. | until ready for nested reaction | e) A nested PCR reaction mix was prepared:

| reagent | per reaction |
|---|---|
| sterile H$_2$O | 75.5 ul |
| 10x PCRII buffer | 10 ul |
| 25 mM MgCl$_2$ | 6 ul |
| 10 mM dNTP blend | 4 ul |
| primer HIVGao2F (20 uM) | 1 ul |
| primer HIVGao2R (20 uM) | 1 ul |
| Taq polymerase (50 U/ul) | 0.5 ul |

Primer sequences for HIVGao2F and HIVGao2R are:

(SEQ ID NO:17)
HIVGao2F: 5'-AGAAAGAGCAGAAGACAGTGGCAATGA-3'

(SEQ ID NO:18)
HIVGao2R: 5'-AGCCCTTCCAGTCCCCCCTTTTCTTTTA-3'

Each well of a new PE2400 base received a 98 ul aliquot, followed by 2 ul of each primary PCR reaction serving as a as template for the nested PCR reaction. The same cycle parameters as indicated for the primary PCR were applied.

Figure 4:
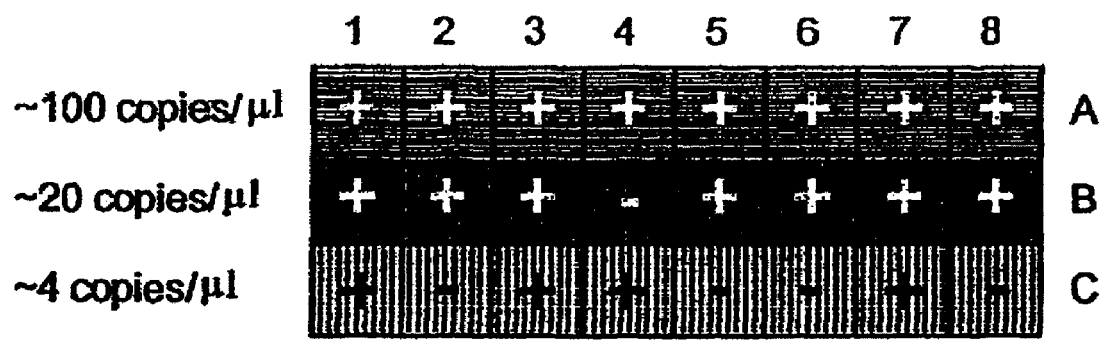
FIG. 4 depicts an example of a pattern produced by gel analysis based on an original RT layout, for use in selecting samples to be cloned/sequenced.

5. Gel analysis of RT-PCR products:
   a) 10 ul of each nested PCR product was run on a 1.5% agarose gel.
   b) Only the wells of the original RNA template dilution that produced approximately 50% positive wells were cloned/sequenced to ensure cloning/sequencing of an amplicion derived from a single RNA template molecule. For example, if gel analysis produced the following pattern based on the original RT layout, only the 4 positive wells of the last row (the 1:25 or ~4 copies/ul row) would be cloned/sequenced (FIG. 4.). All other positives were discarded.
   c) The chosen positives were either cloned or sent directly for sequencing.

6. Cloning of RT-PCR products:
   a) PCR reaction products were purified using Qiagen's Gel Extraction Kit according to the manufacturer's standard protocol.
   b) Amplicons were cloned into Promega's pTarget Mammalian Expression vector following a standard protocol, such as that which is included with the pTarget Kit. Each selected positive reaction was cloned once. In addition, only one clone from each plate was picked/analyzed to ensure that the minority species were fully represented
   c) Plasmid DNA was prepared according to standard procedures for ABI sequencing.

7. ABI sequencing of RT-PCR products or clones:
   a) Standard automated sequencing on an ABI 370 series sequencing machine was carried out. The following three primers were used to ensure complete redundant sequencing of the V3 loop of the envelope gene:

(SEQ ID NO:19)
NL6942F: 5'-GCACAGTACAATGTACACATG-3'

(SEQ ID NO:20)
NL7103F: 5'-ACAAGACCCAACAACAATACA-3'

(SEQ ID NO:21)
NL7356R: 5'-TGTATTGTTGTTGGGTCTTGT-3'

8. Sequence analysis:
   a) The DNA sequence of the env V3 loop was determined.
   b) Protein translation of the V3 loop was determined.
   c) CCR5 or CXCR4 predictions were based on the scheme outlined below:

```
Clade B    268              290
            |                |
consensus: NNTRK-I-IGPG-A---TG-II G (SEQ ID NOS: 22-25)

R5 strain if 1. G/S at residue 273 and D/E at residue 287 (SEQ ID NO: 22)
                 2. K,H,R at residue 275 and D/E at residue 287 (SEQ ID NO: 23)
                 3. Not K,H,R at residue 275 but D/E/K/H/R at residue 287 (SEQ Id NO: 24)
    X4 strain if: 1. K,H,R at residue 275 and K/H/R at residue 287 (SEQ ID NO: 25)
``` d) The QXR value for the patient was calculated as:

$QXR = (\# \text{ of } R5 \text{ clones})/(\text{total } \# \text{ of clones})$

Example 5

Qualitative HIV-1 Coreceptor Utilization Analysis using a Heteroduplex Tracking Assay (HTA)

Specimen Accession and Plasma Preparation

The purpose of this procedure is to describe the actions followed when receiving and preparing plasma specimens for HIV-1 coreceptor utilization analysis (QXR). Samples were removed from tubes in a sterile decontaminated hood. If lavender-top tubes of whole blood were sent, it was centrifuged at room temperature for 10 minutes at 1,100×g (2300 rpm). Tubes were removed from the centrifuge and checked for complete separation. The plasma layer was transferred to freezer vials.

If, instead, frozen plasma had been shipped, it was either transferred directly to −80° C. freezer to be aliquoted and/or extracted at a later time, or the plasma was thawed and transferred to appropriately labeled croyogenic tubes in 200 μl aliquots, stored at −80° C. in RNA box, and entered into Sample Storage Log. If RNA was to be isolated on the same day, 140 μl of plasma was transferred into a 1.5 ml screw-top conical base tube labeled with sample ID# and date. After the plasma had been removed, then the blood-draw tubes were discarded in appropriate waste containers for autoclaving.

Extraction of Viral RNA

The purpose of this procedure is to extract HIV-1 viral RNA from plasma. The extracted RNA is subsequently used for analysis of HIV-1 coreceptor utilization.

Plasma samples were thawed and equilibrated to room temperature. HIV-1 RNA was extracted from plasma using Qiagen's Viral RNA Kit and following the manufacturer's standard protocol. All buffers including Lysis Buffer (AVL), Wash Buffer 1 (AW1), and Wash Buffer 2 (AW2) were prepared according to manufacturer's instructions. Any precipitate in buffers was re-dissolved by heat incubation at 80° C. if necessary, but buffer was allowed to re-equilibrate to room temperature before proceeding. To avoid co-purification of cellular DNA, only cell-free body fluids should be used for preparation of viral RNA. Samples that may contain cells (e.g., cerebrospinal fluid, urine, or swabs) should first be centrifuged for 10 minutes at 2,000 rpm, and only the clarified supernatant used.

For patients samples with HIV-1 RNA loads<1.0×10$^5$ copies/ml, the plasma virions were pelleted by centrifuging the tubes for 90 minutes at 10,000×g at 4° C. All tubes to be used were labeled with the correct identifiers. 560 μl of Lysis Buffer (AVL) was pipetted into an appropriately labeled 1.5-ml screw-cap tube, then 140 μl plasma was added and mixed by pulse-vortexing for 15 seconds. Samples were lysed for at least 10 minutes at room temperature (although samples may be lysed for up to 24 hours at room temperature or 7 days at 4° C. without significant effect on the yield or quality of the purified RNA). The 1.5-ml screw-cap tubes were briefly centrifuged (2-3 seconds at 8,000 rpm) to remove drops from the inside of the lid. 560 μl of absolute ethanol was added and mixed by pulse-vortexing for 15 seconds. The 1.5-ml screw-cap tubes were briefly centrifuged (2-3 seconds at 8,000 rpm) to remove drops from the inside of the lid. 630 μl of the solution was carefully applied to an appropriately labeled QIAamp™ spin column. The sample or solution from the lysis tube was then carefully applied to the column or tube by pipetting the sample into the tube without wetting the rim or outside of the column. Tubes were centrifuged for 60 seconds at 6,000×g. The QIAamp™ spin columns were transferred into clean 2-ml collection tubes. The supernatant-containing collection tubes were discarded into a waste bucket. The remaining 630 μl of the solution was carefully applied, without wetting the rim or outside of the column, to an appropriately labeled QIAamp™ spin column. The tubes were centrifuged for 60 seconds at 6,000×g, and the QIAamp™ spin columns were transferred into clean 2-ml collection tubes. The supernatant-containing collection tubes were discarded into a waste bucket. The QIAamp™ spin columns were opened carefully and 500 μl of Wash Buffer 1 (AW1) was added. Tubes were centrifuged for 60 seconds at 6,000×g. The QIAamp™ spin columns were transferred into clean 2-ml collection tubes. The supernatant-containing collection tubes were discarded into a waste bucket. The QIAamp™ spin columns were carefully opened and 500 μl of Wash Buffer 2 (AW2) was added. Tubes were centrifuged for 3 minutes at 10,000×g. The supernatant was aspirated from the collection tubes using either a transfer pipettes or vacuum with trap. The pipette or tip was changed after each aspiration. Tubes were centrifuged for 60 seconds at 6,000×g to eliminate any chance of wash buffer carryover. The QIAamp™ spin columns were transferred into clean 1.5 ml microcentrifuge tubes. The supernatant-containing collection tubes were discarded into a waste bucket. 60 μl of Elution Buffer (AVE) was added to each column. The pipette tip was changed for each tube. The columns were incubated for 60 seconds at room temperature, followed by centrifugation for 60 seconds at 6,000×g. 10 μl of eluted ribonucleic acid was transferred into a new 1.5-ml screw-cap tube for coreceptor utilization analysis. The remaining viral RNA (~48-50 μl) was transferred into another 1.5-ml screw-cap tube for long-term storage at ≦−70° C.

Reverse Transcription (RT) and Polymerase Chain Reaction (PCR)

The purpose of this procedure was to amplify a portion of the envelope gene of Human Immunodeficiency Virus type 1 (HIV-1), using viral RNA extracted from plasma as template. The resulting RT-PCR amplicon was subsequently used for analysis of HIV-1 coreceptor utilization.

Two sets of PCR primers were used and are described in Table 3

TABLE 3

PCR primers

```
First Set   HTA6816F:
of Primers  5'-CCT CAG CCA TTA CAC AGG CCT GTC CAA
            AG-3'
            (SEQ ID NO:35)
            HTA7359R:
            5'-TTA CAG TAG AAA AAT TCC CCT C-3'
            (SEQ ID NO:36)

Second Set  V3-7092F:
of Primers  5'-GAA TCT GTA GAA ATT AAT TGT ACA AGA
            C-3'
            (SEQ ID NO:37)
            V3-7232R:
            5'-TGC TCT ACT AAT GTT ACA ATG TGC TTG
            TCT TAT-3'
            (SEQ ID NO:38)
```

Reverse Transcriptase (RT) Master Mix Preparation:

GeneAmp RNA OCR core Kit reagents were thawed to room temperature, except for enzymes, which were removed from freezer only when needed. Reagents were mixed by vortexing and then microcentrifuged briefly before placing tubes in an ice bucket. A sterile 1.5 ml microcentrifuge tube was placed in the ice bucket. Enough RT master mix was prepared to accommodate the number of planned reactions plus one (to accommodate pipetting eror), based on the following amounts of reagents per reaction: 2 µl 10×RT-PCR Buffer II, 4 µl 25 mM MgCl, 2 µL 10 mM dCTP, 2 µL 10 mM dGTP, 2 µL 10 mM dTTP, 2 µL 10 mM dATP, 1 µL 50 µM Random Hexamers, 1 µL Rnase Inhibitor (20 U/µl), 1 µL MuLV RT (50 U/µl). Master mix and retainer assembly was transferred to a sterile laminar flow hood.

RNA Template Addition:

Patient RNA was thawed on ice followed by brief microcentrifugation to ensure that all liquid is brought to the bottom. MicroAmp reaction tubes were labeled and placed in retainer/tray assembly. RT master mix was mixed by gently pipetting up and down a few times. 17 µl of master mix was pipetted into each of the reaction tubes. 3 µl of viral RNA extracted from patient samples was added. One extraction positive control (HIV-1 LAV) and one extraction negative control (Sera Care Plasma) were included with each RT-PCR run. Tubes were capped with cap strips and retainer/tray assembly was removed from the laminar flow hood and transferred to thermocycler. The RT reaction mixtures were incubated at 42° C. for 60 minutes followed by heat inactivation at 95° C. for 5 minutes. The completed RT reaction can be stored at 4° C. (short-term) or –20° C. (long-term) until ready for cDNA amplification.

Primary PCR Master Mix Preparation:

GeneAmp RNA PCR Core Kit reagenets were thawed at room temperature, except for enzymes, which were removed from freezer only when needed. Reagents were mixed by vortexing and then briefly microcentrifuged and placed in an ice bucket. A sterile 1.5 ml microcentrifuge tube was placed in the ice bucket. Enough cDNA amplification/primary PCR master mix was prepared to accommodate the number of planned reactions plus one (to accommodate pipetting error), based on the following amounts of reagents per reaction: 8 µL 10×PCR buffer II, 2 µL 25 mM MgCl$_2$, 1 µL of each primer (25 µM) (Table 3), 67.5 µL sterile water, and 0.5 µL Taq polymerise (5U/µL). Primary PCR master mix and retainer assembly containing completed RT reactions were transferred to sterile laminar flow hood in template addition area.

cDNA Template Addition:

PCR master mix was mixed by gently gently pipetting up and down a few times. 80 µL of master mix was overlayed into each of the RT reaction tubes, giving a total reaction volume of 100 µL. Tubes were capped with cap strips and retainer/tray assembly was removed from laminar flow hood and transferred to a thermocycler, which was programmed for cDNA amplification as follows: PCR mixtures were pre-incubated at 94° C. for 5 minutes, followed by 35 cycles of three-step incubations at 94° C. for 15 seconds, 55° C. for 30 seconds, and 72° C. for 1 minute, followed by a 5 minute incubation at 72° C. The completed primary PCR reaction was stored at 4° C. (short-term) or –20° C. (long-term) until ready for nested amplification.

Secondary/Nested PCR Master Mix Preparation:

GeneAmp RNA PCR Core Kit reagents were thawed at room temperature, except for enzymes, which were removed from freezer only when needed. Reagents were vortexed to mix and then briefly microcentrifuged and placed in an ice bucket. A sterile 1.5 ml microcentrifuge tube was placed in the ice bucket. Enough cDNA amplification/primary PCR master mix was prepared to accommodate the number of planned reactions plus one (to accommodate pipetting error), based on the following amounts of reagents per reaction: 10 µL 10×PCR Buffer II, 6 µL 25 mM MgCl$_2$, 4 µL 10 mM dNTP blend, 1 µL of each secondary primer (25 µM)(Table 3), 75.5 µL sterile water, 0.5 µL Taq polymerase (5U/µL). Primary PCR master mix and retainer assembly containing completed RT reactions were transferred to sterile laminar flow hood in the template addition area.

Secondary/Nested PCR Template Addition:

MicroAmp reaction tubes were labeled and placed in retainer/tray assembly. Secondary/nested PCR master mix was mixed by gently pipetting up and down a few times. 98 µL of master mix was added into each of the reaction tubes. 2 µL of the primary PCR reaction was added to corresponding secondary PCR reaction tube for a total volume of 100 µL. Tubes were capped with cap strips and the retainer/tray assembly was removed from the laminar flow hood and transferred to a thermocycler which was programmed for cDNA amplification as follows: re-incubated at 94° C. for 5 minutes, followed by 35 cycles of three-step incubations at 94° C. for 15 seconds, 55° C. for 30 seconds, 72° C. for 1 minute, followed by a 5 minute incubation at 72° C. The completed primary PCR reaction was stored at 4° C. (short-term) or –20° C. (long-term) until ready for nested amplification.

Sample Preparation for Agarose Gel Analysis:

6× gel-loading buffer was prepared as follows: 0.25% bromophenol blue, 0.25% xylene cyanol, 30% glycerol, and water up to desired final volume. A stock solution can be prepared and stored at room temperature. 20 µL of 6× gel-loading buffer was added to each secondary/nested PCR reaction tube. Samples were mixed by pipetting up and down.

Agarose Gel Preparation:

5×-TBE buffer was diluted to 0.5× with distilled water. Ethidium bromide was added to a final concentration of 0.5 µg/ml. A 4% (w/v) GTG NuSieve agarose solution was prepared by adding 6 g agarose to 150 ml 0.5×TBE/EtBr in a 250 ml glass Erlenmeyer flask. The agarose/TBE solution was gently mixed for 10 minutes at room temperature (to allow the agarose to hydrate), followed by heating in the microwave at 40% power for 10 minutes, mixing occasionally, until all agarose is completely dissolved. The dissolved agarose solution was gently cooled under cold running water and then poured into a previously set-up gel tray (with appropriate size gel comb), while making sure to minimize bubbles. The agarose was allowed to completely solidify for approximately 30-60 minutes at room temperature.

Agarose Gel Electrophoresis:

Once the agarose solidified, the comb was gently removed and the gel apparatus was prepared to receive running buffer. 0.5×TBE buffer, containing 0.5 μg/ml ethidium bromide, was slowly poured into the electrophoresis rig until the gel was completely submerged. 10 μl of the 100-bp DNA ladder was loaded into the first well of the agarose gel. Each secondary/nested PCR sample was loaded into subsequent wells of the agarose gel. The lid was placed on the gel apparatus and the voltage was turned on at 100-200V constant current until the bromophenol blue (lower dye front) reached the end of the gel. Care was taken not to run the gel to long so that the samples were not lost. The gel was visualized on the analytical setting of the UV transilluminator and photographed for record-keeping purposes. The desired PCR amplicon was approximately 140-bp in size.

DNA Extraction:

The gel was visualized using the preparative setting on the UV transilluminator. Each sample band was cut out of the gel with a clean razor blade or scalpel and place in a pre-weighed 1.5 ml microcentrifuge tube. The band was cut as close to its edges as possible, in preparation for the QIAquick separation kit which allows for a maximum of 400 μg of agarose. Blades were changed between bands to avoid sample cross-contamination. Amplified DNA was extracted from each agarose slice using Qiagen's QIAquick separation protocol (e.g. Qiagen's QIAquick Gel Extraction Kit Protocol (March 2001 Handbook)).

Purified DNA was analyzed spectrophotometrically and was adjusted to ~250 ng/μL. Approximately 90 μL DNA was used for the subsequent coreceptor analysis procedures. The purified DNA was transferred to sterile 1.5 ml screw-cap tubes and was either stored at 4° C. (short-term) or −20° C. (long-term) until ready for HTA analysis or TOPO TA cloning.

Polymerase Chain Reaction (RT-PCR) Amplication of Cloned HIV-1 Sequences to Generate Fluorescently-Labeled Probes for Qualitative and Quantitative Coreceptor Utilization Analysis The purpose of this procedure was to amplify a portion of the envelope gene of Human Immunodeficiency Virus type 1 (HIV-1), using cloned plasmid DNA. Fluorescent-labeled PCR primers were used to generate fluorescein-conjugated DNA probes. The resulting probes were subsequently used for qualitative and quantitative analysis of HIV-1 coreceptor utilization. Two sets of fluorescently-labeled primers were used to generate fluorescein-conjugated DNA probes, with the forward primer of each pair covalently linked at the 5' end to fluorescein. For primers see Table 4.

TABLE 4

Primers to make probes

| | |
|---|---|
| 5'F*V3-7092F: | 5'-/56-FAM/ GAA TCT GTA GAA ATT AAT TGT ACA AGA C-3' |
| V3-7232R: | 5'-TGC TCT ACT AAT GTT ACA ATG TGC TTG TCT TAT-3' |

TABLE 4-continued

Primers to make probes

| | |
|---|---|
| 5'F*V3HTA-EcoRI-F: | 5'-/56-FAM/ AAT TCG CCC TTG AAT CTG TAG AAA TTA AT-3' |
| V3HTA-EcoRI-R: | 5'-AAT TCG CCC TTT TTT GCT CTA CTA ATG-3' |

PCR Master Mix Preparation to Generate Probe for Qualitative HTA:

GeneAmp RNA PCR Core Kit reagents were thawed at room temperature, except for enzymes, which were removed from freezer only when needed. Reagents were vortexed to mix and then briefly microcentrifuged and placed in an ice bucket. A sterile 1.5 ml microcentrifuge tube was placed in the ice bucket. Enough cDNA amplification/primary PCR master mix was prepared to accommodate the number of planned reactions plus one (to accommodate pipeting error), based on the amounts of reagents per reaction as follows: 10 μL 10×PCR buffer II, 6 μL 25 mM $MgCI_2$, 4 μL 10 mM dNTP blend, 1 μL of each primer to make probe (at 25 μM)(Table 4), 76.5 μL sterile water, 0.5 μL Taq polymerase (5U/μL). At least four reactions were planned (one for each probe). A negative control containing sterile water instead of plasmid DNA was also prepared. This "qualitative" PCR master mix and retainer tray assembly were transferred to a sterile laminar flow hood in the template addition area.

PCR Master Mix Preparation to Generate Probe for Quantitative HTA:

GeneAmp RNA PCR Core Kit reagents were thawed at room temperature, except for enzymes, which were removed from freezer only when needed. Reagents were vortexed to mix and then briefly microcentrifuged and placed in an ice bucket. A sterile 1.5 ml microcentrifuge tube was placed in the ice bucket. Enough cDNA amplification/primary PCR master mix was prepared to accommodate the number of planned reactions plus one (to accommodate pipeting error), based on the amounts of reagents per reaction as follows: 10 μL 10×PCR buffer II, 6 μL 25 mM $MgCI_2$, 4 μL 10 mM dNTP blend, 1 μL of each primer to make probe (at 25 μM)(Table 4), 76.5 μL sterile water, 0.5 μL Taq polymerase (5U/μL). At least four reactions were planned (one for each probe). A negative control containing sterile water instead of plasmid DNA was also prepared. This "quantitative" PCR master mix and retainer tray assembly were transferred to a sterile laminar flow hood in the template addition area.

PCR Template Addition:

MicroAmp reaction tubes were labeled and placed in retainer/tray assembly. Each of the "qualitative" and "quantitative" PCR master mixes were mixed by gently pipetting up and down a few times. 99 μL of each master mix were added into reaction tubes. 1 μL of each plasmid DNA template ($SF_{162}$, JR-CSF, Sw54, and Sw87; derived from primary HIV-1 strains of the same name) was added to corresponding PCR reaction tube for a total volume of 100 μL. Tubes were capped with cap strips and retainer/tray assembly was removed from laminar flow hood and transferred to thermocycler, which was programmed for cDNA amplification as follows: pre-incubation at 94° C. for 5 minutes, followed by 35 cycles of three-step incubations at 94° C. for 15 seconds, 55° C. for 30 seconds, 72° C. for 1 minute, followed by a 5 minute incubation at 72° C. The completed PCR reaction can be stored at 4° C. (short-term) or −20° C. (long-term) until ready for cDNA amplification. PCR products were analyzed and gel-purified on a 4% agarose gel as described above.

Qualitative HIV-1 Coreceptor Utilization Analysis using a Heteroduplex Tracking Assay (HTA)

This assay uses a heteroduplex tracking (HTA) technique to analyze a portion of the Human Immunodeficiency Virus type 1 (HIV-1) envelope gene encompassing the key determinates of coreceptor utilization. Sequence difference between CCR5- and CXCR4-using variants result in distinct heteroduplex electrophoretic mobilities that allow the overall number and relative proportion of distinct variants to be estimated, even in samples consisting of heterogeneous CCR5 and CXCR4 pools. Plasma specimens showing heteroduplex patterns indicative of CXCR4 strains are then subjected to further analysis to quantitate the portion of CCR5 and CXCR4 viruses in the patient quasispecies. Interpretation of the gels is based on the banding pattern seen in each gel lane. The absence of clearly distinct X4-heteroduplex bands is indicative of a predominance of CCR5-utilizing strains of HIV-1. A schematic representation of qualitative HTA analysis of four different of targets: probe only, a CCR5 virus V3 region of the envelope gene a CXCR4 virus V3 region of the envelope gene, and a heterogeneous mix of CCR5 and CXCR4 virus V3 regions, is shown in FIG. 6.

Preparation of Non-Denaturing Polyacrylamide Gels:

12% acrylamide solution was prepared to accommodate the number of planned gels, based on the following amounts of reagents per 75 mL gel: 22.5 mL 40% (29:1) acrylamide/bis-acrylamide stock solution, 36.9 mL deionized water, 15 mL 5× Tris-Borate-EDTA (TBE) stock buffer, 52.5 µL TEMED, 525 µL 10% AMPS, freshly prepared in deionized water. The reservoirs of the electrophoresis tank were filled with 1×TBE (made with 1 part 5×TBE and 4 parts deionized water).

Heteroduplex Formation:

If necessary, prepared probe and target DNA were thawed at room temperature. Probe and target DNA were vortexed to mix and then microcentrifuged briefly and placed in an ice bucket. Between two and four sterile 1.5 ml microcentrifuge tubes were placed in the ice bucket (one tube per probe). Enough HTA annealing mix was prepared to accommodate the number of planned reactions plus one (to accommodate pipeting error), based on the following amounts of reagents per reaction: 3 µL 10×HTA annealing buffer, 5 µL FITC-labeled probe, 2 µL sterile water. MicroAmp reaction tubes were labeled and placed in retainer/tray assembly. HTA annealing mix was mixed by gently pipeting up and down a few times. 10 µL of master mix were aliquotted into each of the reaction tubes. 20 µL of viral RNA extracted from patient samples was then added. There were two to four reactions for each patient sample—one for each probe used. One positive control (the purified HIV-1 LAV extraction control) and one negative control (water only) were included in each run. These controls were also used to determine the amount of homoduplex and heteroduplex DNA present in each experiment. Tubes were capped with cap strips and the retainer/tray assembly was removed from the laminar flow hood and transferred to a thermocycler. The HTA annealing reaction was run for 2 minutes at 94° C., followed by quenching to 4° C. (short-term). The resulting reactions were placed on ice and immediately loaded on a 12% non-denaturing polyacrylamide gel.

Polyacrylamide Gel Electrophoresis:

6× gel-loading buffer was prepared by combining: 0.25% bromophenol blue, 0.25% xylene cyanol, 30% glycerol, water up to desired final volume. A stock solution may be prepared and stored at room temperature. 6 µL of 6× gel-loading buffer was added to each HTA annealing reaction tube and was mixed by pipeting up and down. Using a sequencing gel loading tip, the entire HTA annealing reaction was gently loaded into the polyacrylamide gel wells. The electrodes were connected to the power supply and the gel was run at a constant voltage until the last of the upper xylene cyanol dye front runs off the bottom of the gel (approximately 6 hours at 250V or overnight at 90V), or until the polyacrylamide gel marker dyes had migrated the desired distance.

Scanning and Gel Analysis:

The FluorImager 595 controls were adjusted to the following settings: 1) single label dye; 2) 488 nm excitation; 3) no emission filter; 4) no calibration; 5) 1000V PMT; 6) high sensitivity; 7) 200 µm pixels; and 8) 16-bit resolution. ImageQuaNT™ software package was used to display the gel image, once the scan was complete.

Interpretation of the gels is based on the banding pattern seen in each gel lane. The absence of clearly distinct heteroduplex bands is indicative of a predominance of CCR5-utilizing strains of HIV-1. Patient samples that contain only CCR5 viruses were assigned a QXR value of 1.0 [where QXR=(number of CCR5 clones)/(total number of clones analyzed)]. Specimens with detectible CXCR4 virus, on the other hand, were subjected to further quantitative analysis to quantitate the portion of CCR5 and CXCR4 viruses in the patient quasispecies using the procedures outlined below.

Example 6

Quantitative Coreceptor Utilization Analysis using a Heteroduplex Tracking Assay (HTA)

Cloning of HIV-1 Envelope Sequences for Quantitative Coreceptor Utilization Analysis:

The purpose of this procedure was to clone HIV-1 envelope sequences for quantitative coreceptor utilization anaylsis. HIV-1 RNA isolated and amplified from patient plasma was cloned into a plasmid vector (pCR®2.1-TOPO®, Invitrogen), used to transform chemically competent *Escherichia coli*, and plated onto selective bacterial media.

The following reagents per reaction were gently mixed and incubated for 5 minutes at room temperature and then placed on ice: 4 µL extracted DNA amplicon/sterile water, 1 µL salt solution, and 1 µL TOPO™ vector. Enough OneShot® *E. coli* cells were thawed on ice to accommodate the number of planned cloning reactions. 2 µL of the TOPO® cloning reaction was added to a vial of OneShot® *E. coli* and mixed gently using a pipette tip. *E. coli* was incubated on ice for 30 minutes and heat-shocked for 30 seconds at 42° C. 250 µL of room temperature SOC medium was added to the cells. Tubes were capped and incubated at 37° C. with gentle shaking for 1 hour. The entire transformation mixture was spread on LB/ampicillin/X-gal plates. The number of blue and white colonies on each plate were counted and recorded.

Isolation, Preparation, and Screening of Plasmid DNA Encoding Cloned HIV-1 Envelope Sequences for Quantitative Coreceptor Utilization Analysis The purpose of this procedure was to prepare high quality plasmid DNA encoding cloned HIV-1 envelope sequences for quantitative coreceptor utilization analysis. HIV-1 RNA isolated and amplified from patient plasma was cloned into a plasmid vector, grown overnight in 1-3 mL of *Escherichia coli* bacterial culture, and purified using a commercially available plasmid miniprep kit (Perfectprep®, Eppendorf, Westbury, N.Y.). Analysis for the viral specific sequences was carried out by digestion of the recombinant plasmid with restriction enzyme EcoRI (20 U/μL).

Screening of Plasmids by Restriction Enzyme Digestion:

A sterile 1.5 ml microcentrifuge tube was also placed in the ice bucket. Digests were performed in duplicate (one digest for agarose gel analysis and one digest for quantitative HTA analysis). Tubes were capped with strips and transferred to the thermocycler, which was programmed for EcoRI digestions as follows: 37° C. for 37 minutes followed by 95° C. for 1 minute. The completed restriction enzyme digests can be stored at 4° C. (short-term) or –20° C. (long-term) until ready for gel and HTA analysis.

10 μl of the 100-bp DNA ladder was loaded into the first well of the agarose gel. Each secondary/nested PCR sample was loaded into subsequent wells of the agarose gel. The desired band was approximately 160 bp in size. An additional band, representing linearized TOPO TA vector was also seen. The coreceptor utilization profile of positive transformants was then analyzed by HTA.

Quantitative Analysis Using an HTA of HIV-1 Coreceptor Utilization

This assay uses the heteroduplex tracking (HTA) technique described in Example 1 to analyze a portion of the Human Immunodeficiency Virus type 1 (HIV-1) envelope gene encompassing the key determinates of coreceptor utilization. Individual clones from patient plasma specimens which showed heteroduplex patterns indicative of CXCR4 strains were subjected to analysis to accurately quantitate the portion of CCR5 and CXCR4 viruses in the patient quasispecies. DNA heteroduplex tracking analysis was performed with the coreceptor utilization profile of a minimum of twenty positive transformants from each patient sample determined by using two probes to screen each clone. Probes were prepared from one laboratory CCR5 isolate (SF162 or JR-CSF) and one primary CCR5 isolate (Sw54 or Sw87). The QXR value for each patient specimen was then calculated based on the number of CCR5-specific clones obtained from each sample as follows: QXR=(number of CCR5 clones)/(total number of clones analyzed). FIG. 6 is a schematic representation of HTA analysis of four different targets: probe only, a CCR5 virus V3 region, a CXCR4 virus V3 region, and mixed quasispecies containing both CCR5 and CXCR4 virus V3 regions.

Example 7

Validation Experiments

PCR Primer Design

A common problem is low or no target DNA yield following PCR, reflecting either PCR efficiency or sample preparation problems. This problem was alleviated in part by use of a commercially available RNA extraction kit (Qiagen Viral RNA Kit), and in part by use of a small amount of pooled HIV-1 LAV, which is always simultaneously extracted as a positive RNA control. This practice is part of the standard operating procedure.

Primers used herein were designed to match the lade B consensus sequence as posted on the Los Alamos National Laboratories HIV database. Using this primer set, inventors currently have a success rate of 98.4% in amplifying envelope sequences from patient samples with a viral load of at least 1000 copies per milliliter of plasma.

Variant Sampling

Correct sampling is a recurring and frequently overlooked potential problem in subcloning and sequencing analyses of complex populations. Previously, inventors circumvented this problem by sequencing subclones derived from multiple independent PCR's or sequencing the dilution end point directly. For genetic differences in quasispecies detected as changes in HTA patterns to be significant, the populations being compared must be appropriately sampled. Any claims of quasispecies changes using HTA or other methods of direct population analyses must be substantiated through reproducibility of the results using the product of duplicate, independent amplifications to document proper sampling. To ensure proper variant sampling using the technique, inventors have compared the HTA results from independent duplicate PCR's. Inventors ran a series of HTA's using different amounts of input template and multiple parallel amplifications to prove that inventors can consistently amplify all of the majority and minority variants in a patient sample. Three levels of sequence difference between target DNA mixtures were selected to span the diversity found in the HIV-1 envelope gene. Duplicate 10-fold serial dilutions of viral RNA were then amplified by PCR and analyzed by HTA using our various probes. Inventors saw identical HTA patterns in each independent PCR, indicating reproducible and therefore correct sampling of the target populations. These studies also were repeated using various biological and molecular clones derived from primary isolates from patients previously examined in our treatment study (1). Finally, inventors repeated these sampling studies using RNA from primary patient isolates of known and unknown coreceptor usage. In each case, analysis of duplicate, independent PCR's demonstrated that the primers and the optimized PCR reaction conditions reproducibly amplify a mixture of HIV-1 variants that adequately reflects the population in the original sample.

Limits of Detection

The main advantage of HTA is its ability to simultaneously analyze multiple genetic variants coamplified by PCR. Using optimized reaction conditions, HTA's can be used to detect variants that represent less than 1% of the total quasispecies population (5). The ability of the coreceptor-specific HTA to detect rare variants has been examined by reconstituting mixtures of virus using laboratory isolates with known coreceptor usage. The sensitivity of the HTA method to detect R5 and X4 isolates was independently ascertained by using reconstituted samples with QXR values at or near 0 and 1, respectively. These experiments have demonstrated that inventors can routinely and reproducibly detect CCR5 and CXCR4 variants that represent as little as 0.2% of the total viral population.

Assay Validation Using Patient Isolates

Over the last five years inventors have isolated a large number of biologic and molecular clones of HIV-1, allowing us to compare genotypic predictions of coreceptor usage (either by performing V3 loop sequencing or by using our HTA method) with phenotypically-determined coreceptor preference.

Previously, inventors used a rapid RT-PCR based genotypic method to measure QXR, the proportion of HIV-1 utilizing CCR5 or CXCR4 as a coreceptor. This method relied on sequence analysis of the V3 region of the HIV-1 envelope gene to determine QXR. A total of 424 phenotypically-char acterized biological and molecular clones of HIV-1 were analyzed, yielding the following data:

|  |  | Phenotypic Result | |
| --- | --- | --- | --- |
|  |  | CCR5-using | CXCR4-using |
| Genotypic Prediction by V3 Sequencing | CCR5-using | 225 | 8 |
|  | CXCR4-using | 12 | 179 |

For detection of CCR5 strains of HIV-1, this sequencing-based approach thus achieves 94.9% sensitivity and 95.7% specificity.

A subset of clones from this sample set has also been examined using the newer HTA approach. A total of 392 clones have been analyzed:

|  |  | Phenotypic Result | |
| --- | --- | --- | --- |
|  |  | CCR5-usin | CXCR4-using |
| Genotypic Prediction by HTA | CCR5-using | 232 | 0 |
|  | CXCR4-using | 3 | 157 |

For detection of CCR5 strains of HIV-1, the HTA method achieves ~100% sensitivity and specificity. Conversely, for detection of CXCR4 strains of HIV-1, this method attains ~100% sensitivity and 98.7% specificity. The predictive values for detecting CCR5 and CXCR4 strains are 100% and 98.1%, respectively.

Example 8

HIV-1 Coreceptor Usage and CXCR4-Specific Viral Load Predict Clinical Disease Progression The purpose of this example is to show the relationship of HIV-1 coreceptor usage to clinical endpoints, and in particular the identification of patients at high risk for AIDS or death before or during cART.

Pioneering cohort studies of viral phenotype were performed before cART was introduced, and measured a phenotypic characteristic of X4 viruses, induction of syncytia in tissue culture (Koot et al. (1993)). Although the presence of syncytia-inducing virus was a strong predictor of HIV-1 disease progression, cell culture-based syncytia assays were impractical for clinical use and remained as research tools.

cART has become so effective that relatively few treated patients experience disease progression, and clinical trials rely primarily on surrogate markers for assessment (Ledergerber et al. (1999); and Mocroft et al. (2003)). Previous studies revealed, however, that patients displayed clinical benefits from therapy beyond those mediated through changes in CD4 count and HIV-1 load (Mocroft et al. (2003); Ledergerber et al. (2004); and Miller et al. (2004)). Inventors therefore focused on the relationship of HIV-1 coreceptor usage to clinical endpoints, asking whether quantification of coreceptor usage identified patients at high risk for AIDS or death during cART. To quantify HIV-1 coreceptor usage and determine X4-specific HIV-1 load, inventors developed a sensitive, nucleic acid-based assay to determine the proportion of virus in a patient's plasma that uses each coreceptor.

By examining patients in the Swiss HIV Cohort Study (SHCS) (Ledergerber et al. (1999); and Ledergerber et al. (1994) Soz Praventivmed 39:387-94), inventors assessed the predictive value of HIV-1 coreceptor usage before the initiation of therapy and, in those with persistent viraemia during cART, after 6 months of treatment.

The SHCS is a prospective, clinic-based, observational study of HIV-1-infected adults initiated in 1988, with documentation of follow-up visits every six months (Ledergerber et al. (1994)). A subset of patients were selected from 2674 who initiated cART between 1995 and 1998 and who were described in our previous report on clinical progression and persistent viremia (Ledergerber et al. (1999)). The study was approved by Institutional Review Boards at each site and each patient signed informed consent.

Selection of Study Subjects and Samples

First, inventors identified the 170 patients who subsequently progressed to a new clinical AIDS-defining event or death while receiving cART. To qualify for the present study, patients needed sufficient plasma available from the SHCS visit preceding the initiation of cART, called baseline, and an HIV-1 load≧1000 copies/mL at that visit. The median interval between the initiation of cART and the baseline visit was 18 days [Interquartile range (IQR) of −64-0 days]. Follow-up samples were obtained after ~6 months of cART, with a median interval between the pre- and post-cART samples of 184 days (IQR of 135-212 days). Because an HIV-1 load≧500 copies/mL was required of post-cART specimens, follow-up samples were analysed only in patients who did not achieve complete virologic suppression. Selection of all specimens allowed for at least one additional contemporaneous aliquot remaining in stock for future projects. Inventors retrieved 115 baseline specimens from progressors, and 19 of these from one site could not be analysed owing to a problem in shipping and handling. Inventors therefore quantified coreceptor usage in 96 baseline samples. Paired follow-up specimens were available from 39 patients, with coreceptor results obtained from all 39.

As a second step, inventors identified pre- and post-cART aliquots from 91 patients who did not progress within the period of the original study (up to Dec. 31, 1998) and who were matched to progressors according to the clinic site and year cART was initiated. With the requirement for one aliquot remaining in stock, 4 specimens lost to handling, and our inability to amplify from 7, inventors quantified coreceptor usage in 84 baseline and 31 follow-up samples from nonprogressors. In total, inventors analysed 180 baseline and 70 follow-up samples.

Markers of Disease Progression

CD4 lymphocyte counts were measured by using flow cytometry and HIV-1 RNA levels, by using the Cobas Amplicor test, with a level of detection of 500 copies/mL (Roche Diagnostics, Rotkreuz, Switzerland) (Ledergerber et al. (1999)).

Quantification of HIV-1 Coreceptor Usage

Inventors quantified the proportion of HIV-1 variants using R5 or X4 in each plasma sample by employing a non-radioactive, DNA heteroduplex tracking assay (HTA) developed based upon previous methods (Delwart et al. (1997) Methods 12:348-54); and Nelson et al. (1997) J. Virol. 71:8750-8). Because X4 variants ordinarily coexist in a viral swarm along with R5, (Berger et al. (1998); Shankarappa et al. (1999); Scarlatti et al. (1997); Koot et al. (1993); and Connor et al. (1997)), it was necessary to quantify the proportion of viruses in plasma using each coreceptor. This proportion was expressed as a variable called the Quantity of X4 and R5 (QXR), which represents the fraction of virus in a specimen using the R5 coreceptor. If QXR=1, almost all of the viruses in a population use R5; if QXR=O, almost all use X4. If a mixture of R5 and X4 viruses are present, QXR<1 (Philpott et al. (2001)).

Because the key determinants of viral coreceptor usage are encoded by the third variable domain (V3) of the envelope gene, (Ho et al. (2005) J. Virol. 79:12, 296-303; and Pastore et al. (2006) J. Virol. 80:750-8), inventors developed a nucleic acid-based assay focusing on this region of the HIV-1 genome. Viral RNA was extracted from patient samples by using a QIAamp viral RNA extraction kit (Qiagen, Valencia, Calif.), with samples from different patients processed separately to minimise possible cross-contamination or mislabeling. Reverse transcription and PCR amplification (RT-PCR) of a 143 by fragment spanning the V3 region of the env gene was performed as described under conditions designed to optimise efficiency and variant sampling (Philpott et al. (2001); and Fang et al. (2003) AIDS 18:153-159).

DNA heteroduplex formation was carried out by annealing fluorescein-labeled probes derived from four CCR5-using HIV-1 strains with a 10-fold excess of unlabeled target DNA. Sequence differences between envelope variants resulted in distinct heteroduplex electrophoretic mobilities, allowing rapid estimation of the overall number and relative proportion of R5 and X4 variants.

Validation Experiments

To evaluate whether the observed heteroduplex banding patterns accurately predicted coreceptor usage, inventors used the HTA to characterize ~400 biologic and molecular HIV-1 clones of known coreceptor specificity. The predictive value of the HTA method for detecting R5 and X4 strains was 100% and 98.7%, respectively. The sensitivity of the HTA method also allows rare variants to be detected and quantified; HIV-1 subpopulations that represent as little as 1% of the total quasispecies be can readily identified (Delwart et al. (1997). Those samples harbouring X4 strains (QXR<1) were subjected to more detailed analysis, during which V3 loops were cloned and individually analysed by using HTA.

After determining the coreceptor usage of each clone, inventors then calculated QXR for each plasma specimen by applying a mathematical model derived previously (Philpott et al. (2001). The X4-specific HIV-1 load was calculated by multiplying the total viral load by the proportion of the viral population using $$X4: X4\text{-specific viral load}=(\text{total HIV-1 load})(1-QXR)$$

Analyses of these and other plasma samples demonstrated that inventors were capable of determining HIV-1 coreceptor usage in 97% of samples with HIV-1 RNA loads≧1000 copies/mL and 85% of those with viral loads<1000 copies/mL.

Statistical Analysis

Virologic responses were measured in terms of the percentage of patients with HIV-1 RNA<500 copies/mL six months after initiating cART. For immunologic responses, inventors determined the change in CD4 counts between values obtained at baseline and those obtained at the visit closest to six months. QXR, the proportion of plasma HIV-1 using CCR5, was stratified into two categories:

(1) QXR=1 if all virus identified uses CCR5, and
(2) QXR<1 if X4 virus is detected The association between virologic responses and baseline QXR was assessed by comparing the percentages of patients with undetectable HIV-1 RNA load across the different strata by using Fisher's exact test. Immunologic responses across two strata were compared by Wilcoxon rank-sum tests.

Kaplan-Meier curves and Cox proportional hazard regression models were applied to quantify the association of baseline or follow-up QXR (equal 1 vs. less than 1) with subsequent clinical progression, defined as a new clinical AIDS-defining event or death.

In addition to the two QXR strata, inventors included an additional model analysing the relationship of X4 viral load to HIV-1 disease progression by stratifying X4-specific viral load into three strata:

(1) patients without detectable X4-specific viral load (i.e., QXR=1)
(2) patients with detectable X4 viraemia below the median value of X4-specific viral loads, and
(3) patients with detectable X4 viraemia above the median value of X4-specific viral loads.

To compare the predictive capacity with the established progression markers CD4 and HIV-1 RNA load inventors included concurrent $\log_2$ transformed CD4 values and $\log_{10}$ transformed HIV-1 loads in the univariable and multivariable Cox models. Inventors applied inverse probability weights to adjust for sampling bias.

Inventors used STATA (Version 9.1, StataCorp, College Station, Tex.) for analyses.

QXR can Predict the Response to cART

To examine whether QXR can predict the response to cART, inventors studied a subset of SHCS patients who initiated treatment in 1995-1998. Inventors compared 96 patients who progressed to a clinical AIDS-defining event or death with 84 contemporaneous non-progressors. Baseline demographic characteristics showed that progressing and non-progressing patients were comparable in age, sex, and risk for HIV-1 acquisition (P>0.1) (Table 5).

TABLE 5

Characteristics of 180 patients at initiation of cART (baseline).

| Characteristic | Value* | | |
|---|---|---|---|
| | Progressors n = 96 | Non-progressors n = 84 | Total |
| Median (IQR†) age, years | 36 (32-43) | 35 (30-41) | 36 (31-42) |
| Sex | | | |
| Male | 65 (68%) | 56 (67%) | 121 (67%) |
| Female | 31 (32%) | 28 (33%) | 59 (33%) |
| Risk factor for HIV-1 acquisition | | | |
| Injection drug use | 38 (40%) | 27 (32%) | 65 (36%) |
| Male homosexual contact | 27 (28%) | 32 (38%) | 59 (33%) |

TABLE 5-continued

Characteristics of 180 patients at initiation of cART (baseline).

| | Value* | | |
|---|---|---|---|
| Characteristic | Progressors n = 96 | Non-progressors n = 84 | Total |
| Heterosexual contact | 27 (28%) | 25 (30%) | 52 (29%) |
| Other or unknown | 4 (4%) | 0 (0%) | 4 (2%) |
| Clinical stage | | | |
| CDC stage A | 20 (21%) | 30 (36%) | 50 (28%) |
| CDC stage B | 36 (37%) | 20 (24%) | 56 (31%) |
| CDC stage C | 40 (42%) | 34 (40%) | 74 (41%) |
| Median (IQR) CD4*cell count per μL | 50 (18-137) | 119 (57-291) | 90 (29-192) |
| Median (IQR) viral load, $\log_{10}$ copies/mL | 5.3 (4.6-5.6) | 4.5 (4.0-5.2) | 4.9 (4.2-5.4) |
| Treatment naïve when starting cART | 37 (39%) | 38 (45%) | 75 (42%) |
| QXR | | | |
| Equals 1 | 52 (54%) | 67 (80%) | 119 (66%) |
| Less than 1 | 44 (46%) | 17 (20%) | 61 (34%) |
| Mean (IQR) QXR | 0.85 (0.8-1.0) | 0.92 (1.0-1.0) | 0.88 (0.9-1.0) |
| X4-specific viral load, $\log_{10}$ copies/mL⁺ | | | |
| 0 (QXR = 1) | 52 (54%) | 67 (80%) | 119 (66%) |
| 2.2-4.3 | 17 (18%) | 13 (15%) | 30 (17%) |
| >4.3 | 27 (28%) | 4 (5%) | 31 (17%) |
| Mean (IQR) X4 viral load, logo copies/mL | 3.5 (2.6-4.4) | 2.8 (2.6-2.6) | 3.2 (2.6-3.7) |

*Number of patients unless otherwise stated.
†IQR: Interquartile range.
⁺Stratification according to median of 61 values with non-zero values of X4-specific viral load.

As expected, however, the progressors exhibited evidence of more advanced HIV-1 infection (Table 5). Not only did they display lower CD4 counts and higher HIV-1 loads than did non-progressors, but they also were more likely to harbour X4-specific HIV-1 variants (P<0.0001 for all three comparisons). HIV-1 coreceptor usage is expressed here as a QXR value, with QXR<1 signifying a mixture of R5 and X4 variants and QXR=1 signifying all R5 strains. A significantly larger proportion of progressors exhibited QXR<1 than did non-progressors, and the mean X4-specific HIV-1 load was therefore higher in progressors as well (P<0.0001).

Patients whose samples were analyzed in this study were comparable to the entire SHCS population with respect to gender, age, and mode of HIV-1 acquisition (all P>0.1). Among SHCS non-progressors, however, individuals whose samples were analysed for QXR exhibited more advanced immunosuppression than patients whose samples were not analysed; 40% vs. 24% had CDC stage C disease, with a median baseline CD4 cell count of 119 vs. 207 cells/μL (both P<0.01). Among progressors, 42% of patients with QXR results had reached CDC stage C and the median baseline CD4 count was 50 cells/μL.

Inventors do not have an obvious explanation for this imbalance, but because it diminishes the difference between baseline predictors observed in progressors and non-progressors, it will result in an underestimation of the true effect of QXR.

Association of QXR with Immunologic and Virologic Responses

Inventors first determined whether QXR values before and during treatment were associated with immunologic responses to cART (Table 6).

TABLE 6

Association of virologic and immunologic responses 6 months after starting cART with QXR

| | QXR = 1 | QXR < 1 | P value |
|---|---|---|---|
| Baseline QXR | | | |
| Patients with HIV-1 RNA <500 copies/mL at 6 months, n (%) | 57 (68) | 27 (32) | 0.33* |
| CD4† cell increase [cells/pL] at 6 months, median (IQR) | 82 (24 to 155) | 40 (8 to 95) | 0.012† |
| Follow-up QXR | | | |
| CD4† cell increase [cells/μL] at 6 months, median (IQR) | 65 (29-110) | 11 (0-35) | 0.040† |

HIV-1 RNA viral loads at 6 months were available for 162/180 patients with baseline QXR values.
CD4 cell counts at 6 months available for 157/180 patients with baseline QXR values and for 58/70 with follow-up QXR values.
*Fisher's exact test;
†Wilcoxon rank-sum test Patients with baseline QXR<1 displayed significantly reduced CD4 responses to cART as compared to those with QXR=1 (40 vs. 82 cells, P=0.012). This finding was also observed in patients with persistent viraemia and QXR<1 after 6 months of cART (11 vs. 65 cells, P=0.04). The virologic response to cART, defined here as suppression of HIV-1 RNA load to <500 copies/mL after 6 months of treatment, was not associated with QXR at baseline (P=0.33).

QXR and Viral Load are Strong Predictors of Clinical Progression

Figure 7:
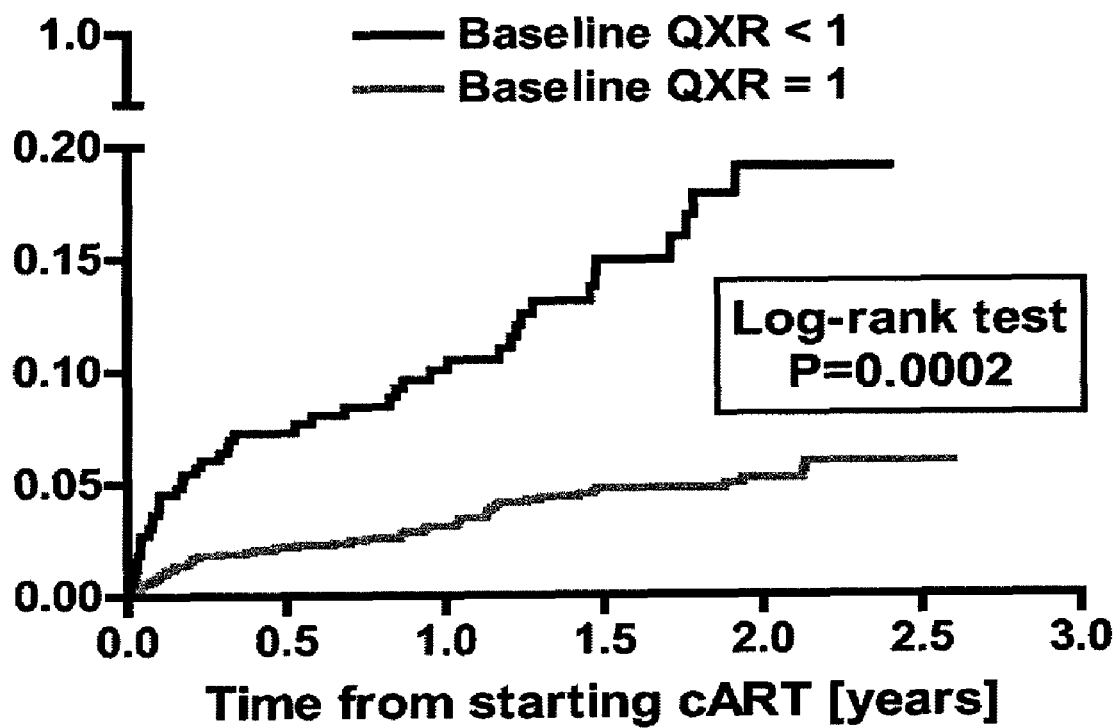
FIG. 7 provides Kaplan-Meier curves of association of clinical progression with baseline QXR (QXR=1 vs. QXR<1).

Kaplan-Meier estimates of the proportion of subjects who progressed to a new AIDS-defining illness or death, stratified according to QXR, revealed that QXR values strongly predicted the probability of disease progression when measured before the initiation of cART (P=0.0002) (FIG. 7) or, to a lesser extent, after 6 months of therapy in those with HIV-1 loads>500 copies/mL (P=0.04).

To examine the independent effect of QXR<1 and X4-specific viral load on disease progression, inventors applied Cox univariable and multivariable regression models (Table 7).

promise to be useful in clinical management. The quantification of QXR and X4-specific load may inform the decision to begin cART in untreated patients. It would be of interest to consider a clinical trial evaluating the initiation of cART in asymptomatic individuals with QXR<1, even those with CD4 counts>350 cells/uL. The aim of initiating cART in such patients would be to shift the predominant viral population from X4 to R5 (Philpott et al. (2001); Equils et al. (2000); and

TABLE 7

Univariable and multivariable Cox proportional hazard regression models of time from starting cART to new clinical AIDS defining illness or death by using baseline QXR or baseline X4-specific load together with CD4 cell counts and viral load as predictors.

| Variable at baseline | Univariable HR (95% CI) | Multivariable HR, including QXR (95% o CI) | Multivariable HR, including X4-specific viral load (95% CI)[†] |
|---|---|---|---|
| QXR | | | |
| Equal 1 | 1.0 | 1.0 | |
| Less than 1 | 3.5 (1.8-67) | 4.8 (2-3.10.0) | |
| X4-specific viral load, log10 copies/mL | | | |
| 0 (QXR = 1) | 1.0 | | 1.0 |
| 2.2-4.3 | 1.9 (0.9-4.3) | | 3.7 (1.2-11.3) |
| >4.3 | 7.1 (2.6-19.0) | | 5.9 (2.2-15.0) |
| Doubling of CD4[†] cell count | 0.72 (0.60-0.88) | 1.7 (1.0-3.0) | 1.6 (0.84-2.9) |
| Increase of viral load by $\log_{10}$ copies/mL | 2.2 (1.4-3.4) | 1.7 (1.0-3.0) | 1.6 (0.84-2.9) |

HR: Hazard ratio;
CI: Confidence interval
* Multivariable model includes baseline QXR and is adjusted for X4-specific and total viral load as well as CD4[†] cell count.
[†]Multivariable model includes baseline X4-specific viral load, stratified according to the median of 61 non-zero QXR values, and is adjusted for QXR, total viral load, and CD4[†] cell count.

The adjusted multivariable hazard ratio (HR) for clinical progression was 4.8 (95% CI: 2.3-10.0) for QXR<1 at baseline. For QXR<1 at follow-up, the univariable HR was 3.7 (1.1-13.0); and of borderline significance in the CD4 and HIV-1 RNA-adjusted multivariable model [HR 2.9 (0.95-8.7), P=0.06].

X4-specific HIV-1 load was a similarly independent predictor, with HRs of 3.7 (1.2-11.3) for baseline X4-specific viral loads of 2.2-4.3 $\log_{10}$ copies/mL and 5.9 (2.2-15.0) for X4 loads>4.3 $\log_{10}$ copies/mL.

Although total HIV-1 load and CD4 count were associated with clinical disease, QXR and X4-specific viral load strongly predicted disease progression during cART, independent of and in addition to CD4 count or total viral load.

This example identifies HIV-1 coreceptor usage as a powerful predictor of response to cART. Patients harbouring X4 variants not only exhibited a diminished immunologic response compared to those without X4 strains, but also displayed a markedly increased risk of progressing to AIDS or death despite treatment. The increased probability of clinical progression was observed in patients who displayed QXR<1 before initiating cART and in those with persistent viraemia and QXR<1 after 6 months of therapy.

Furthermore, patients with pretreatment X4-specific viral loads as low as 2.2-4.3 $\log_{10}$ copies/mLwere associated with a HR for clinical progression of 3.7, as compared to a HR of 1 for values<2.2 log10 copies/mL. For X4 loads>4.3 log10 copies/mL, the HR was 5.9.

Because QXR and X4-specific viral load identifies a subset of individuals at increased risk of clinical progression, they Skrabal et al. (2003)) as well as to reduce HIV-1 levels and thereby slow disease progression.

Of the patients in this study who exhibited HIV-1 loads>500 copies/mL after 6 months of cART, those harbouring X4 strains at follow-up were at increased risk of disease progression compared with those displaying only R5 variants. Therefore, patients with QXR<1 during cART might benefit from a change in therapy, with the aim of effective suppression or reduction of X4 strains. Serial measurements of QXR and X4-specific viral load would permit quantitative monitoring of these markers.

This example also helps to elucidate the tremendous clinical success of cART. Suppression of HIV-1 viraemia has become a major goal of treatment because it has been associated with slower disease progression and prevention of drug resistance. A number of cohort studies have shown that although many individuals initiating cART did not experience sustained suppression of plasma viraemia (Ledergerber et al. (1999); Mezzaroma et al. (1999); Deeks et al. (2000); and Ledergerber et al. (2004), the majority of these patients derived significant immunologic and clinical benefits. In addition, studies have documented that patients with advanced HIV-1 disease who continued cART had a reduced mortality rate as compared to untreated individuals with comparable CD4 counts and viral loads (Mocroft et al. (2003); Ledergerber et al. (2004); and Miller et al. (2004)). These reports demonstrate that cART provides clinical benefits beyond those mediated by the CD4 count and HIV-1 load.

Because cART has been shown to preferentially suppress X4 specific virus during the first years of therapy, this data supports the idea that the clinical gains bestowed by treatment stem from two effects on HIV-1: suppression of viraemia and shift of the viral population from X4 toward R5-using virus. The finding that clinical response was related to QXR at follow-up underscores this concept.

Previous analyses help to explain how X4 variants may affect responses to cART (Blaak et al. (2000); Kreisberg et al. (2001); and Jekle et al. (2003). The cytopathicity of HIV-1 primary isolates depends upon coreceptor usage and not the patient's disease status (Kreisberg et al. (2001)). One report focused on HIV-1 isolates from patients with persistent viraemia and drug resistance during cART, and compared characteristics of viruses from patients exhibiting a CD4 count increase, called a "paradoxical response," to those without an immunologic response (Solomon et al. (2005) J. Acquir. Immune Defic. Syndr. 40:140-8). Viral variants from the non-responders were more likely to demonstrate high replicative capacity, induce apoptosis, and use the X4 coreceptor than those from the responders.

Studies of paradoxical responders have suggested that the benefits of cART may stem from partial suppression of HIV-1 load in these patients and the diminished replicative capacity exhibited by many drug-resistant viruses (Deeks et al. (2000) J. Infect. Dis. 181:946-53). This report supports the role of preferential suppression of X4 variants as an additional means by which cART may lead to CD4 cell reconstitution or stability without complete viral suppression. The relationship between QXR and response to cART carries important implications for research on pathogenesis and therapeutics as well as clinical care.

A quantitative HTA permitted us to link clinical disease progression to QXR and X4-specific viral load. This sensitive assay revealed that >50% of the samples in this study harbouring X4 variants displayed QXR≧0.75, indicating that X4 strains comprised <25% of their viral quasispecies. These data demonstrate that the presence of X4 strains was associated with an increased probability of disease progression even when such variants comprised a small proportion of the HIV-1 population.

Because this investigation focused on a subset of SHCS participants who initiated cART in 1995-1998 (Ledergerber et al. (1999)), our selection of patients relied on the availability of cryopreserved plasma samples. Although the patients inventors studied were demographically comparable to the entire SHCS population, the non-progressors described in this report displayed more advanced immunosuppression than non-progressors whose samples were unavailable.

There is no obvious explanation for this unintentional imbalance. Because it diminishes the difference between progressors and non-progressors, inventors are confident, however, that the findings of this study remain valid. In addition, fewer samples were available for QXR analysis at follow-up than at baseline, owing primarily to the effectiveness of cART in suppressing HIV-1 load to <500 copies/mL.

The invention is further described by the following numbered paragraphs:

1. A diagnostic method comprising determining the viral load of a population of acquired immunodeficiency (AIDS) virus using the CXCR4 coreceptor (X4-specific viral load) in a patient-derived biological sample comprising the steps of:
   (a) screening individual molecular clones of patient-derived acquired immunodeficiency primary isolate with a heteroduplex tracking assay to determine CCR5 coreceptor usage and CXCR4 coreceptor usage of each individual molecular clone;
   (b) determining the proportion of HIV using the CCR5 coreceptor (R5) versus the CXCR4 coreceptor (X4) wherein the proportion is expressed as a variable called the Quantity of X4 and R5 (QXR), which represents the fraction of virus in a specimen using the R5 coreceptor;
   (c) determining coreceptor specific viral loads of the patient-derived acquired immunodeficiency primary isolate wherein the R5-specific viral load=(VL)(QXR) and the X4-specific viral load=(VL)(1−QXR)

wherein initiation or change of antiretroviral therapy may be considered anytime that the X4-specific viral load is greater than zero.

2. The diagnostic method according to paragraph 1, wherein if QXR=1, almost all of the viruses in the population use the R5 coreceptor;
   further wherein if QXR=0, almost all of the viruses in the population use the X4 coreceptor;
   further wherein if QXR<1, the viruses in the population use a mixture of the R5 and X4 coreceptors.

3. The diagnostic method according to paragraph 1, wherein the biological sample is any bodily fluid or tissue.

4. The diagnostic method according to paragraph 3, wherein the biological sample is a bodily fluid selected from the group consisting of blood, plasma, and spinal fluid.

5. The diagnostic method according to paragraph 1, wherein the individual molecular clones each comprise a DNA sequence corresponding to a portion of the HIV genome, the DNA sequence comprising at least a portion of the genetic determinates of coreceptor usage.

6. The diagnostic method according to paragraph 5, wherein the genetic determinates are derived from the env gene.

7. The diagnostic method according to paragraph 1, wherein the molecular clones each are derived from RNA of the patient-derived HIV and correspond to the HIV genome or a portion thereof and which comprise the genetic determinates of coreceptor usage or a portion thereof.

8. The diagnostic method according to paragraph 7, wherein the molecular clones are prepared by PCR of the RNA of the patient-derived HIV and at least one set of oligonucleotide primers.

9. The diagnostic method according to paragraph 8, wherein at least one set of oligonucleotide primers consists of the first set of primers in Table 3.

10. The diagnostic method according to paragraph 8, wherein the at least one set of oligonucleotide primers includes a second set of oligonucleotide primers, the second set consisting of the second set of primers in Table 3.

11. The diagnostic method according to paragraph 1, wherein the number of individual molecular clones is at least 20.

12. The diagnostic method according to paragraph 1, wherein the heteroduplex tracking assay comprises the steps of:
    (a) amplifying the individual molecular clone or a portion thereof by PCR to provide amplified DNA comprising the genetic determinates of coreceptor usage or a portion thereof;
    (b) forming a population of heteroduplex molecules by contacting the amplified DNA with a labeled probe complementary to the amplified DNA under conditions sufficient to form heteroduplexes;
    (c) separating the population of heteroduplex molecules using a separation means;
    (d) detecting the presence or absence of heteroduplex molecules;

wherein the presence or absence of heteroduplex molecules reveals coreceptor usage.

13. The diagnostic method according to paragraph 12, wherein the labeled probe is derived from a known HIV-1 CCR5 clone.

14. The diagnostic method according to paragraph 12, wherein the labeled probe is derived from a known HIV-1 CXCR4 clone.

15. The diagnostic method according to paragraph 12, wherein the labeled probe comprises a detectable moiety, a radioisotope, biotin, a fluorescent moiety, a fluorophore, a chemiluminescent moiety, or an enzymatic moiety.

16. The diagnostic method according to paragraph 1, wherein the method is used (a) to assess or predict the degree of HIV progression, (b) to determine when to start or change antiretroviral treatment, or (c) to monitor the efficacy of antiretroviral treatment.

17. The diagnostic method according to paragraph 2, wherein the method is used (a) to assess or predict the degree of HIV progression, (b) to determine when to start or change antiretroviral treatment, or (c) to monitor the efficacy of antiretroviral treatment.

18. A method of determining when to initiate antiretroviral therapy in a patient comprising determining the viral load of a population of AIDS virus using the CXCR4 coreceptor (X4-specific viral load) in a patient-derived biological sample comprising the steps of:
   (a) screening individual molecular clones of patient-derived acquired immunodeficiency primary isolate with a heteroduplex tracking assay to determine the CCR5 coreceptor usage and the CXCR4 coreceptor usage of each individual molecular clone;
   (b) determining the proportion of HIV using the CCR5 coreceptor (R5) versus the CXCR4 coreceptor (R4) wherein the proportion is expressed as a variable called the Quantity of X4 and R5 (QXR), which represents the fraction of virus in a specimen using the R5 coreceptor;
   (c) determining coreceptor specific viral loads of the patient-derived acquired immunodeficiency primary isolate wherein the R5-specific viral load=(VL)(QXR) and the X4-specific viral load=(VL)(1−QXR), wherein initiation or change of antiretroviral therapy may be considered anytime that the X4-specific viral load is greater than zero.

19. The method according to paragraph 18, wherein if QXR=1, almost all of the viruses in the population use the R5 coreceptor;
   further wherein if QXR=0, almost all of the viruses in the population use the X4 coreceptor;
   further wherein if QXR<1, the viruses in the population use a mixture of the R5 and X4 coreceptors.

20. The method according to paragraph 18, wherein the biological sample is a bodily fluid selected from the group consisting of blood, plasma, and spinal fluid.

21. The method according to paragraph 18, wherein the individual molecular clones each comprise a DNA sequence corresponding to a portion of the HIV genome, the DNA sequence comprising at least a portion of the genetic determinates of coreceptor usage.

22. The method according to paragraph 21, wherein the genetic determinates are derived from the env gene.

23. The method according to paragraph 18, wherein the molecular clones each are derived from RNA of the patient-derived HIV and correspond to the HIV genome or a portion thereof and which comprise the genetic determinates of coreceptor usage or a portion thereof.

24. The method according to paragraph 23, wherein the molecular clones are prepared by RT-PCR of the RNA of the patient-derived HIV and at least one set of oligonucleotide primers.

25. The method according to paragraph 24, wherein at least one set of oligonucleotide primers consists of the first set of primers in Table 3.

26. The method according to paragraph 24, wherein the at least one set of oligonucleotide primers includes a second set of oligonucleotide primers, the second set consisting of the second set of primers in Table 3.

27. The method according to paragraph 18, wherein the number of individual molecular clones is at least 20.

28. The method according to paragraph 18, wherein the heteroduplex tracking assay comprises the steps of:
   (a) amplifying the individual molecular clone or a portion thereof by PCR to provide amplified DNA comprising the genetic determinates of coreceptor usage or a portion thereof;
   (b) forming a population of heteroduplex molecules by contacting the amplified DNA with a labeled probe complementary to the amplified DNA under conditions sufficient to form heteroduplexes;
   (c) separating the population of heteroduplex molecules using a separation means;
   (d) detecting the presence or absence of heteroduplex molecules;

wherein the presence or absence of heteroduplex molecules reveals coreceptor usage.

29. The method according to paragraph 28, wherein the labeled probe is derived from a known HIV-1 CCR5 clone.

30. The method according to paragraph 28, wherein the labeled probe is derived from a known HIV-1 CXCR4 clone.

31. The method according to paragraph 28, wherein the labeled probe comprises a detectable moiety, a radioisotope, biotin, a fluorescent moiety, a fluorophore, a chemiluminescent moiety, or an enzymatic moiety.

32. The method according to paragraph 18, wherein the antiretroviral therapy is any suitable antiretroviral treatment regimen.

33. The method according to paragraph 32, wherein the antiretroviral therapy is selected from the group consisting of combination antiretroviral therapy (cART), protease inhibitors, fusion inhibitors, integrase inhibitors, coreceptor specific agents, nonnucleoside analogue reverse transcriptase inhibitors and nucleoside analogue reverse transcriptase inhibitors.

34. The method according to paragraph 33, wherein the nucleoside analogue reverse transcriptase inhibitor is 3TC.

35. The method according to paragraph 33, wherein the nucleoside analogue reverse transcriptase inhibitor is AZT.

36. The method according to paragraph 33, wherein the nonnucleoside analogue reverse transcriptase inhibitor is nevirapine.

37. A method of monitoring the efficacy of antiretroviral therapy in a patient comprising determining the viral load of a population of AIDS virus using the CXCR4 coreceptor (X4-specific viral load) in a patient-derived biological sample comprising the steps of:
  (a) screening individual molecular clones of patient-derived acquired immunodeficiency primary isolate with a heteroduplex tracking assay to determine the CCR5 coreceptor usage and the CXCR4 coreceptor usage of each individual molecular clone;
  (b) determining the proportion of HIV using the CCR5 coreceptor (R5) versus the CXCR4 coreceptor (R4) wherein the proportion is expressed as a variable called the Quantity of X4 and R5 (QXR), which represents the fraction of virus in a specimen using the R5 coreceptor;
  (c) determining coreceptor specific viral loads of the patient-derived acquired immunodeficiency primary isolate wherein the R5-specific viral load=(VL)(QXR) and the X4-specific viral load=(VL)(1−QXR);

wherein X4-specific viral load strongly predicts disease progression during cART.

38. The method according to paragraph 37, wherein if QXR=1, almost all of the viruses in the population use the R5 coreceptor;
further wherein if QXR=0, almost all of the viruses in the population use the X4 coreceptor;
further wherein if QXR<1, the viruses in the population use a mixture of the R5 and X4 coreceptors.

39. The method according to paragraph 37, wherein the biological sample is a bodily fluid, such as blood, plasma, and spinal fluid.

40. The method according to paragraph 37, wherein the individual molecular clones each comprise a DNA sequence corresponding to a portion of the HIV genome, the DNA sequence comprising at least a portion of the genetic determinates of coreceptor usage.

41. The method according to paragraph 40, wherein the genetic determinates are derived from the env gene.

42. The method according to paragraph 37, wherein the molecular clones each are derived from RNA of the patient-derived HIV and correspond to the HIV genome or a portion thereof and which comprise the genetic determinates of coreceptor usage or a portion thereof.

43. The method according to paragraph 42, wherein the molecular clones are prepared by RT-PCR of the RNA of the patient-derived HIV and at least one set of oligonucleotide primers.

44. The method according to paragraph 43, wherein at least one set of oligonucleotide primers consists of the first set of primers in Table 3.

45. The method according to paragraph 43, wherein the at least one set of oligonucleotide primers includes a second set of oligonucleotide primers, the second set consisting of the second set of primers in Table 3.

46. The method according to paragraph 37, wherein the number of individual molecular clones is at least 20.

47. The method according to paragraph 37, wherein the heteroduplex tracking assay comprises the steps of:
  (a) amplifying the individual molecular clone or a portion thereof by PCR to provide amplified DNA comprising the genetic determinates of coreceptor usage or a portion thereof;
  (b) forming a population of heteroduplex molecules by contacting the amplified DNA with a labeled probe complementary to the amplified DNA under conditions sufficient to form heteroduplexes;
  (c) separating the population of heteroduplex molecules using a separation means;
  (d) detecting the presence or absence of heteroduplex molecules;

wherein the presence or absence of heteroduplex molecules reveals coreceptor usage.

48. The method according to paragraph 47, wherein the labeled probe is derived from a known HIV-1 CCR5 clone.

49. The method according to paragraph 47, wherein the labeled probe is derived from a known HIV-1 CXCR4 clone.

50. The method according to paragraph 47, wherein the labeled probe comprises a detectable moiety, a radioisotope, biotin, a fluorescent moiety, a fluorophore, a chemiluminescent moiety, or an enzymatic moiety.

51. The method according to paragraph 37, wherein the antiretroviral therapy is any suitable antiretroviral treatment regimen.

52. The method according to paragraph 51, wherein the antiretroviral therapy is selected from the group consisting of combination antiretroviral therapy (cART), protease inhibitors, fusion inhibitors, integrase inhibitors, coreceptor specific agents, nonnucleoside analogue reverse transcriptase inhibitors and nucleoside analogue reverse transcriptase inhibitors.

53. The method according to paragraph 52, wherein the nucleoside analogue reverse transcriptase inhibitor is 3TC.

54. The method according to paragraph 52, wherein the nucleoside analogue reverse transcriptase inhibitor is AZT.

55. The method according to paragraph 52, wherein the nonnucleoside analogue reverse transcriptase inhibitor is nevirapine.

56. A diagnostic method for determining the viral load of a population of acquired immunodeficiency virus using the CXCR4 coreceptor (X4-specific viral load) in a patient-derived biological sample.

57. A diagnostic method comprising determining the viral load of a population of acquired immunodeficiency (AIDS) virus using the CXCR4 coreceptor (X4-specific viral load) in a patient-derived biological sample comprising the steps of:
  (a) screening individual molecular clones of patient-derived acquired immunodeficiency primary isolate with a V3 loop sequencing assay to determine CCR5 coreceptor usage and CXCR4 coreceptor usage of each individual molecular clone;
  (b) determining the proportion of HIV using the CCR5 coreceptor (R5) versus the CXCR4 coreceptor (X4) wherein the proportion is expressed as a variable called the Quantity of X4 and R5 (QXR), which represents the fraction of virus in a specimen using the R5 coreceptor;
  (c) determining coreceptor specific viral loads of the patient-derived acquired immunodeficiency primary isolate wherein the R5-specific viral load=(VL)(QXR) and the X4-specific viral load=(VL)(1−QXR).

58. The diagnostic method according to paragraph 57, wherein the V3 loop sequencing assay is a heteroduplex tracking assay.

59. The diagnostic method according to paragraph 58, further comprising an ultra deep sequencing assay.

Having thus described in detail preferred embodiments of the present invention, it is to be understood that the invention defined by the appended claims is not to be limited to particular details set forth in the above description as many apparent variations thereof are possible without departing from the spirit or scope of the present invention.

What is claimed is:

1. A diagnostic method comprising determining the viral load of a population of human immunodeficiency virus (HIV) using the CXCR4 coreceptor (X4-specific viral load) in a patient-derived biological sample comprising the steps of:
   (a) screening individual molecular clones of patient-derived HIV primary isolate with a nucleic acid molecule binding assay to determine CCR5 coreceptor usage and CXCR4 coreceptor usage of each individual molecular clone;
   (b) determining the proportion of HIV using the CCR5 coreceptor (R5) versus the CXCR4 coreceptor (X4) wherein the proportion is expressed as a variable called the Quantity of X4 and R5 (QXR), which represents the fraction of virus in a specimen using the R5 coreceptor;
   (c) determining coreceptor specific viral loads of the patient-derived (HIV) primary isolate wherein the R5-specific viral load=(VL)(QXR) and the X4-specific viral load=(VL)(1−QXR)
   wherein the method is used to assess or predict the degree of HIV progression, to determine when to start or change antiretroviral treatment, or to monitor the efficacy of antiretroviral treatment.

2. The diagnostic method according to claim 1, wherein the biological sample is any bodily fluid or tissue.

3. The diagnostic method according to claim 2, wherein the biological sample is a bodily fluid selected from the group consisting of blood, plasma, and spinal fluid.

4. The diagnostic method according to claim 1, wherein the individual molecular clones each comprise a DNA sequence corresponding to a portion of the HIV genome, the DNA sequence comprising at least a portion of the genetic determinates of coreceptor usage.

5. The diagnostic method according to claim 2, wherein the genetic determinates are derived from the env gene.

6. The diagnostic method according to claim 1, wherein the molecular clones each are derived from RNA of the patient-derived HIV and correspond to the HIV genome or a portion thereof and which comprise the genetic determinates of coreceptor usage or a portion thereof.

7. The diagnostic method according to claim 6, wherein the molecular clones are prepared by RT-PCR of the RNA of the patient-derived HIV and at least one set of oligonucleotide primers.

8. The diagnostic method according to claim 7, wherein at least one set of oligonucleotide primers consists of the first set of primers in Table 3.

9. The diagnostic method according to claim 7, wherein the at least one set of oligonucleotide primers includes a second set of oligonucleotide primers, the second set consisting of the second set of primers in Table 3.

10. The diagnostic method according to claim 1, wherein the number of individual molecular clones is at least 20.

11. The diagnostic method according to claim 1, wherein the nucleic acid molecule binding assay comprises the steps of:
   (a) amplifying the individual molecular clone or a portion thereof by PCR to provide amplified DNA comprising the genetic determinates of coreceptor usage or a portion thereof;
   (b) forming a population of bound molecules by contacting the amplified DNA with a DNA complementary to the amplified DNA under conditions sufficient to form heteroduplexes;
   (c) separating the population of bound molecules using a separation means;
   (d) detecting the presence or absence of bound molecules; wherein the presence or absence of bound molecules reveals coreceptor usage.

12. The diagnostic method according to claim 11, wherein the DNA complementary to the amplified DNA is derived from a known HIV-1 CCR5 clone.

13. The diagnostic method according to claim 11, wherein the DNA complementary to the amplified DNA is derived from a known HIV-1 CXCR4 clone.

14. The diagnostic method according to claim 11, wherein the DNA complementary to the amplified DNA comprises a detectable moiety, a radioisotope, biotin, a fluorescent moiety, a fluorophore, a chemiluminescent moiety, or an enzymatic moiety.

15. A method of determining when to initiate antiretroviral therapy in a patient comprising determining the viral load of a population of HIV virus using the CXCR4 coreceptor (X4-specific viral load) in a patient-derived biological sample comprising the steps of:
   (a) screening individual molecular clones of patient-derived HIV primary isolate with a nucleic acid molecule binding assay to determine the CCR5 coreceptor usage and the CXCR4 coreceptor usage of each individual molecular clone;
   (b) determining the proportion of HIV using the CCR5 coreceptor (R5) versus the CXCR4 coreceptor (R4) wherein the proportion is expressed as a variable called the Quantity of X4 and R5 (QXR), which represents the fraction of virus in a specimen using the R5 coreceptor;
   (c) determining coreceptor specific viral loads of the patient-derived (HIV) primary isolate wherein the R5-specific viral load=(VL)(QXR) and the X4-specific viral load (VL)(1−QXR);
   wherein antiretroviral therapy is initiated anytime that the X4-specific viral load is greater than zero.

16. A method of monitoring the efficacy of antiretroviral therapy in a patient comprising determining the viral load of a population of human immunodeficiency virus (HIV) virus using the CXCR4 coreceptor (X4-specific viral load) in a patient-derived biological sample comprising the steps of:
   (a) screening individual molecular clones of patient-derived HIV primary isolate with a nucleic acid molecule binding assay to determine the CCR5 coreceptor usage and the CXCR4 coreceptor usage of each individual molecular clone;
   (b) determining the proportion of HIV using the CCR5 coreceptor (R5) versus the CXCR4 coreceptor (R4) wherein the proportion is expressed as a variable called the Quantity of X4 and R5 (QXR), which represents the fraction of virus in a specimen using the R5 coreceptor;
   (c) determining coreceptor specific viral loads of the patient-derived (HIV) primary isolate wherein the R5-specific viral load=(VL)(QXR) and the X4-specific viral load=(VL)(1−QXR)
   wherein X4-specific viral load strongly predicts disease progression during cART.

* * * * *

UNITED STATES PATENT AND TRADEMARK OFFICE
CERTIFICATE OF CORRECTION

| | | |
|---|---|---|
| PATENT NO. | : 7,709,191 B2 | Page 1 of 1 |
| APPLICATION NO. | : 12/174141 | |
| DATED | : May 4, 2010 | |
| INVENTOR(S) | : Sean Philpott et al. | |

It is certified that error appears in the above-identified patent and that said Letters Patent is hereby corrected as shown below:

Column 1, line 36, please replace the following paragraph:

"STATEMENT OF RIGHTS TO INVENTIONS MADE UNDER FEDERALLY SPONSORED RESEARCH

This work was supported by the government, in part, by Grant U01A135004 from the National Institute for Allergy and Infectious Diseases and a National Research Service Award (1F32HD08478-01) from the National Institute of Child Health and Human Development. The government may have certain rights to this invention."

with

--STATEMENT REGARDING FEDERALLY SPONSORED RESEARCH OR DEVELOPMENT

This invention was made with government support under AI0135004 & HD008478 awarded by the National Institutes of Health. The government has certain rights in the invention.--

Signed and Sealed this
Twelfth Day of February, 2013

Teresa Stanek Rea
*Acting Director of the United States Patent and Trademark Office*